US 7,417,031 B2
(45) Date of Patent: *Aug. 26, 2008

(12) United States Patent
Enoki et al.

(10) Patent No.: US 7,417,031 B2

(54) USE OF ALGAE-DERIVED PHYSIOLOGICALLY ACTIVE SUBSTANCES FOR TREATING A CARCINOMATOUS DISEASE

(75) Inventors: Tatsui Enoki, Otsu (JP); Hiroaki Sagawa, Kusatsu (JP); Takanari Tominaga, Otsu (JP); Eiji Nishiyama, Moriyama (JP); Nobuto Koyama, Uji (JP); Takeshi Sakai, Hirosaki (JP); Fu-Gong Yu, Hirosaki (JP); Katsushige Ikai, Koka-gun (JP); Ikunoshin Kato, Uji (JP)

(73) Assignee: Takara Bio Inc., Shiga (JP)

( * ) Notice: Subject to any disclaimer, the term of this patent is extended or adjusted under 35 U.S.C. 154(b) by 139 days.

This patent is subject to a terminal disclaimer.

(21) Appl. No.: 11/034,243

(22) Filed: Jan. 13, 2005

(65) Prior Publication Data

US 2005/0119191 A1   Jun. 2, 2005

Related U.S. Application Data

(62) Division of application No. 10/228,195, filed on Aug. 27, 2002, now Pat. No. 6,911,432, which is a division of application No. 09/554,235, filed as application No. PCT/JP98/05065 on Nov. 11, 1998.

(30) Foreign Application Priority Data

| Nov. 11, 1997 | (JP) | ............................. 1997-323917 |
| Jan. 19, 1998 | (JP) | ............................... 1998-20146 |
| Apr. 27, 1998 | (JP) | ............................. 1998-130973 |
| May 29, 1998 | (JP) | ............................. 1998-164410 |
| Jul. 13, 1998 | (JP) | ............................. 1998-212041 |

(51) Int. Cl.
*A01N 43/04* (2006.01)
*A61K 31/715* (2006.01)
*C07G 3/00* (2006.01)
*C07G 11/00* (2006.01)
*C07G 17/00* (2006.01)
*C07H 15/00* (2006.01)
*C07H 17/00* (2006.01)
*C08B 37/00* (2006.01)

(52) U.S. Cl. .............................. 514/23; 514/54; 514/61; 536/4.1; 536/114

(58) Field of Classification Search ................... 514/23, 514/452; 536/1.11, 4.1; 435/8; 424/439, 424/400
See application file for complete search history.

(56) References Cited

U.S. PATENT DOCUMENTS

| 4,748,032 A | 5/1988 | Kono et al. |
| 4,857,346 A | 8/1989 | Sato et al. |
| 5,179,012 A | 1/1993 | Gudin et al. |
| 6,475,990 B1 * | 11/2002 | Enoki et al. .................... 514/23 |
| 6,518,302 B1 * | 2/2003 | Kobayashi et al. ........... 514/450 |
| 6,608,032 B1 * | 8/2003 | Enoki et al. .................... 514/23 |

FOREIGN PATENT DOCUMENTS

| EP | 0 341 062 A2 | 11/1989 |
| JP | 62-210965 A | 9/1987 |
| JP | 02-245087 | 9/1990 |
| JP | 07-165559 | 6/1995 |
| JP | 07-322886 A | 12/1995 |
| JP | 08-208435 A | 8/1996 |
| WO | WO 85/05031 | * 11/1985 |

OTHER PUBLICATIONS

Gura, T. "Systems for identifying new drugs are often faulty." Science, New Series, vol. 278, No. 5340, Nov. 7, 1997, pp. 1041-1042.*
Kobayashi, R. et al., "Neoagarobiose as a Novel Moisturizer with Whitening Effect", *Biosci. Biotech. Biochem.*, 61 (1), 1997, pp. 162-163.
Abstract, Derwent Publication, JP 53113043, Publication Date Oct. 3, 1978.
V.P. Zaitsev, et al., "Multipurpose Utilization of Marine Organisms", Moscow: Pishcheprom, 1980, pp. 29-44.

* cited by examiner

*Primary Examiner*—Shaojia Anna Jiang
*Assistant Examiner*—Layla Bland
(74) *Attorney, Agent, or Firm*—Browdy and Neimark

(57) ABSTRACT

Medicinal compositions for treating, ameliorating or preventing diseases with sensitivity to 3,6-anhydrogalactopyranose represented by formula (1):

(1)

foods, drinks, cosmetics, etc. containing as the active ingredient at least one member selected from the group consisting of the above-mentioned compound, its aldehyde, its hydrate and 2-O-methylated derivatives thereof and soluble sugar compounds containing the above compound. This compound also shows, for example, an apoptosis-inducing activity, a carcinostatic activity and inhibitory activities on the production of active oxygen, lipid peroxide radicals and NO, which makes it useful also as the active ingredient of antioxidants and preservatives.

4 Claims, 42 Drawing Sheets

Concentration of agarobiose (mM)

USE OF ALGAE-DERIVED PHYSIOLOGICALLY ACTIVE SUBSTANCES FOR TREATING A CARCINOMATOUS DISEASE

This is a division of co-pending parent application Ser. No. 10/228,195 filed Aug. 27, 2002, itself a division of grandparent application Ser. No. 09/554,235, now U.S. Pat. No. 6,475,990, issued on Nov. 5, 2002.

FIELD OF THE INVENTION

The present invention relates to use of a physiologically active substance derived from algae. More specifically, it relates to a pharmaceutical composition, an antioxidant, a preservative composition for keeping freshness of foods and drinks, and a cosmetic composition which comprise the physiologically active substance as an active ingredient, as well as a functional food or drink which comprises the physiologically active substance. Furthermore, it relates to a saccharide for exhibiting the function.

BACKGROUND OF THE INVENTION

Recently, a mode of death of cells or tissues called as apoptosis (self-blasting or self-destruction of cells) has been noticed.

The apoptosis is a death which has been originally programmed in the genome of a cell and is different from necrosis which is a pathological cell death. Certain external or internal factors trigger the activation of a gene that programs the apoptosis to cause the biosynthesis of a programmed death protein. In some cases, a programmed death protein which has been present in a cell in its inactive form becomes activated. The active programmed death protein thus formed decomposes the cell to lead death.

Activation of the apoptosis in desired tissues or cells would make it possible to eliminate cells which are unnecessary or harmful from a living body in a natural manner, which is of very importance.

OBJECTS OF THE INVENTION

Oligosaccharides derived from algae such as agar are expected to be developed as raw materials for foods (Food Chemical, 1988-2, 40-44; Bessatsu Food Chemical (Extra Number Food Chemical)-4, December, 1990, 127-131; JP-A-6-38691). However, their physiological functions such as an apoptosis-inducing activity are unknown.

The main object of the present invention is to develop a highly safe substance having a physiological function such as an activity of inducing apoptosis derived from a naturally occurring material, as well as to provide a pharmaceutical composition for preventing or treating a disease sensitive to the substance, such as a composition for inducing apoptosis comprising the substance as an active ingredient, and a functional food or drink comprising the substance as a constituent component.

SUMMARY OF THE INVENTION

In brief, the first aspect of the present invention is a pharmaceutical composition which comprises as an active ingredient at least one member selected from the group consisting of:

a compound selected from the group consisting of 3,6-anhydrogalactopyranose represented by formula 1:

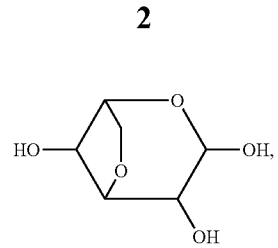

an aldehyde and a hydrate thereof, and 2-O-methylated derivatives of the 3,6-anhydrogalactopyranose, the aldehyde and the hydrate; and a soluble saccharide containing the compound at its reducing end, said composition being used for treating or preventing a disease sensitive to the compound.

The second aspect of the present invention is a food or drink comprising at least one member selected from the group consisting of:

a compound selected from the group consisting of 3,6-anhydrogalactopyranose represented by formula 1, an aldehyde and a hydrate thereof, and 2-O-methylated derivatives of the 3,6-anhydrogalactopyranose, the aldehyde and the hydrate; and a soluble saccharide containing the compound at its reducing end, said food or drink being used for ameliorating a disease state of or preventing a disease sensitive to the compound.

The third aspect of the present invention is an antioxidant which comprises as an active ingredient at least one member selected from the group consisting of a compound selected from the group consisting of 3,6-anhydrogalactopyranose represented by formula 1, an aldehyde and a hydrate thereof, and 2-O-methylated derivatives of the 3,6-anhydrogalactopyranose, the aldehyde and the hydrate; and a soluble saccharide containing the compound.

The fourth aspect of the present invention is a food and drink comprising the antioxidant of the third aspect of the present invention.

The fifth aspect of the present invention is a saccharide for an antioxidant selected from the group consisting of:

a compound selected from the group consisting of 3,6-anhydrogalactopyranose represented by formula 1, an aldehyde and a hydrate thereof, and 2-O-methylated derivatives of the 3,6-anhydrogalactopyranose, the aldehyde and the hydrate; and a soluble saccharide containing the compound.

The sixth aspect of the present invention is a preservative composition for keeping freshness of foods and drinks which comprises as an active ingredient at least one member selected from the group consisting of:

a compound selected from the group consisting of 3,6-anhydrogalactopyranose represented by formula 1, an aldehyde and a hydrate thereof, and 2-O-methylated derivatives of the 3,6-anhydrogalactopyranose, the aldehyde and the hydrate; and a soluble saccharide containing the compound.

The seventh aspect of the present invention is a cosmetic composition comprising as an active ingredient at least one saccharide selected from the group consisting of agarobiose, agarotetraose, agarohexaose, agarooctaose, κ-carabiose and β-D-galactopyranosyl-3,6-anhydro-2-O-methyl-L-galactose.

The eighth aspect of the present invention is an acidic food or drink comprising at least one member selected from the group consisting of:

a compound selected from the group consisting of 3,6-anhydrogalactopyranose represented by formula 1, an aldehyde and a hydrate thereof, and 2-O-methylated derivatives of the 3,6-anhydrogalactopyranose, the aldehyde and the hydrate; and a soluble saccharide containing the compound.

The further aspect of the present invention is use of at least one member selected from the group consisting of:

a compound selected from the group consisting of 3,6-anhydrogalactopyranose represented by formula 1, an aldehyde and a hydrate thereof, and 2-O-methylated derivatives of the 3,6-anhydrogalactopyranose, the aldehyde and the hydrate; and a soluble saccharide containing the compound, in preparation of a pharmaceutical composition, a food or drink, an antioxidant, a preservative composition for keeping freshness of foods and drinks or a cosmetic composition.

Hereinafter, the present invention will be explained in detail with reference to the attached drawings.

DETAILED DESCRIPTION OF THE INVENTION

Figure 1:
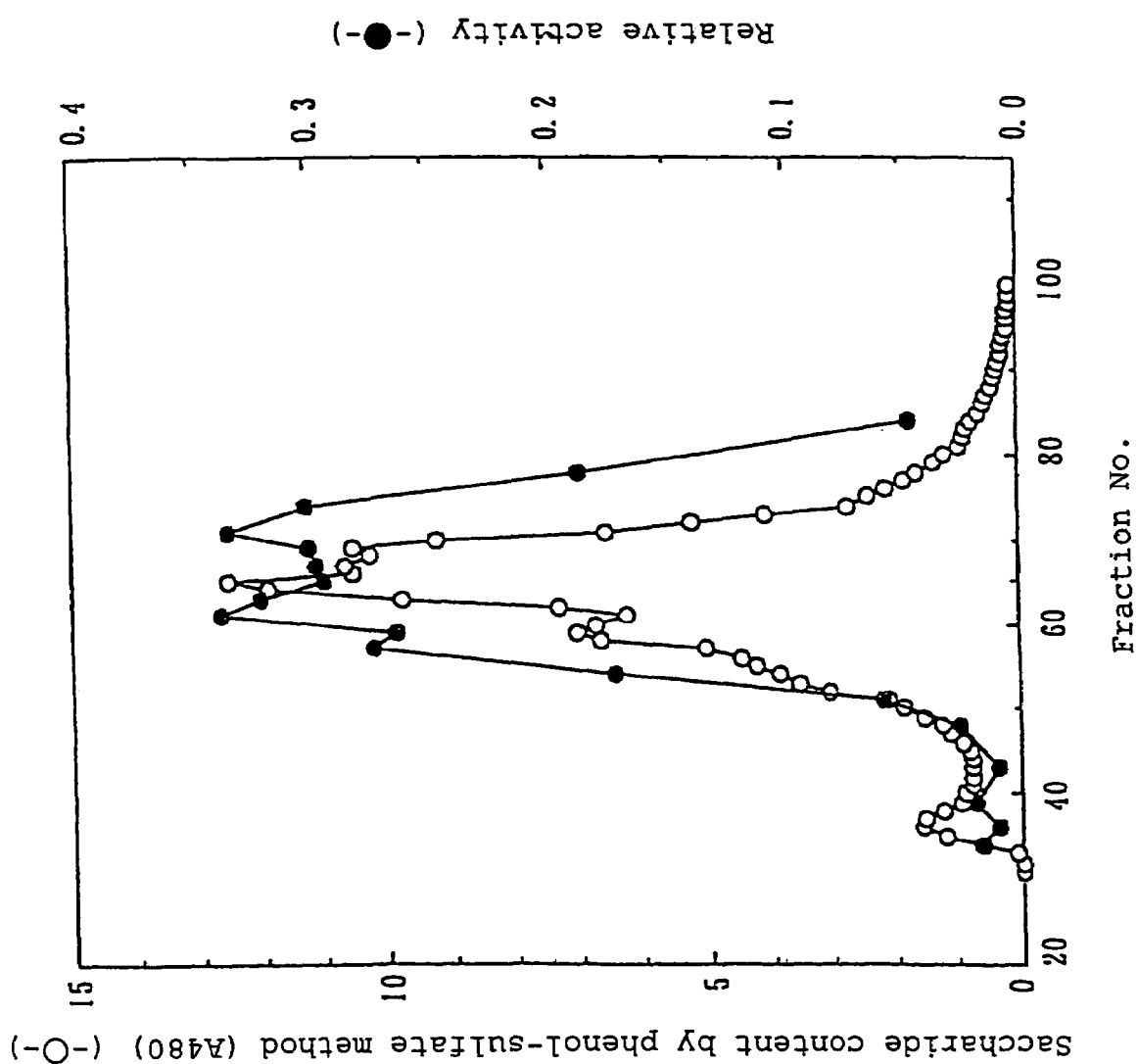
FIG. 1 illustrates a gel filtration elution pattern of agar decomposed with 0.12 N HCl.
Figure 2:
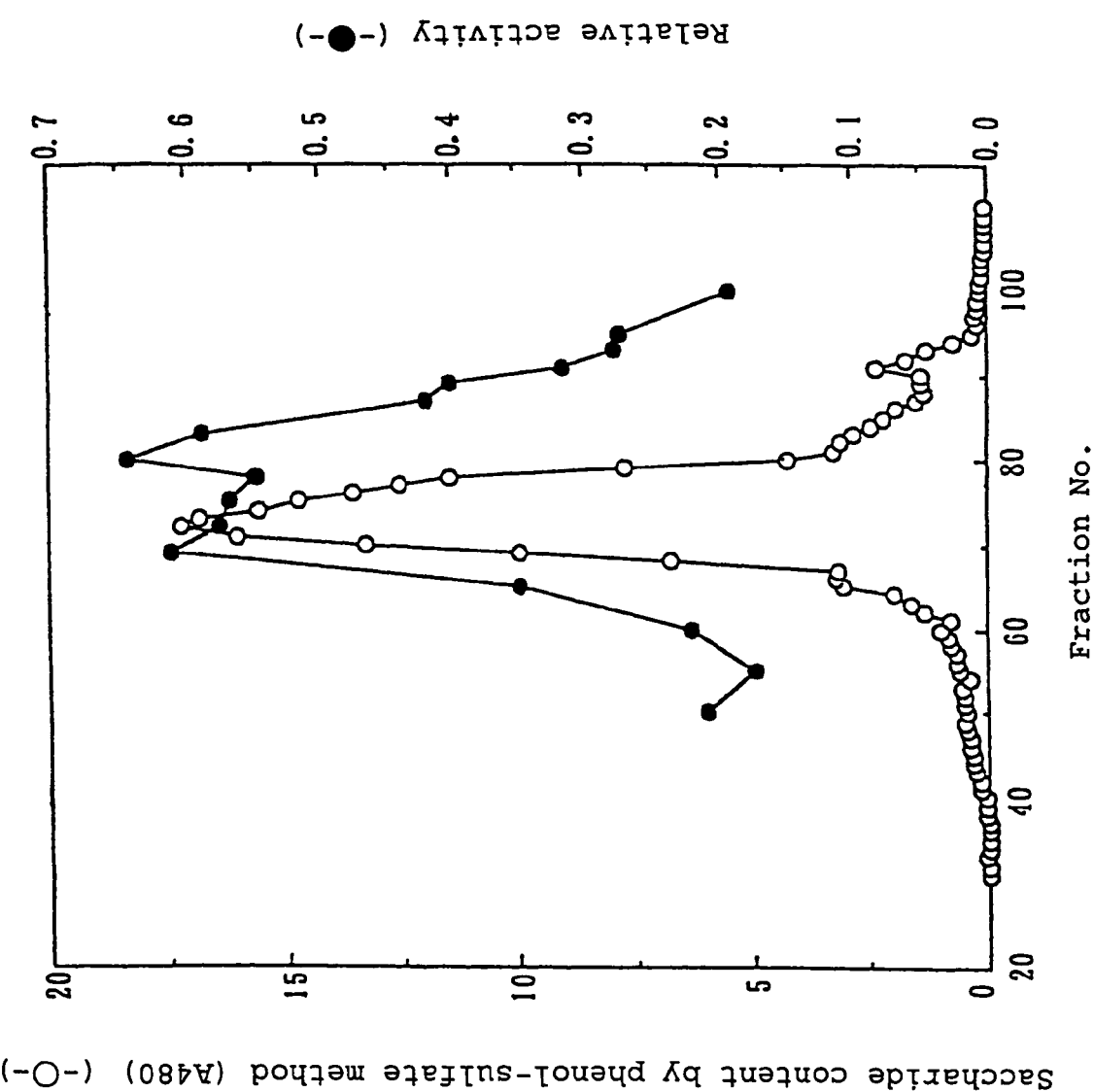
FIG. 2 illustrates a gel filtration elution pattern of agar decomposed with 1 N HCl.

An aldehyde of 3,6-anhydrogalactopyranose of formula 1 (hereinafter simply referred to as "3,6-anhydro-galactopyranose") of the present invention is a compound of formula 2:

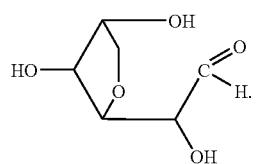

A hydrate thereof is a compound of formula 3:

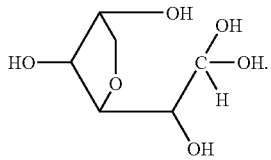

A 2-O-methylated derivative of the 3,6-anhydrogalactopyranose is a compound of formula 4:

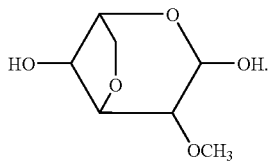

An aldehyde of the methylated derivative is a compound of formula 5:

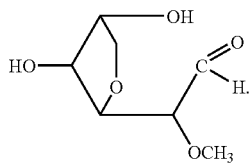

A hydrate of the methylated derivative is a compound of formula 6:

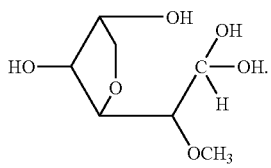

The structures of formulas 1 to 6 used herein may be represented by different expression forms. It is intended that such different expression forms and their possible tautomers are included in formulas 1 to 6. In addition, the configuration of formulas 1 to 6 is not limited to specific one as far as the desired activities are exerted, and may be in the D-form or L-form, or a mixture thereof.

The soluble saccharide of the present invention is, without limitation, a soluble saccharide containing at least one compound selected from 3,6-anhydrogalactopyranose, an aldehyde and a hydrate thereof, and 2-O-methylated derivatives of the 3,6-anhydrogalactopyranose, the aldehyde and the hydrate (hereinafter collectively referred to as "the compounds of formulas 1 to 6"), and can be obtained by decomposition of a substance containing at least one compound selected from the compounds of formulas 1 to 6 (hereinafter simply referred to as "a raw substance") under acidic conditions below pH 7 with an acid and/or enzyme, or by chemical synthesis. The soluble saccharide of the present invention is not limited to specific one in so far as it dose not solidify or semi-solidify (gelate) when used. Therefore, any saccharides containing at least one compound selected from the compounds of formulas 1 to 6 which become solated when used are included in the soluble saccharides of the present invention. Examples of the soluble saccharides suitably used in the present invention include a saccharide whose non-reducing end is a sugar other than L-galactose-6-sulfate, for example, agarobiose, agarotetraose, agarohexaose, agarooctaose, κ-carabiose, β-D-galactopyranosyl-3,6-anhydro-2-O-methyl-L-galactose and the like.

The raw substances used for obtaining the soluble saccharides are not limited to specific one and include, for example, viscous polysaccharides from red algae such as agarose, agaropectin, funoran, porphyran, carrageenan, furcellaran, and hypnean [Kyoritsu-shuppan Inc., "Tatouseikagaku 1—Kagakuhen—(Biochemistry of Polysaccharides 1—Chemistry—), pp. 314 (1969)].

The raw substances also include materials that contain these polysaccharides. For example, as raw materials for agarose and agaropectin, red algae belonging to *Gelidiaceae* such as *Gelidium amansii*, *Gelidium japonicum*, *Gelidium pacificum*, *Gelidium subcostatum*, *Pterocladia tenuis*, *Acanthopeltis japonica* and the like, red algae belonging to *Gracilariaceae* such as *Gracilaria verrucosa*, *Gracilaria gigas* and the like, red algae belonging to *Ceramiaceae* such as *Ceramium kondoi*, *Campylaephora hypnaeoides* and the like, and other red algae are used. Usually, several kinds of algae are used in combination as the raw materials. Although algae dried in the sun are usually used as the raw materials, both fresh and dried algae can be used in the present invention. Algae which are bleached while spraying water during drying, i.e., bleached raw algae, can also be used.

The raw material algae are extracted with hot water and then cooled to obtain "gelidium jelly". Water is removed from this "gelidium jelly" by freeze-dehydration or compress-dehydration, followed by drying to obtain agar. Agar in various forms such as bar, belt, board, thread, powder and the like can be used regardless of the source algae. Usually, agar contains about 70% of agarose and about 30% of agaropectin. The agar can be further purified to prepare agarose with high purity. Purified agarose with high purity or law purity having various agarose contents can be used.

The raw substances include the above-mentioned raw material algae, gelidium jelly, agar, purified agarose, purified agaropectin and intermediate products or side products obtained during preparation of these substances.

Agarose is a polysaccharide whose main structure is alternately linked D-galactose and 3,6-anhydro-L-galactose. In the structure, 1-position of D-galactose and 4-position of 3,6-anhydro-L-galactose are linked to each other through β-glycoside bond and 1-position of 3,6-anhydro-L-galactose and 3-position of D-galactose are linked to each other through α-glycoside bond. The α-1,3-bond is hydrolyzed by mild hydrolysis with a dilute acid or α-agarase [Carbohydr. Res., Vol. 66, p. 207 (1978)], and the β-1,4-bond is hydrolyzed by β-agarase selectively.

Carrageenan is a polysaccharide which is contained in red algae such as *Gigartinaceae, Solieriaceae, Hypneaceae* and the like. κ-Carrageenan, λ-carrageenan and η-carrageenan are known.

κ-Carrageenan has a fundamental structure in which 1-position of D-galactose-4-sulfate is linked to 4-position of 3,6-anhydro-D-galactose through β-glycoside bond, 1-postion of 3,6-anhydro-D-garactose is linked to 3-position of D-galactose-4-sulfate through α-glycoside bond, and they are repeated alternately. λ-Carrageenan has a fundamental structure in which 1-position of D-galactose is linked to 4-position of D-galactose-2,6-disulfate through β-glycoside bond, 1-position of D-galactose-2,6-disulfate is linked to 3-position of D-galactose through α-glycoside bond, and they are repeated alternately. Carrageenan is utilized as a gelatinizing agent of foods.

The raw substances of the present invention also include partially decomposed products of the above-mentioned raw substances using a chemical, physical and/or enzymatic method.

Examples of chemical decomposition include hydrolysis under acidic to neutral conditions. Examples of physical decomposition include radiation of electromagnetic waves or ultrasonic waves. Examples of enzymatic digestion include hydrolysis with a hydrolase such as agarase, carrageenase and the like.

Decomposition of the raw substances under acidic to neutral conditions are not limited to specific one in so far as the decomposition produces the compounds of formulas 1 to 6 and the soluble saccharides containing at least one of these compounds which have an apoptosis-inducing activity; a carcinostatic activity; antioxidant activities such as an activity of inhibiting active oxygen production, an activity of inhibiting nitrogen monoxide (hereinafter referred to as NO) production; an immunoregulatory activity; or the like. Examples of the saccharides include agarobiose, agarotetraose, agarohexaose, agarooctaose, κ-carabiose (hereinafter simply referred to "carabiose"), β-D-galactopyranosyl-3,6-anhydro-2-O-methyl-L-galactose, and the like; and the saccharides containing the compounds selected from the compounds of formulas 1 to 6 at their reducing ends whose non-reducing ends are saccharides other than L-galactose-6-sulfate.

For example, the raw substance is dissolved or suspended in an acid and reacted to produce the compound selected from the compounds of formulas 1 to 6 and the soluble saccharides containing at least one of these compounds to be used in the present invention. The reaction time required for the production of the compound selected from the compounds of formulas 1 to 6 and the soluble saccharides containing at least one of these compounds can be reduced by heating upon reaction.

The kind of the acid to be used for dissolution or suspension of the raw substances (for example, a substance that contains agarose or an agarose) is not limited to a specific one and may be inorganic acids such as hydrochloric acid, sulphuric acid, nitric acid and the like, organic acids such as citric acid, formic acid, acetic acid, lactic acid, ascorbic acid and the like, solid acids such as cation exchange resins, cation exchange fibers, cation exchange membranes and the like.

The concentration of the acid is not limited, but the acid can be used at a concentration of 0.0001 to 5 N, preferably 0.01 to 1 N. In addition, the reaction temperature is not limited, but the reaction may be carried out at 0 to 200 C, preferably 20 to 130 C. Furthermore, the reaction time is not limited, but the reaction may be carried out for a few seconds to a few days. The kind and the concentration of the acid, the reaction temperature and the reaction time may be suitable selected depending on the particular kind of the raw substance containing at least one compound selected from the compounds of formulas 1 to 6, such as agarose or carrageenan, as well as the compound of interest selected from the compounds of formula 1 to 6, the yield of the saccharide containing the compound, and the degree of polymerization of the soluble saccharide of interest containing the compound selected from the compounds of formulas 1 to 6 at its reducing end. In general, the acid decomposition reaction proceeds more rapidly by selecting a strong acid rather than a weak acid, a high acid concentration rather than a low acid concentration, and a high temperature rather than a low temperature.

Furthermore, in general, when a solid acid is used, a strong cationic exchange resin gives better decomposition reaction efficiency than a weak cationic exchange resin does. In addition, when the amount of the solid acid relative to the amount of the raw substance is more and the reaction temperature is higher, the acid decomposition reaction proceeds more rapidly.

For example, a solution of the saccharide used in the present invention which is obtained by suspending agar in 0.1 N hydrochloric acid in an amount of 10% by weight, dissolving the agar by heating at 100 C for 13 minutes and removing insoluble materials does not gelate any longer even when the solution is cooled to its freezing point. When the saccharide contained in this solution is analyzed by gel filtration HPLC, normal phase HPLC and the like, saccharides with high molecular weight are scarcely observed and almost all of the saccharides are decomposed to soluble saccharides composed of 10 or less sugars. Likewise, in case of a solid acid, a solution of the saccharide of the present invention obtained by converting 1 part by weight of a Na-type commercially available strong cationic exchange resin to its H type with 1 N hydrochloric acid, placed in 79 parts by weight of deionized water, adding and suspending 10 parts by weight of agar and heating the mixture at 95 C for 180 minutes dose not gelate any longer, even when the solution is cooled to its freezing point. When the saccharide contained in this solution is analyzed by gel filtration HPLC, normal phase HPLC and the like, saccharides with high molecular weight are scarcely observed and almost all of the saccharides are decomposed to soluble saccharides composed of 10 or less sugars.

Furthermore, for producing the soluble saccharide used in the present invention which has the compound selected from the compounds of formulas 1 to 6 at its reducing end, a large amount of the physiologically active oligosaccharide, such as a saccharide for an antioxidant, can be produced by using an organic acid such as citric acid, lactic acid or malic acid, suitably selecting the acid concentration ranging from several 10 mM to several M, the heating temperature ranging from 70 to 95 C, and the heating time ranging from several 10 minutes to 24 hours. In addition, the physiologically active oligosaccharide produced has long-term storage stability if it is maintained under acidic conditions while preventing them from becoming alkaline after hydrolysis.

The decomposed raw substances may be used directly or after being neutralized as the compounds to be used in the present invention, i.e., the compound selected from the compounds of formulas 1 to 6 and the soluble saccharides containing at least one of these compounds, for example, saccharides such as agarobiose, agarotetraose, agarohexaose, agarooctaose, κ-carabiose and β-D-galactopyranosyl-3,6-anhydro-2-O-methyl-L-galactose and the like. However, they may be further purified. The compound selected from the compounds of formulas 1 to 6 and the soluble saccharides containing these compounds at their reducing ends, for example, an oligosaccharide such as agarobiose, agarotetraose, agarohexaose, agarooctaose, κ-carabiose and β-D-galactopyranosyl-3,6-anhydro-2-O-methyl-L-galactose can be purified by using, for example, its apoptosis-inducing activity or carcinostatic activity as an index. As the means for purification, a known method such as a chemical method, a physical method or the like can be used. The compound selected from the compounds of formulas 1 to 6 or the soluble saccharide containing at least one of the compounds, which is an apoptosis-inducing substance, produced in the acid decomposition products can be purified by combining known purification methods such as gel filtration, fractionation using a molecular weight fractionating membrane, solvent extraction and chromatography using ion exchange resins or the like.

The structures of the resultant compounds can be analyzed by the known methods such as mass spectrometry, nuclear magnetic resonance, measurement of ultraviolet absorption spectrum or infrared absorption spectrum and the like.

Agarobiose, one example of the active ingredient of the present invention, is a disaccharide in which 1-position of D-galactose and 4-position of 3,6-anhydro-L-galactose are linked to each other through β-glycoside bond. An α-isomer and a β-isomer exist because an anomer carbon is present at 1-position of 3,6-anhydro-L-galactose, and agarobioses to be used in the present invention include both of the isomers.

The saccharide containing the compound selected from the compounds of formulas 1 to 6 at its reducing end used as the active ingredient in the present invention is one in which one or more sugars are bound to one or more hydroxide groups other than that at 1-position of the compound selected from the compounds of formulas 1 to 6, and is not limited to a specific one in so far as it has an apoptosis-inducing activity, a carcinostatic activity, antioxidant activities such as an activity of inhibiting active oxygen production, an activity of inhibiting NO production, etc., and/or an immunoregulatory activity. Examples thereof include decomposition products of the raw substances such as products from agarose obtained by decomposition with acid or digestion with α-agarase such as agarobiose, agarotetraose, agarohexaose, agarooctaose, agarodecaose, β-D-galacto-pyranosyl-3,6-anhydro-2-O-methyl-L-galactose and the like. Furthermore, products from carrageenan obtained by decomposition with acid or digestion with carrageenase such as carabiose can also be exemplified. Furthermore, the saccharides of the present invention which contain the compounds selected from the compounds of formulas 1 to 6 at their reducing ends include those in which one or more sugars selected from hexoses such as glucose, mannose, galactose, etc., pentoses such as xylose, arabinose, ribose, etc., uronic acids such as glucuronic acid, galacturonic acid, mannuronic acid, gluronic acid, etc., amino sugars such as glucosamine, galactosamine, etc., sialic acids such as N-acetylneuraminic acid, etc., deoxy sugars such as fucose, etc., as well as esters, amides and lactones thereof are bound to hydroxy groups other than that at 1-position of the compounds selected from the compounds of formulas 1 to 6. Furthermore, the saccharides of the present invention which contain the compounds selected from the compounds of formulas 1 to 6 at their reducing ends include those in which pyruvate and/or sulfate groups are bound to the saccharides containing the compounds selected from the compounds of formulas 1 to 6 at their reducing ends, for example, the saccharides such as agarobiose, agarotetraose, agarohexaose, agarooctaose, κ-carabiose, β-D-galactopyranosyl-3,6-anhydro-2-O-methyl-L-galactose and the like as well as the saccharides whose hydroxy groups are methylated. As described above, preferably, the saccharides of the present invention which contain the compounds selected from the compounds of formulas 1 to 6 at their reducing ends are those whose non-reducing ends are sugars other than L-galactose-6-sulfate.

Since an anomer carbon is present at 1-position of the compound at the reducing end of the saccharide containing 3,6-anhydrogalactopyranose or its 2-O-methylated derivative at its reducing end, an α-isomer and a β-isomer exist for such a compound. Both can be used as the saccharides of the present invention which contain 3,6-anhydrogalactopyranose or its 2-O-methylated derivative at their reducing ends.

The molecular weight is not specifically limited in so far as the compound has a physiological activity such as an apoptosis-inducing activity, a carcinostatic activity, antioxidant activities such as an activity of inhibiting active oxygen production, an activity of inhibiting NO production and/or an immunoregulatory activity.

Of course, a mixture of an α-isomer, a β-isomer, an aldehyde and a hydrated, and a mixture of a D-isomer and a L-isomer can be used in the present invention as the compound selected from the compounds of formulas 1 to 6 or the saccharide containing the compound at its reducing end.

Thus, the compound selected from the compounds of formulas 1 to 6 or the saccharide containing the compound at its reducing end used in the present invention has an apoptosis-inducing activity, a carcinostatic activity, antioxidant activities such as an activity of inhibiting active oxygen production, an activity of inhibiting lipid peroxide radical production, an activity of inhibiting NO production, an immunoregulatory activity and an anti-allergic activity. Then, according to the present invention, first, there is provided a pharmaceutical composition comprising as an active ingredient at least one of the compounds selected from the compounds of formulas 1 to 6 and the soluble saccharides containing these compounds at their reducing ends for treating or preventing a disease sensitive to at least one of these compounds, for example, a therapeutic or prophylactic composition for the disease.

Examples of diseases sensitive to these compounds include a diseases that requires induction of apoptosis for its treatment or prevention, a carcinomatous disease, a diseases that requires inhibition of active oxygen production for its treatment or prevention, a disease that requires inhibition of lipid peroxide radical production for its treatment or prevention, a disease that requires inhibition of NO production for its treatment or prevention or a disease that requires immunoregulation for its treatment or prevention such as an allergic disease. The pharmaceutical composition for treating or preventing these diseases of the present invention can be used as a composition for inducing apoptosis, a carcinostatic composition, antioxidants such as an inhibitor of active oxygen production, an inhibitor of lipid peroxide radical production, an inhibitor of nitrogen monoxide production, an anti-inflammatory composition, an immunoregulator, an anti-allergic composition and the like.

For example, the composition for inducing apoptosis of the present invention is useful for eliminating auto-reactive lymphocytes from patients suffered from autoimmune diseases, tumor cells, cells infected with a virus and the like. It can be used to eliminate unnecessary or harmful cells from a living body in a natural manner by causing apoptosis in the desired tissues or cells. Examples of diseases for which the composition for inducing apoptosis of the present invention is effective include autoimmune diseases such as systemic lupus erythematosus, immune mediated glomerulonephritis, multiple sclerosis, collagen disease, etc., rheumatism, and the like.

The composition for inducing apoptosis of the present invention can be used in a method for inducing apoptosis and the method is useful for elucidation of mechanism of induction of apoptosis, as well as screening for apoptosis-inducing compounds and inhibitors of apoptosis induction.

Since the activity of inducing apoptosis by the composition for inducing apoptosis of the present invention is inhibited by Caspase inhibitor, for example, IL-1β converting enzyme inhibitor V [Z-Val-Ala-DL-Asp(OMe)-fluoromethylketone: manufactured by Takara Shuzo]. Thus, the apoptosis induced by the composition is considered to be a cell death due to apoptosis depending on Caspase.

Caspase has been shown that it functions as an important mediator of apoptosis because it increases prior to various cell death; its overexpression induces cell death; the apoptosis is inhibited by a peptide inhibitor or an inhibitory protein such as CrmA and p35; and, in a knockout mouse for Caspase-1 or Caspase-3, a part of apoptosis normally observed is inhibited [Seikagaku (Biochemistry), vol. 70, p. 14-21 (1998)]. That is, during apoptosis process, Caspase which is a cysteine protease is activated to decompose nuclear or cytoplasmic proteins. Caspase is first synthesized as a precursor and then activated by processing. Regulation of this Caspase activation decides the life or death of cells. The mammals have 10 or more types of Caspases. An upstream Caspase processes a downstream Caspase to amplify the activity of decomposing intracellular proteins in a cascade mode [Saibo Kogaku (Cell Technology), Vol. 17, p. 875-880 (1998)]. On the contrary, the processing activity can be inhibited by inhibitor of the cysteine protease, Caspase, to stop cell death by Caspase dependent apoptosis.

The compound used in the present invention is useful for inhibition of production of oxidizing materials such as active oxygen. Then, an antioxidant such as an inhibitor of active oxygen production which comprises the compound as its active ingredient is useful for treating or preventing diseases caused by production and/or excess of active oxygen.

In general, active oxygen can be classified into radical active oxygen and non-radical active oxygen. The radical active oxygen includes hydroxy radical, hydroxyperoxy radical, peroxy radical, alkoxy radical, nitrogen dioxide ($NO_2$), NO, thylradical and superoxide. On the other hand, the non-radical active oxygen includes singlet oxygen, hydrogen peroxide, lipid hydroperoxide, hypochlorous acid, ozone and peroxonitrite. All of them are related to various pathological states such as inflammatory diseases, diabetes, cancers, arteriosclerosis, neurosis, ischemic reperfusion disorder and the like.

In a living body, active oxygen is always produced at a low concentration in some pathways. These are superoxide physiologically leaking out from an electron transport system such as mitochondria, hydrogen peroxide, hydroxy radical catalyzed with a transition metal such as copper and iron, hypochlorous acid formed by neutrophils or monocytes for protecting against infections, NO produced by decomposition of arginine and the like, and they are inevitable. A living body has a system eliminating active oxygen including enzymes and low molecular weight compounds against the production of active oxygen to maintain the balance between the production and the elimination. However, a living body is damaged oxidatively when the system for producing active oxygen becomes predominant over the eliminating system due to the activation of the above-mentioned pathways for some reasons or, to the contrast, due to the inactivation of the eliminating system. Such conditions are called as oxidative stress. Furthermore, in addition to the imbalance inside the body, the living body is always exposed to oxidative stress by materials outside the body such as the atmosphere, foods and the like. Therefore, oxidative stress is inevitable in everyone's daily life.

That is, as described above, the oxidative stress is related to various diseases and a living body is always exposed to circumstances in which diseases are caused by or disease conditions become more serious due to oxidative stress. Therefore, the antioxidant such as the inhibitor of active oxygen production of the present invention is useful for preventing and treating the diseases caused by oxidative stress or preventing the worsening of the disease conditions due to such oxidative stress.

Furthermore, a lipid peroxidation reaction is always associated with oxidative stress and proceeds at once upon production of a lipid peroxide radical. 4-Hydroxy-2-nonenal (HNE) produced therein is a toxic aldehyde specifically targeting glutathione or a protein. Reaction products of HNE and protein are detected in various disease tissues and considered to be inducing factors of disease conditions associated with oxidative stress. Then, the antioxidant which comprises the antioxidant substance used in the present invention which can inhibit production of lipid peroxide radicals is useful for preventing and treating age-related diseases caused by oxidative stress.

NO is the main component of an endothelium-derived relaxing factor (EDRF) [Nature, Vol. 327, p. 524-526 (1987)]. According to the present invention, there is provided a pharmaceutical composition for treating or preventing a diseases that requires inhibition of NO production for its treatment or prevention.

In the present invention, diseases that require inhibition of NO production are not limited to specific one and include for example, systematic hypotension caused by toxic shock, treatment with some cytokines and the like, blood pressure response reduction, autoimmune diseases, inflammation, arthritis, rheumatoid arthritis, diabetes, inflammatory bowel diseases, vascular function failure, pathogenic angiectasis, tissue injury, cardiovascular ischemia, hyperalgesia, cerebral ischemia, diseases associated with vascularization, cancers and the like, inclusive the diseases described in JP-A 9-504524, JP-A 9-505288, JP-A 8-501069, JP-A 8-512318 and JP-A 6-508849.

For NO synthases (NOS) which produces NO and L-citrulline from L-argnine and oxygen, a cNOS type which are constitutively expressed, and an iNOS which is a inducible type are known. In macrophages and the like, iNOS is induced by stimulation of cytotoxin or cytokines (for example, LPS, INF-δ) to produce NO. iNOS itself is essential to maintain a living body system. However, on the other hand, it has been shown that iNOS causes various diseases when it is expressed excessively by various factors to produce excess NO.

The present inventors have confirmed that the compounds selected from the compounds of formulas 1 to 6 and the soluble saccharides containing these compounds at their reducing ends such as agarobiose, agarotetraose and agarohexaose inhibit this iNOS expression. The confirmation was carried out at protein level by western blotting and at messenger RNA level by RT-PCR. That is, the compounds used in the present invention are useful for treating and preventing diseases that require inhibition of NO production by inhibiting expression of iNOS which is overexpressed by various factors to produce excess NO.

The compounds of the present invention inhibit NO production in macrophages and are useful for treating and preventing diseases caused by NO production in macrophages, inflammation, cancers and the like. In addition, inhibition of NO production by the saccharides used in the present invention is not antagonistic inhibition of NO production inducing substances such as LPS or INF-γ. Increase in inhibitory effect on NO production is observed by addition of the saccharides used in the present invention in advance. Therefore, the compounds of the present invention are very useful as those for preventing antioxidant production.

The inhibitor of NO production of the present invention is useful for studying the mechanism of NO production, and the mode of action of NO and can be used for screening of materials involved in the mechanism of NO production.

Vascularization is necessary for growth of a solid cancer, and vascular endothelial growth factor/vascular permeability factor (VEGF) play important roles in this process. In various tumor cells, VEGF is induced by NO. The inhibitor of NO production of the present invention also inhibits VEGF production of tumor cells by inhibiting NO production, thereby inhibiting vascularization around cancer tissues. When the inhibitor of NO production of the present invention is administered to a mouse in which tumor cells have been transplanted subcutaneously to form a solid cancer, vascularization around the cancer tissue becomes insufficient and the cancer falls out.

Nitrosoamines are a series of compounds in which nitro group is attached to a secondary amine and several hundred types are known. Many of them show carcinogenic activity to animals by damaging DNA. Nitrosoamines are considered to have a high relation to carcinogenesis of a human being and usually produced by a reaction of a nitrite and an amine in a stomach. NO also produces a nitrosoamine by reaction with an amine under physiological conditions at a neutral pH range. NO production is accelerated in a patient suffered from clonorchiasis or cirrhosis that have a high relation to a cancer epidemiologically. Therefore, in particular, carcinogenesis of a high-risk group can be prevented by administration of the inhibitor of NO production of the present invention to prevent acceleration of NO production. As described hereinabove, the inhibitor of NO production of the present invention shows its carcinostatic activity in two step, that is, suppression of carcinogenesis and inhibition of vascularization in cancer tissues.

NO also induces edema which is specifically recognized in inflammatory lesions, i.e., vascular permeability accelerating activity [Maeda et al., Japanese Journal of Cancer Research, Vol. 85, p. 331-334 (1994)] and accelerates biosynthesis of prostaglandins which are inflammatory mediators [Salvemini et al., Proceedings of National Academy of Sciences, USA, Vol. 90, p. 7240-7244 (1993)]. On the other hand, NO reacts with a superoxide radical quickly to produce peroxonitrite ion and this peroxonitrite ion also considered to cause inflammatory damages of cells and tissues.

NO production is induced when activated immune cells enter in an organ and release cytokines. Insulin-dependent diabetes is induced by specific destruction of islet β cells and this destruction is considered to be caused by NO. Synovial fluid in the lesion of a patient suffered from rheumatoid arthritis, osteoarthrosis, gouty arthritis and arthritis associated with Behçet disease contains NO at a concentration higher than that in the normal joint of the same patient or joints of healthy people. When the inhibitor of NO production of the present invention is administered to such patients, NO production in the lesion is inhibited to improve disease conditions.

NO production is increased during cerebral ischemia and after re-perfusion, which causes damages in cerebral tissues. Administration of the inhibitor of NO production of the present invention to a patient during cerebral ischemia relieves the damage of cerebral tissue and improves the prognosis.

The immunoregulator of the present invention has immunoregulatory activities such as an activity of suppressing lymphocyte blastogenesis and an activity of suppressing mixed lymphocyte reaction. Thus, the immunoregulator of the present invention is useful as a pharmaceutical composition for treating or preventing diseases caused by abnormality of these immune systems or immune factors.

Lymphocyte blastogenesis is a reaction in which mitogen binds to a receptor on the surface of a lymphocyte to activate the lymphocyte and promotes its division and proliferation. Mixed lymphocyte reaction is a reaction in which lymphocytes obtained from allogeneic animals are mixed and cultured, thereby inducing activation of lymphocytes due to incompatibility of major histocompatibility antigens to promote the division and proliferation of lymphocytes. The immunoregulator of the present invention suppress these reactions and is useful as a pharmaceutical composition for treating and preventing chronic diseases caused by abnormal acceleration of lymphocytes, for example, autoimmune diseases such as chronic nephritis, ulcerative colitis, type I diabetes and rheumatoid arthritis and is also useful for suppression of graft rejection.

In mast cells sensitized with IgE antibody, degranulation is induced by binding of an antigen and a chemical mediator is released. This type I, i.e. the immediate-type allergic reaction plays an important role in allergy diseases whose representative examples are asthma and atopic dermatitis, and substances which suppress release of chemical mediators from mast cells are considered to be very effective for treating and preventing these allergic diseases.

Passive cutaneous anaphylaxis (PCA) of a rat which is a model of the type I allergic reaction is initiated with degranulation of mast cells, followed by release of chemical mediators contained in granules such as histamine and serotonin to cause increase in vascular permeability and finally to cause pigment leakage in a local skin. This model is used as a model for estimating anti-allergic compounds in vivo most frequently.

The compounds selected from the compounds of formulas 1 to 6 and the soluble saccharides containing these compounds at their reducing ends has an activity of inhibiting PCA and the present invention also provides an anti-allergic composition comprising at least one member selected from the group consisting of the compounds selected from the compounds of formulas 1 to 6 and the soluble saccharides containing these compounds at their reducing ends as its active ingredient.

The anti-allergic composition is very useful for treating and preventing diseases which can be treated by inhibition of the type I allergic reaction, such as bronchial asthma, atopic dermatitis, allergic rhinitis, pollinosis, hives, contact dermatitis, allergic conjunctivitis and the like.

The above-mentioned pharmaceutical composition for treating or preventing diseases of the present invention, for example, the composition for inducing apoptosis, can be prepared by using at least one member selected from the group consisting of the compounds selected from the compounds of formula 1 to 6 and the soluble saccharides containing these compounds at their reducing ends as its active ingredient, and formulate it with a known pharmaceutically acceptable carrier.

In general, the compound is combined with a pharmaceutically acceptable liquid or solid carrier and, if necessary, to this is added solvent, dispersing agent, emulsifier, buffering agent, stabilizer, excipient, binder, disintegrant, lubricant and the like to obtain a preparation in the form of a solid preparation such as tablet, granule, powder, epipastic, capsule and the like, and a liquid preparation such as normal solution, suspension, emulsion and the like. In addition, a dried preparation which can be reconstituted as a liquid preparation by addition of a suitable carrier before use can be obtained.

The composition for inducing apoptosis of the present invention can be administrated as either an oral preparation or a parenteral preparation such as injectable preparation, drips or the like.

The pharmaceutical carrier can be selected according to the above-mentioned particular administration route and dosage form. For an oral preparation, for example, starch, lactose, sucrose, mannit, carboxymethylcellulose, cornstarch, inorganic salts and the like are used. For preparing the oral preparation, binder, disintegrant, surfactant, lubricant, fluidity promoting agent, tasting agent, coloring agent, flavoring agent and the like can also be added.

A parenteral preparation can be prepared according to conventional methods by dissolving or suspending the active ingredient of the present invention, that is the saccharide having the activity of inducing apoptosis, in a diluent such as injectable distilled water, physiological saline, aqueous glucose solution, injectable vegetable oil, sesame oil, peanut oil, soybean oil, corn oil, propylene glycol, polyethylene glycol or the like, and, if necessary, adding sterilizer, stabilizer, osmotic regulator, smoothing agent and the like to the resultant solution or suspension.

The composition for inducing apoptosis of the present invention can be administrated through a suitable route for the dosage form of the composition. The administration method is not limited and the composition can be used internally or externally (or topically) or by injection and the like. The injectable preparation can be administered intravenously, intramuscularly, subcutaneously, intradermally and the like. External preparations include a suppository and the like.

A dosage of the composition for inducing apoptosis of the present invention can be appropriately determined and varies depending on the particular dosage form, administration route and purpose as well as age, weight and conditions of a patient to be treated. In general, a daily dosage for an adult person is 10 µg to 200 mg/kg in terms of the amount of the active ingredient contained in the composition. As the dosage, of course, can vary dependent on various factors, in some cases, a less dosage than the above may be sufficient but, in other cases, a dosage more than the above may be required. The pharmaceutical composition of the present invention can be administrated orally as it is, or it can be administered daily by admixing with appropriate foods and drinks.

The carcinostatic composition of the present invention can be prepared by using at least one member selected from the group consisting of the compounds selected from the compounds of formulas 1 to 6 and the soluble saccharides containing these compounds at their reducing ends as its active ingredient and formulating it with a known pharmaceutical carrier. The carcinostatic composition can prepared according to the same manner as that described above with respect to the composition for inducing apoptosis.

The carcinostatic composition can be administrated through a suitable route for the dosage form of the composition. A method for administration is not limited and the composition can be administrated internally or externally (or topically) or by injection and the like. An injectable preparation can be administrated, for example, intravenously, intramuscularly, subcutaneously, intradermally and the like. External preparations include a suppository and the like.

A dosage of the carcinostatic composition of the present invention can be determined and varies depending on the particular dosage form, administration route and purpose as well as age, weight and conditions of a patient to be treated. In general, a daily dosage for an adult person is 10 µg to 200 mg/kg in terms of the amount of the active ingredient contained in the composition. As the dosage, of course, can vary dependent on various factors, in some cases, a less dosage than the above may be sufficient, but, in other cases, a dosage more than the above may be required. The pharmaceutical composition of the present invention can be administrated orally as it is, or it can be administrated daily by admixing with appropriate foods and drinks.

The antioxidant, the inhibitor of active oxygen production, the inhibitor of lipid peroxide radical production, the inhibitor of NO production, the immunoregulator and the anti-allergic composition of the present invention can be prepared according to the same manner as that described above with respect to the composition for inducing apoptosis. The same dosage and administration route as those described above with respect to the composition for inducing apoptosis can be used.

That is, the antioxidant, the inhibitor of active oxygen production, the inhibitor of lipid peroxide radical production, the inhibitor of NO production, the immunoregulator and the anti-allergic composition of the present invention are administrated through a suitable route for the particular dosage form of the composition. A method for administration is not limited and the composition can be administrated internally or externally, or by injection and the like. An injectable preparation can be administered intravenously, intramuscularly, subcutaneously, intradermally and the like. External preparations include a suppository and the like.

A dosage of the antioxidant, the inhibitor of active oxygen production, the inhibitor of lipid peroxide radical production, the inhibitor of NO production, the immunoregulator and the anti-allergic composition of the present invention can be determined and varies depending on the particular dosage form, administration route and purpose as well as age, weight and conditions of the patient to be treated. In general, a daily dosage for an adult person is 10 µg to 200 mg/kg in terms of the amount of the active ingredient contained in the composition. As the dosage, of course, can vary dependent on various factors, in some cases, a less dosage than the above may be sufficient, but, in other cases, a dosage more than the above may be required. The pharmaceutical composition of the present invention can be administrated orally as it is, or it can be administrated daily by admixing with appropriate foods and drinks.

The foods or drinks of the present invention are those comprising, produced by adding thereto and/or produced by diluting at least one member selected from the group consisting of the compounds selected from the compounds of formulas 1 to 6 and the soluble saccharides containing these compounds, for example, saccharides prepared by acid decomposition under acidic conditions below pH 7 and/or enzymatic digestion of the raw substances, such as agarobiose, agarotetraose, agarohexaose, agarooctaose, κ-carabiose, β-D-galactopyranosyl-3,6-anhydro-2-O-methyl-L-galactose and the like. Since the food or drink has an activity of inducing apoptosis, a carcinostatic activity, an antioxdant activity, an immunoregulatory activity and the like. Thus, it is very useful for ameliorating disease states of and preventing diseases sensitive to at least one member selected from the group consisting of the compounds selected from the compounds of formulas 1 to 6 and the soluble saccharides containing these compounds at their reducing ends, such as a disease that requires induction of apoptosis for its treatment or prevention, a carcinomatous disease, a disease that requires inhibition of active oxygen production for its treatment or prevention, a disease that requires inhibition of NO production for its treatment or prevention or a disease that requires immunoregulation for its treatment or prevention, an allergic disease and the like.

A process for producing the foods or drinks of the present invention is not limited to a specific one, and cooking, processing and other generally employed processes for producing foods and drinks can be used in so far as the resultant foods or drinks contain as their active ingredients at least one member selected from the group consisting of the compounds selected from the compounds of formulas 1 to 6 and the soluble saccharides containing those compounds at their reducing ends prepared, for example, by acid decomposition under acidic conditions below pH 7 and/or enzymatic digestion of the raw substances, such as agarobiose, agarotetraose, agarohexaose, agarooctaose, κ-carabiose, β-D-galactopyranosyl-3,6-anhydro-2-O-methyl-L-galactose and the like.

The foods or drinks of the present invention are not limited to a specific one and examples thereof include cereal processed products (e.g., wheat flour products, starch processed products, premixed products, noodles, macaroni, breads, bean jams, buckwheat noodles, fu (wheat gluten bread), rice noodle, gelatin noodles, and packed rice cake, etc.), fat and oil processed products (e.g., plastic fat and oil, tempura oil, salad oil, mayonnaise, dressings, etc.), soybean processed products (e.g., tofu, miso, fermented soybeans, etc.), meet processed products (e.g., hams, bacon, pressed ham, sausage, etc.), processed marine products (e.g., frozen ground fish meat, boiled fish paste, tubular roll of boiled fish paste, cake of ground fish, deep-fried patty of fish paste, fish ball, sinew, fish meat ham, sausage, dried bonito, processed fish egg products, canned marine food, fish boiled in sweetened soy sauce, etc.), dairy products (e.g., raw milk, cream, yogurt, butter, cheese, condensed milk, powdered milk, ice cream, etc.), processed vegetables and fruit products (e.g., pastes, jams, pickles, fruit juices, vegetable drinks, mixed drinks, etc.), confectioneries (e.g., chocolates, biscuits, sweet buns, cakes, rice-cake sweets, rice sweets, etc.), alcohol drinks (e.g., sake, Chinese liquors, wines, whiskies, shochu, vodkas, brandies, gins, rums, beer, soft alcohol drinks, fruit liquors, liqueurs, etc.), luxury drinks (e.g., green tea, tea, oolong tea, coffee, soft drinks, lactic acid drinks, etc.), seasonings (e.g., soy sauce, sauce, vinegar, sweet sake, etc.), canned food, bottled food and bagged food (e.g., various cooked food such as rice topped with cooked beef and vegetables, rice boiled together with meat and vegetables in a small pot, steamed rice with red beans, curry, etc.), semi-dried or condensed food (e.g., liver paste, the other spread, soup of buckwheat noodles or "udon", condensed soups, etc.), dried food (e.g., instant noodles, instant curry, instant coffee, powdered juice, powdered soup, instant miso soup, cooked food, cooked drinks, cooked soup, etc.), frozen food (e.g., sukiyaki, chawan-mushi, grilled eel, hamburger steak, shao-mai, Chinese meat dumpling, various stick, fruit cocktail, etc.), solid food, liquid food (e.g., soup, etc.), processed agricultural products and forest products such as spices, processed livestock products, processed marine products and the like.

In so far as the food or drink of the present invention comprises, is produced by adding thereto and/or produced by diluting at least one member selected from the group consisting of the compounds selected from the compounds of formulas 1 to 6 and the soluble saccharides containing these compounds at their reducing ends, for example, saccharides prepared by acid decomposition under acidic conditions below pH 7 and/or enzymatic digestion of the raw substances, such as agarobiose, agarotetraose, agarohexaose, agarooctaose, κ-carabiose, β-D-galactopyranosyl-3,6-anhydro-2-O-methyl-L-galactose and the like, in an amount necessary for exhibiting the physiological functions, their forms are not limited to a specific one and may be any edible forms including tablets, granule, capsule and the like.

3,6-Anhydrogalactopyranose, a 2-O-methylated derivative thereof and the saccharides containing these compounds at their reducing ends tend to open at their hemi-acetal rings to form aldehyde groups at the ends. These aldehyde groups as well as the aldehyde group of the aldehyde of the 3,6-anhydrogalactopyranose tend to react with compounds which are reactive with aldehyde group, for example, nucleophiles such as amino acids. The compounds of formulas 1 to 6 or the saccharides, for example, the oligosaccharides thus reacted are in such a state that they lose the compounds selected from the compounds of formulas 1 to 6 at their reducing ends. Therefore, they lose various physiological activities of the member selected from the compounds selected from the compounds of formulas 1 to 6 and the oligosaccharides containing these compounds at their reducing ends. That is, in order to maintain the member selected from the compounds selected from the compounds of formulas 1 to 6 and the saccharides containing these compounds at their reducing ends in the foods or drinks stably, a molar concentration of a compound reactive with the aldehyde should be kept lower than that of the aldehyde.

In the production of the food or drink of the present invention, it is possible to provide the food or drink that contains the member selected from the group consisting of the compounds selected from the compounds of formulas 1 to 6 and the oligosaccharides containing these compounds at their reducing ends in a high content without substantial reduction of the amount thereof by controlling the amount of a compound that is reactive with the aldehyde. Such control has not been considered heretofore in the prior art.

It is also found that the member selected from the group consisting of the compounds selected from the compounds of formula 1 to 6 and the saccharides containing these compounds at their reducing ends is stable under acidic conditions. Then, an acidic food or acidic drink which contains at least one member selected from the group consisting of the compounds selected from the compounds of formulas 1 to 6 and soluble saccharide containing these compounds at their reducing ends in a high content can be provided by carrying out all of the steps of producing the food or drink of the present invention under acidic conditions to prepare the acidic food or acidic drink.

In the production of the acidic food or drink of the present invention, the kind of the acid to be used for acid decomposition of the raw substances is not limited to a specific one, and both organic and inorganic acids can be used. However, a better taste of the resultant acid decomposition product of agar is obtained when an organic acid are used. Then, organic acids are preferably used to obtain an acid decomposition product having a novel flavor. The organic acid can be selected depending on the particular purpose. It can be used alone, or two or more of them can be used in combination. Preferred examples of the organic acids include acetic acid, citric acid, malic acid, lactic acid, tartaric acid, succinic acid, fumaric acid and the like. Decomposition conditions are not specifically limited. For example, when citric acid is used as the organic acid, acid decomposition of agar as a raw substance is carried out at 60 to 130 C, preferably 90 to 105 C, for 3 to 300 minutes, preferably 30 to 200 minutes, thereby modifying an acidic taste of the organic acid to obtain the composition having a good balanced taste, mild texture and a smooth acidic taste. An acidulant having the desired acidic taste can be obtained by heat treatment of a composition containing 0.05 to 30% by weight, preferably 0.2 to 10% by weight of an organic acid, and 1 to 20% by weight, preferably 5 to 15% by weight of at least one member selected from the group consisting of the compounds selected from the compounds of formulas 1 to 6 and the soluble saccharides containing these compounds at their reducing ends. The acidulant thus obtained is very useful for the production of soft drinks, acidic seasonings, acidic foods and the like.

The acidic food or acidic drink of the present invention contains a large amount of at least one member, which has a physiological activity, selected from the group consisting of the compounds selected from the compounds of formulas 1 to 6 and the soluble saccharides containing these compounds, for example, saccharides prepared by acid decomposition under acidic conditions below pH 7 and/or enzymatic digestion of the raw substances, such as agarobiose, agarotetraose, agarohexaose, agarooctaose, κ-carabiose, β-D-galactopyranosyl-3,6-anhydro-2-O-methyl-L-galactose and the like. The physiological functions of the compounds such as an activity of inducing apoptosis, a carcinostatic activity and the like provide an effect of preventing carcinogenesis, an effect of suppressing cancer or the like upon eating the food or drink. That is, the acidic food or acidic drink of the present invention is a healthy food or drink which has effects of ameliorating the disease states of or preventing the diseases sensitive to at least one member selected from the group consisting of the compounds selected from the compounds of formulas 1 to 6 and the soluble saccharides containing these compounds, and is particularly useful for keeping gastrointestinal health.

The compounds selected from the compounds of formulas 1 to 6 and the soluble saccharides containing said compounds of the present invention, for example, saccharides prepared by acid decomposition under acidic conditions below pH 7 and/or enzymatic digestion of the raw substances, such as agarobiose, agarotetraose, agarohexaose, agarooctaose, κ-carabiose, β-D-galactopyranosyl-3,6-anhydro-2-O-methyl-L-galactose and the like have antioxidant activities such as an activity of inhibiting active oxygen production, an activity of inhibiting lipid peroxide radical production and the like, and can be used in the production antioxidant foods or antioxidant drinks as an antioxidant such as an inhibitor of active oxygen production, an inhibitor of lipid peroxide radical production, an inhibitor of NO production and the like.

That is, according to the present invention, there is provided an antioxidant, in particular, an antioxidant for foods and drinks, which comprises at least one member selected from the group consisting of the compounds selected from the compounds of formulas 1 to 6 and the soluble saccharides containing these compounds as its active ingredient.

The form of the antioxidant of the present invention is not limited to a specific one, and can be suitably selected according to the foods and drinks to be applied, for example, powder, paste, emulsion and the like. The antioxidant food or drink which comprises the member selected from the compounds and the saccharides used in the present invention as its active ingredient can be readily and simply produced by using the antioxidant of the present invention.

According to the present invention, there is also provided a saccharide for an antioxidant selected from the group consisting of the compounds selected from the compounds of formulas 1 to 6 and the soluble saccharide containing these compounds. For example, the saccharide for an antioxidant can be obtained as a product produced by acid decomposed under acidic conditions below pH 7 and/or enzymatic digestion of the raw substance. In addition, its purified or partial purified product can also be used. Examples of the raw substances include those derived from red algae such as agar, agarose, carrageenan and the like. They can be used alone or two or more of them can be used in combination. The examples of representative saccharides for an antioxidant are, not limited specifically, soluble polysaccharides containing the compounds selected from the compound of formulas 1 to 6, for example, agarobiose, agarotetraose, agarohexaose, agarooctaose, κ-carabiose and β-D-galactopyranosyl-3,6-anhydro-2-O-methyl-L-galactose and the like.

The saccharide for an antioxidant of the present invention is useful for eliminating or suppressing the production of oxidants in a living body, such as active oxygen. Then, the saccharide for an antioxidant is useful for ameliorating disease states of or preventing diseases caused by production or excess of active oxygen.

As described above, oxidative stress, which is generated from oxidative damage of a living body in case where the system for producing active oxygen is predominant over an elimination system, is involved in various diseases. Thus, a living body is always exposed to circumstances which lead to diseases caused by oxidative stress or worsening of the diseases conditions. Therefore, it is desirable to take a suitable amount of an antioxidant everyday for preventing, treating or preventing worsening of diseases caused by oxidative stress. For daily intake of suitable amount of an antioxidant, it is desirable to take it from foods and drinks. The foods and drinks of the present invention which comprise, produced by adding thereto, and/or produced by adding the saccharide for an antioxidant are very useful for antioxidant foods or drinks or anti-oxidative stress foods or drinks.

The member selected from the compounds and the saccharides used in the present invention also have ability of retaining water and at least one of them can be used as an active ingredient for the production of an anti-constipation composition, an anti-constipation food and an anti-constipation drink.

Furthermore, according to the present invention, there is provided a cosmetic composition which comprises as its active ingredient the soluble saccharide containing the compound selected from the compounds of formulas 1 to 6 in its reducing end, for example, an oligosaccharide such as agarobiose, agarotetraose, agarohexaose, agarooctaose, κ-carabiose, β-D-galactopyranosyl-3,6-anhydro-2-O-methyl-L-galactose or the like. The saccharide can be obtained as a product produced by acid decomposition under acidic conditions below pH 7 and/or enzymatic digestion of the raw substance. The purified or partially purified decomposition product can also be used. As the raw substance, that derived from red algae, for example, agar, agarose, carrageenan or the like can be used alone or two or more of them can be used in combination.

The above-mentioned compound can be used as an active ingredient for the production of cosmetic compositions including fundamental cosmetic compositions such as cream, milky lotion, lotion, facial cleansing and puck, makeup cosmetics such as lipstick and foundation, body soap, soap and the like. The compound is also effective to the hair and the cosmetic composition of the present invention can be produced in the form of hair care products, for example, hair products such as hair tonic, hair liquid, hair set lotion, hair blow agent, hair cream, hair coat, and the like and hair toiletry products such as shampoo, hair rinse, hair treatment, and the like. The amount of the compound mixed in the cosmetic composition can be determined appropriately according to its skin beautifying/whitening activity, humectant or moisturizing activity, antioxidant activity and the like. As other cosmetic components, those mixed in conventional cosmetic compositions can be used. Skin beautifying/whitening activity and humectant or moisturizing activity can be measured by conventional methods, for example the method described in JP-A 8-310937.

The cosmetic composition of the present invention has excellent properties based on a skin beautifying/whitening activity, a humectant or moisturizing activity, an antioxidant activity, an activity of inhibiting active oxygen production and an anti-oxidative stress activity to the skin; a humectant or moisturizing activity, an antioxidant activity, an activity of inhibiting active oxygen production and an anti-oxidative stress activity to the hair; and the like.

The present invention also provides a preservative composition for keeping freshness of foods and drinks which comprises as its active ingredient at least one member selected from the group consisting of the compounds selected from the compounds of formulas 1 to 6 and the soluble saccharides containing these compounds at their reducing ends, for example, oligosaccharides such as agarobiose, agarotetraose, agarohexaose, agarooctaose, κ-carabiose, β-D-galactopyranosyl-3,6-anhydro-2-O-methyl-L-galactose and the like. The saccharide can be obtained as a product produced by acid decomposion under acidic conditions below pH 7 and/or enzymatic digestion of the substance. The purified or partially purified decomposition product also can be used. As the raw substance, that derived from red algae which comprises the compound selected from the compounds of fomulas 1 to 6, for example, agar, agarose, carrageenan and the like can be used alone or two or more can be used in combination.

At least one member selected from the group consisting of the compounds selected from the compounds of formulas 1 to 6 and the soluble saccharides containing the compounds at their reducing ends, for example, a saccharide such as agarobiose, agarotetraose, agarohexaose, agarooctaose, κ-carabiose, β-D-galactopyranosyl-3,6-anhydro-2-O-methyl-L-galactose and the like has an antioxidant activity, a freshness keeping activity and a tyrosinase inhibitory activity. The preservative composition for keeping freshness of foods and drinks of the present invention which prevents effectively color change, decay, oxidation and the like of foods can be produced by using the compound as its active ingredient according to a known formulation process. The preservative composition of the present invention is very useful for keeping a flavor and freshness of various foods, perishable foods, and processed foods.

No acute toxicity is observed when administering either of the member selected from the group consisting of the compounds selected from the compounds of formula 1 to 6 and the soluble saccharides containing these compounds used in the present invention to a mouse at a dosage of 1 g/kg orally or intraperitoneally.

The following examples further illustrate the present invention in detail but are not to be construed to limit the scope thereof.

EXAMPLE 1

(1) A suspension of 400 mg of commercially available agar powder (manufactured by Wako Pure Chemical Industries, Ltd.) in 20 ml of 1 N HCl was heated with a microwave oven to obtain a solution. The resulting solution was cooled and was adjusted to pH 4 with sodium hydroxide. To the solution was added 384 mg of citric acid and the solution was adjusted to pH 3 with sodium hydroxide. Water was added thereto to make the total volume up to 40 ml and the solution was heated at 120 C for 4 hours. The resulting acid decomposition solution was adjusted to pH 6.5 with sodium hydroxide and filtrated with a 0.2 µm filter (manufactured by Corning).

Human promyelocytic leukemia cell HL-60 (ATCC CCL-240) was incubated at 37 C in RPMI 1640 medium (manufactured by Gibco) supplemented with 10% of fetal bovine serum (JRH Bioscience) which had been treated at 56 C for 30 minutes, and suspended in the same medium at a concentration of 500 cells/90 µl. Each 90 µl portion of the suspension was distributed into each well of a 96 well plate (manufactured by Falcon). To the suspension in each well was added 10 µl of the above-mentioned acid decomposition solution, a 10-fold dilution of the solution or water, and incubated with 5% $CO_2$ at 37 C. After 24 hour and 48 hour from the initiation of the incubation, the cell morphology was observed under an optical microscope. Then, according to the MTT method described in "Apoptosis Jikken Protocol" (Syuzyun-sha, Tanuma, Seiichi ed., pp. 156 (1994)), 5 mg/ml of 3-(4,5-dimethylthiazole-2-yl)-2,5-diphenyltetrazolium bromide (manufactured by Sigma) and 10 µl of phosphate buffered saline solution were added to the culture and the incubation was continued for additional 4 hours. Then, 100 µl of 2-propanol containing 0.04 N hydrochloric acid was added to the culture, and the mixture was thoroughly stirred. An absorbance at 590 nm was measured and the number of viable cells was calculated from the absorbance measured for each of the wells, which was compared each other.

EXAMPLE 2

(1) A suspension of 1 g of commercially available agar (Agar Noble, manufactured by Difco) in 100 ml of 0.1 N hydrochloric acid was heated with a microwave oven until boiling to prepare a solution. After cooling to room temperature and adjusting to pH 6, the solution was filtered through Cosmonice filter (manufactured by Nacalai Tesque) and 2 ml of the filtrate was separated with reverse phase HPLC under the following conditions.

Column: TSK-gel ODS 80Ts (20 mm×250 mm, manufactured by Toso)
TSK guard column ODS-80Ts 20 mm×50 mm, manufactured by Toso)
Mobile phase: aqueous 0.1% trifluoroacetic acid (TFA) solution
Flow rate: 9 ml/min
Detection: absorbance at 215 nm Each elution peak was fractionated, collected, evaporated to dryness under reduced pressure and then dissolved in 300 µl of water. Each fraction was sterilized by filtration and its 10 µl portion was placed in a well of a 96 well microtiter plate. Then, 90 µl of RPMI 1640 medium (manufactured by Nissui) containing 10% fetal bovine serum (manufactured by Gibco) and 5,000 HL-60 cells (ATCC CCL-240) was added thereto, followed by incubation at 37 C for 48 hours with 5% $CO_2$. The cell morphology was observed under an optical microscope. Then, 5 mg/ml 3-(4,5-dimethylthiazole-2-yl)-2,5-diphenyltetrazolium bromide and 10 µl of phosphate buffered saline solution were added thereto and the incubation was continued for additional 4 hours. To the culture was added 100 µl of 2-propanol containing 0.04 N hydrochloric acid and the resultant mixture was thoroughly stirred. The absorbance at 590 nm was measured to determine a cell proliferation rate.

As a result, apoptosis corpuscles were observed in the group to which the fraction from the peak at 8.26 min. was added. And, as compared with the control group to which water was added, the absorbance at 590 nm was lower and the cell proliferation was inhibited.

(2) A 100 µl of the fraction from the peak at 8.26 min. described in Example 2-(1) was separated with size exclusion HPLC chromatography as follows.

Figure 3:
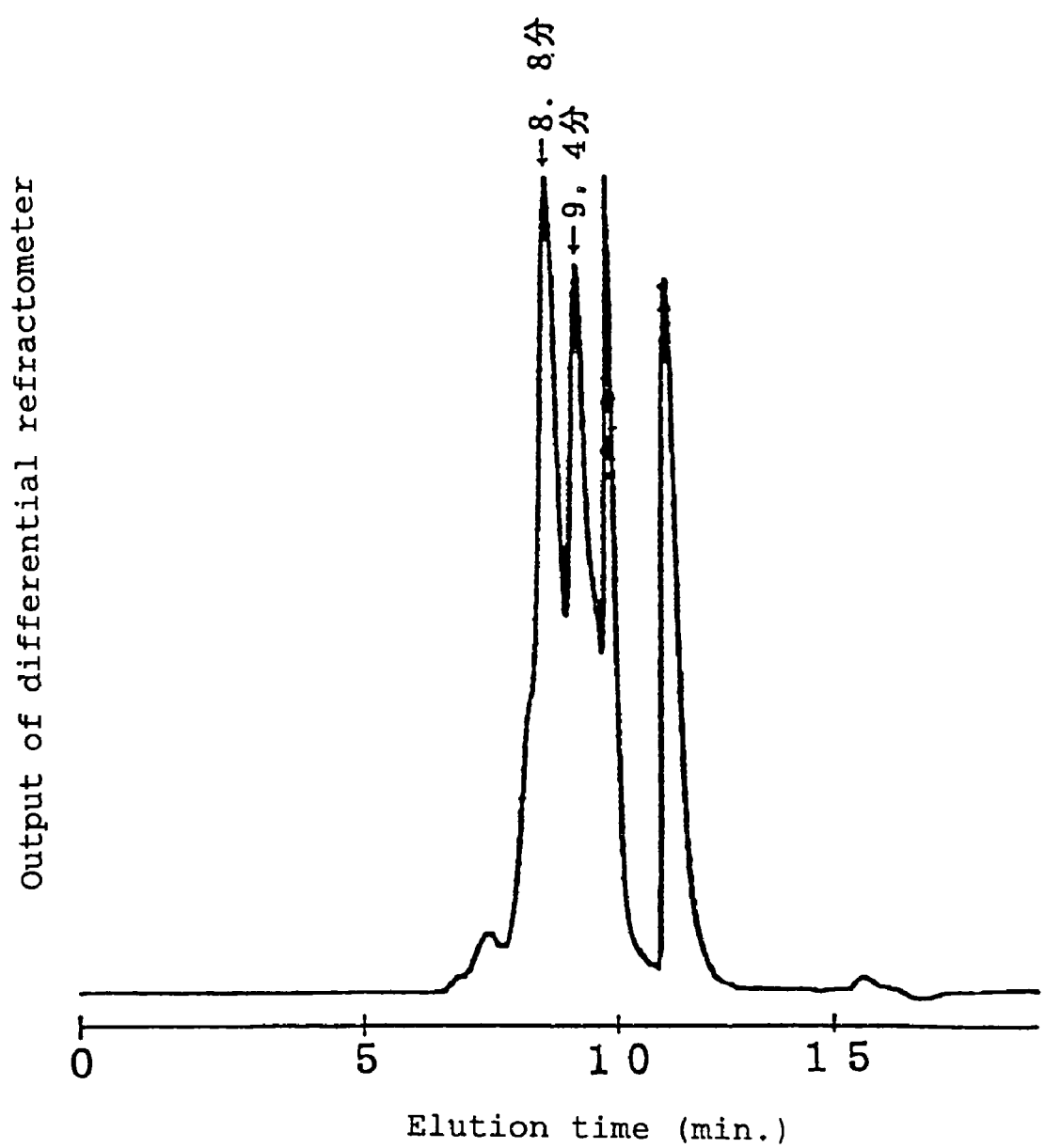
FIG. 3 illustrates a size-exclusion HPLC chromatogram of agar decomposed with an acid.

Column: TSK-gel α-2500 (7.8 mm×300 mm, manufactured by Toso)
TSK guard column α (6 mm×40 mm, manufactured by Toso)
Mobile phase: aqueous 0.01% TFA solution
Flow rate: 0.8 ml/min
Detection: differential refractometer The separation pattern of the size exclusion HPLC chromatography is illustrated in FIG. 3. That is, FIG. 3 illustrates the size exclusion HPLC chromatogram of the acid decomposition product of agar. The horizontal axis represents the elution time (min.) and the vertical axis represents the output from the differential refractometer.

Each separated peak was fractionated, collected and evaporated to dryness under reduced pressure. Each fraction was dissolved in water at a concentration of 10 mg/ml, sterilized by filtration and then, according to the same manner as that described above in Example 2-(1), an apoptosis-inducing activity and an antiproliferation activity against tumor cell were measured. As a result, the peaks at the elution time 8.87 min. and 9.40 min. had both activities.

The substances at the elution time 8.87 min. and 9.40 min. were separately dissolved in a phosphate buffered saline solution, and allowed to stand at 37 C for 1 hour. Then, according to the same manner as that described above, they were analyzed by the size exclusion HPLC chromatography. As a result, the peaks at 8.87 min. and 9.40 min. were observed in both samples, and the ratio of the peak area was almost identical among the samples. This revealed that the substances at the elution time 8.87 min. and 9.40 min. were in an equilibrium state when they were dissolved in the aqueous phosphate buffer.

The fractions from the peaks at the elution time 8.87 min. and 9.40 min. were combined and evaporated to dryness under reduced pressure to obtain an apoptosis-inducing and carcinostatic substance.

(3) The apoptosis-inducing and carcinostatic substance described in Example 2-(2) was subjected to mass spectrometry with DX302 mass spectrometer (manufactured by Nippon Denshi). The measurement was carried out by using glycerol as a matrix with negative ion mode.

FAB-MS
m/z 323 $[M-H]^-$
415 $[M+glycerol-H]^-$
507 $[M+2glycerol-H]^-$

Figure 4:
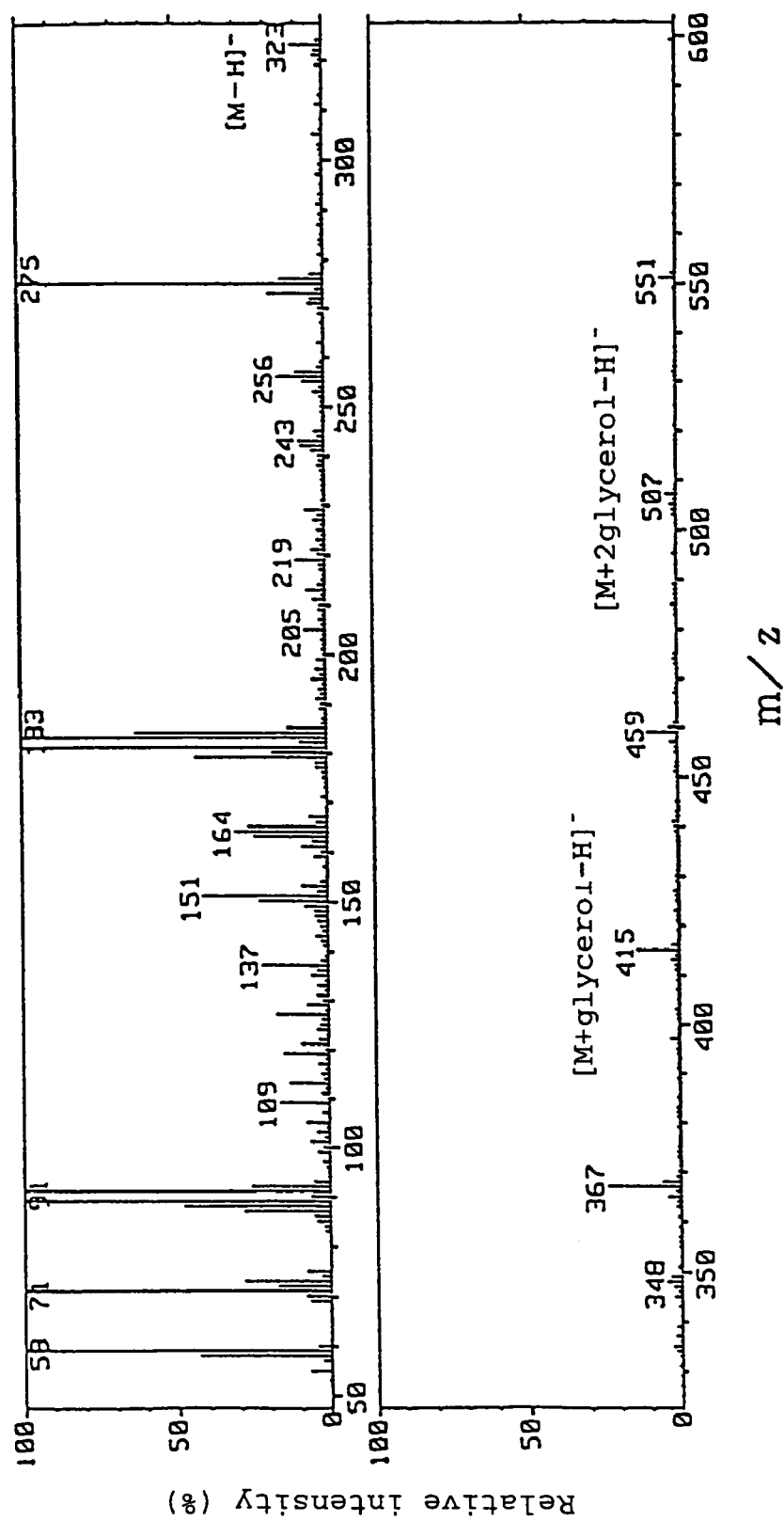
FIG. 4 illustrates a mass spectrum of an apoptosis-inducing and carcinostatic substance.

The results are shown in FIG. 4. That is, FIG. 4 illustrates the mass spectrum of the apoptosis-inducing and carcinostatic substance. The horizontal axis represents m/z value and the vertical axis represents the relative intensity (%).

Nuclear magnetic resonance spectrum of the apoptosis-inducing and carcinostatic substance described in Example 2-(2) was measured with JNM-A500 nuclear magnetic resonance apparatus (manufactured by Nippon Denshi).

$^1$H-NMR: δ 3.36 (1H, dd, J=8.0, 10.0 Hz), 3.51 (1H, dd, J=3.0, 10.0 Hz), 3.56 (1H, m), 3.58 (1H, m), 3.63 (1H, m), 3.67 (1H, m), 3.70 (1H, dd, J=3.0, 10.0 Hz), 3.77 (1H, d, J=3.0 Hz, 3.83 (1H, dd, J=4.5, 10.0 Hz), 3.93 (1H, dd, J=5.0, 3.5 Hz), 4.23 (1H, m), 4.25 (1H, m), 4.41 (1H, d, J=8.0 Hz), 4.85 (1H, d, J=6.0 Hz)

The sample was dissolved in heavy water and the chemical shift value of HOD was shown as 4.65 ppm.

$^{13}$C-NMR: δ 61.9, 69.4, 71.5, 73.37, 73.42, 73.8, 76.0, 76.1, 83.7, 86.5, 90.7, 103.3

The sample was dissolved in heavy water and the chemical shift value of dioxane was shown as 67.4 ppm.

Figure 5:
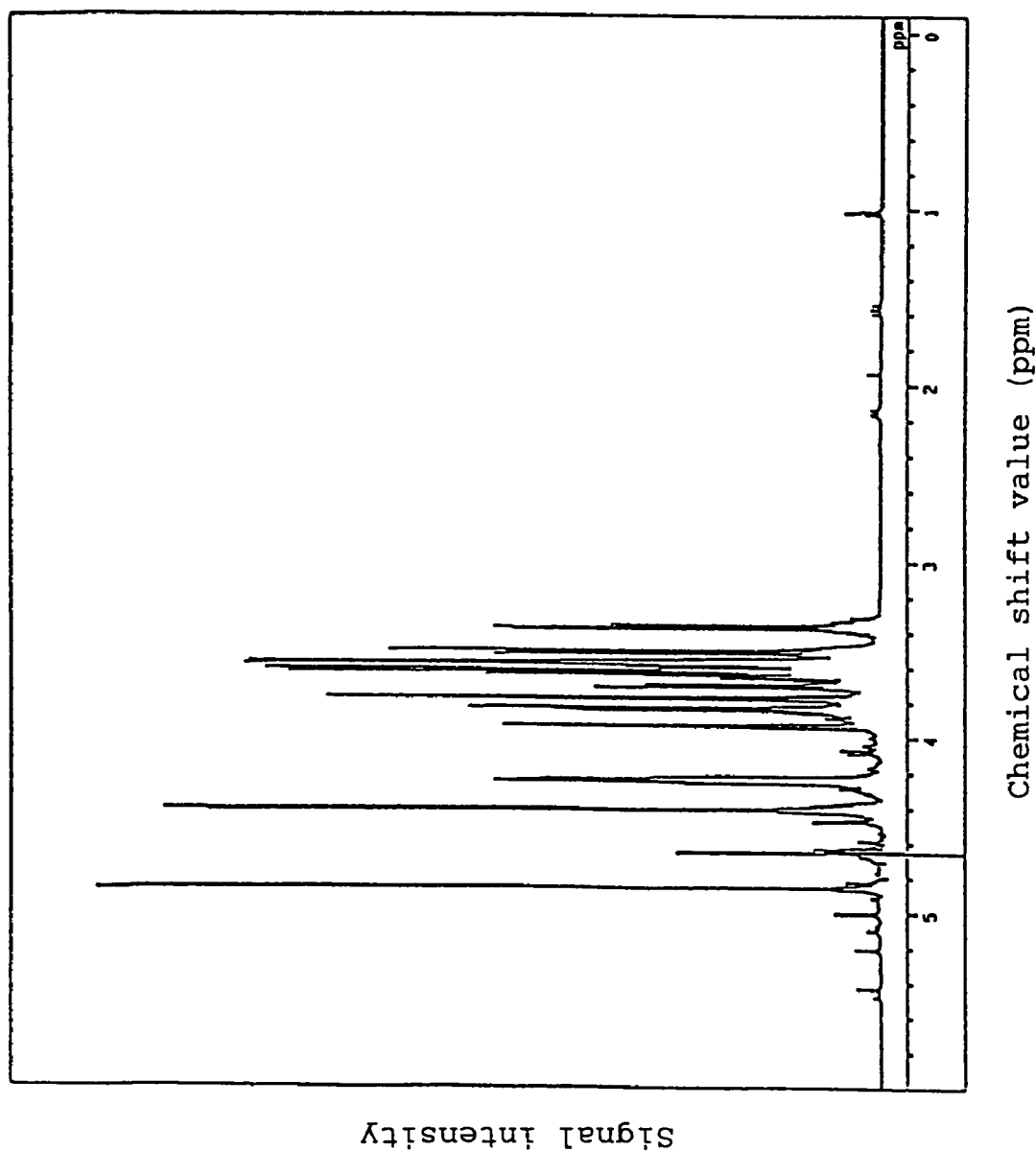
FIG. 5 illustrates a $^1$H-NMR spectrum of an apoptosis-inducing and carcinostatic substance (hydrate form).

$^1$H-NMR spectrum of the apoptosis-inducing and carcinostatic substance is shown in FIG. 5. In FIG. 5, the horizontal axis represents the chemical shift value (ppm) and the vertical axis represents the signal intensity. The sample was also dissolved in heavy dimethyl sulfoxide and $^1$H-NMR spectrum was measured.

$^1$H-NMR: δ 9.60 (1H, H of aldehyde)

Figure 6:
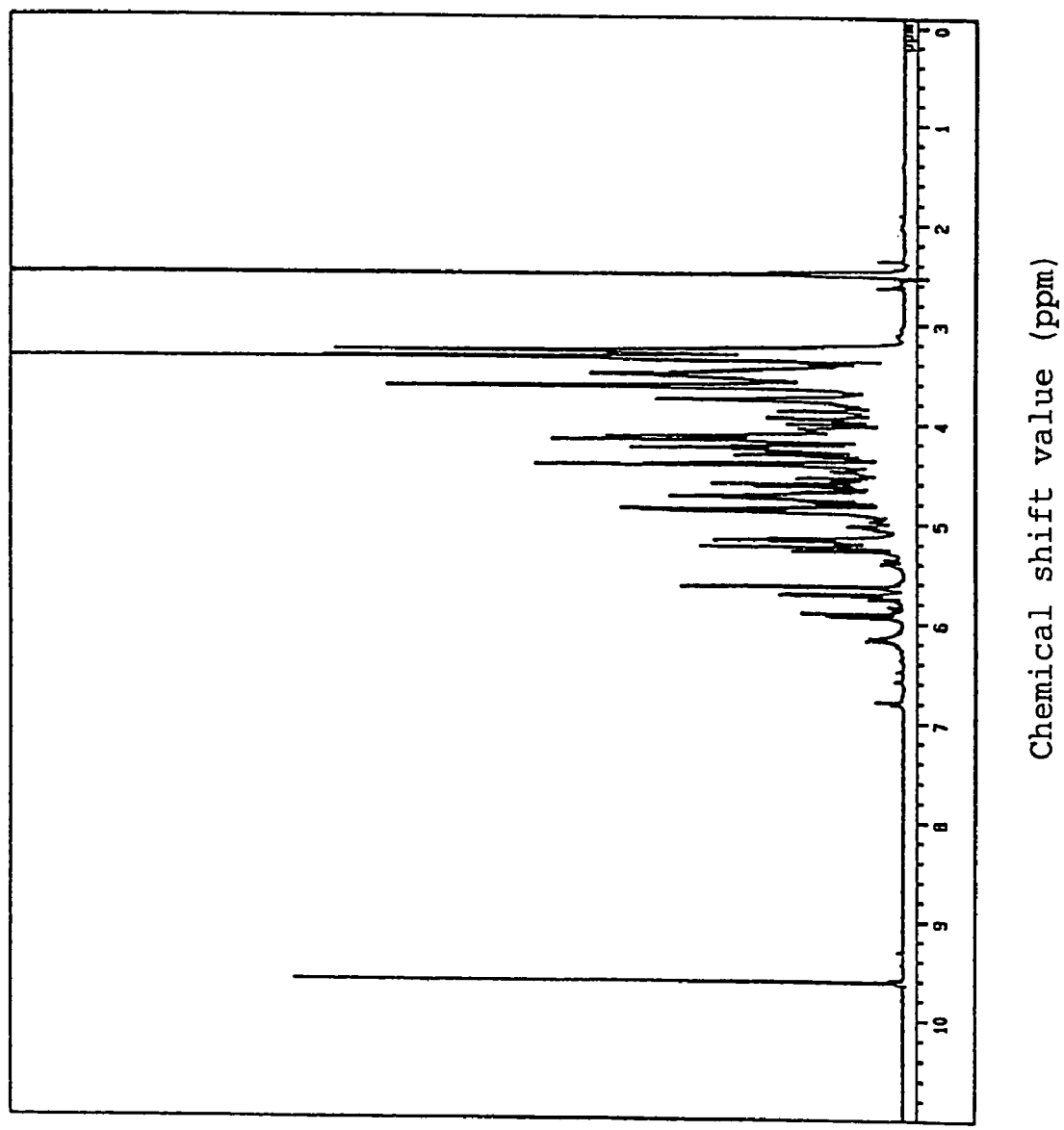
FIG. 6 illustrates a $^1$H-NMR spectrum of an apoptosis-inducing and carcinostatic substance (aldehyde form).

$^1$H-NMR spectrum of the apoptosis-inducing and carcinostatic substance in heavy dimethyl sulfoxide solvent is shown in FIG. 6. In FIG. 6, the horizontal axis represents the chemical shift value (ppm) and the vertical axis represents the signal intensity.

The apoptosis-inducing and carcinostatic substance described in Example 2-(2) was identified as agarobiose on the basis of the analytical results of mass spectrometry, $^1$H-NMR and $^{13}$C-NMR. And, the $^1$H-NMR in heavy dimethyl sulfoxide solvent demonstrated that 3,6-anhydrogactose at the reducing end of agarobiose was mainly present as an aldehyde whose ring was opened in a non-aqueous solvent. In addition, $^1$H-NMR in heavy water solvent demonstrated that it was present as a hydrated of the aldehyde in an aqueous solution.

The results as described above revealed that the apoptosis-inducing and carcinostatic substance obtained in Example 2-(2) was agarobiose.

(4) The apoptosis-inducing and carcinostatic substance obtained in Example 2-(2), i.e., agarobiose, was dissolved in water at a concentration of 0.78 mg/ml, and its 10 µl portion was placed in the well of a 96 well microtiter plate to measure an apoptosis-inducing activity and an antiproliferation activity against cell according to the same manner as described in Example 2-(1). As a result, apoptosis corpuscles were observed under an optical microscope and, as compared with the control group to which water as added, cell proliferation was suppressed by about 86% in the group to which agarobiose was added. Namely, agarobiose at a concentration of 78 µg/ml induced apoptosis in HL-60 cells and inhibited cell proliferation.

EXAMPLE 3

(1) A suspension of 2.5 g of commercially available agar (Agar Noble) in 50 ml of 0.1 N HCl was heated at 100 C for 13 minutes to prepare a solution. After cooling to room temperature and neutralizing to about neutral pH with NaOH, the solution was filtered through Cosmonice filter and separated with normal phase HPLC as follows.

Column: TSk-gel Amide-80 (21.5 mm×300 mm, manufactured by Toso)
Solvent A: aqueous 90% acetonitrile solution
Solvent B: aqueous 50% acetonitrile solution
Flow rate: 5 ml/min
Elution: linear gradient from solvent A to solvent B (80 min.) Solvent B (20 min.)
Detection: absorbance at 195 nm
Amount of sample applied: 2 ml The peaks at the retention time 66.7 min., 78.5 min. and 85.5 min. were fractionated and collected and they were subjected to mass spectrometry. As a result, these substances were agarobiose, agarotetraose and agarohexaose, respectively. The separation with HPLC as described above was repeated 8 times and the fractions thus separated were evaporated to dryness under reduced pressure to obtain 122 mg of agarobiose, 111 mg of agarotetraose, and 55 mg of agarohexaose, respectively.

Figure 7:
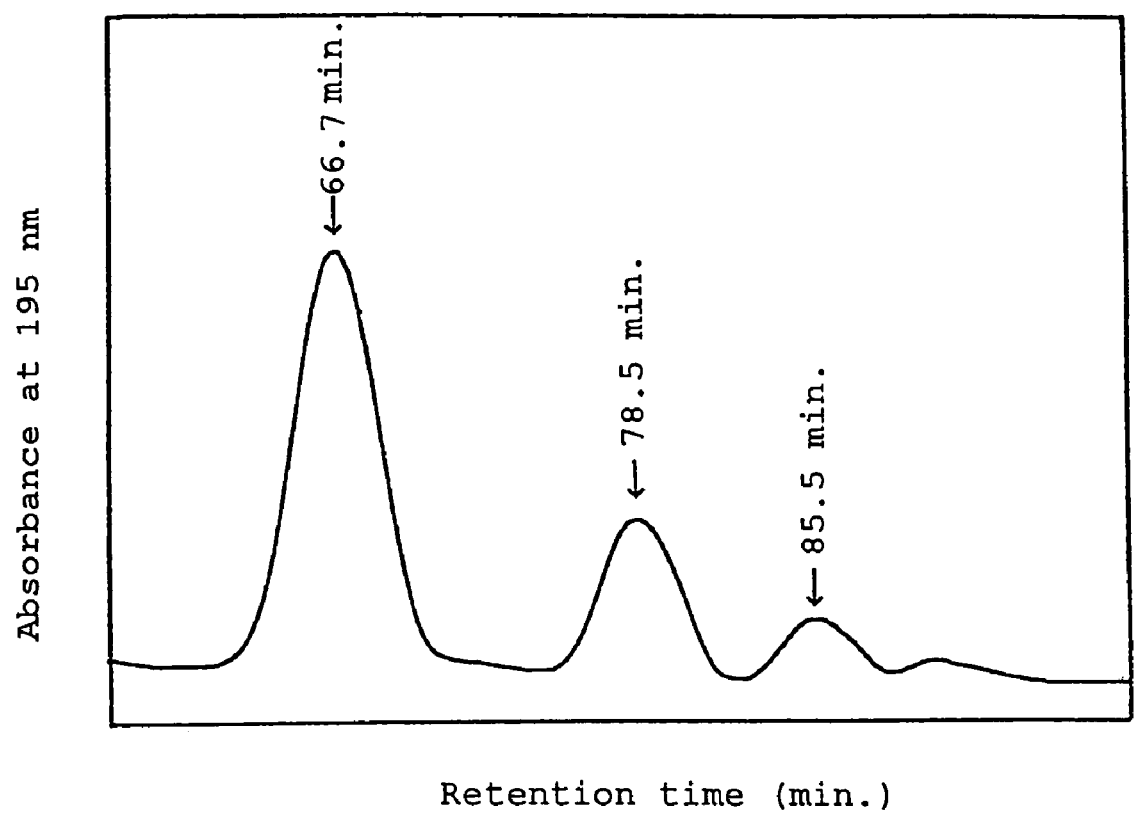
FIG. 7 illustrates an elution pattern of normal phase HPLC of agarobiose, agarotetraose and agarohexaose.
Figure 8:
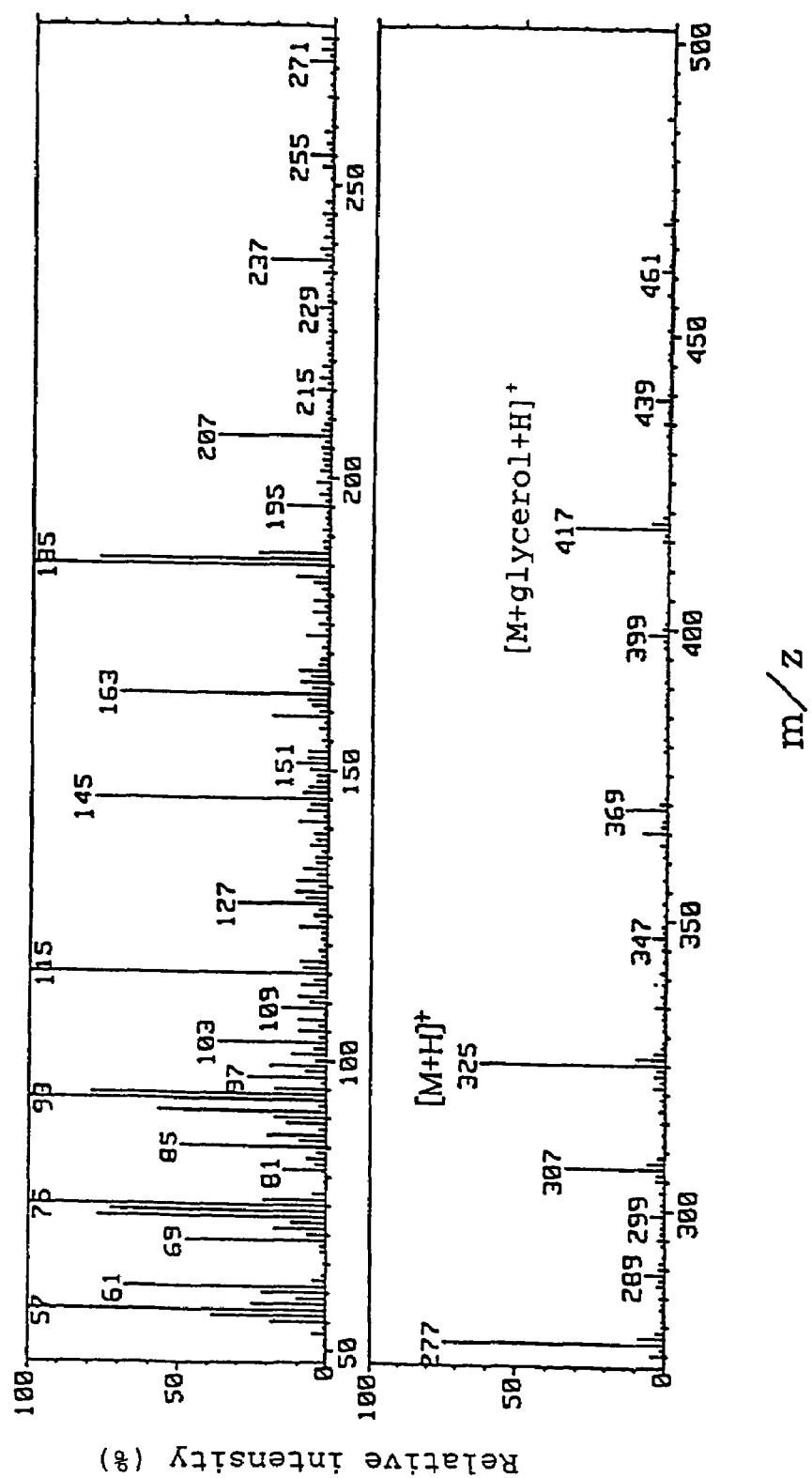
FIG. 8 illustrates a mass spectrum of the peak at 66.7 min.
Figure 9:
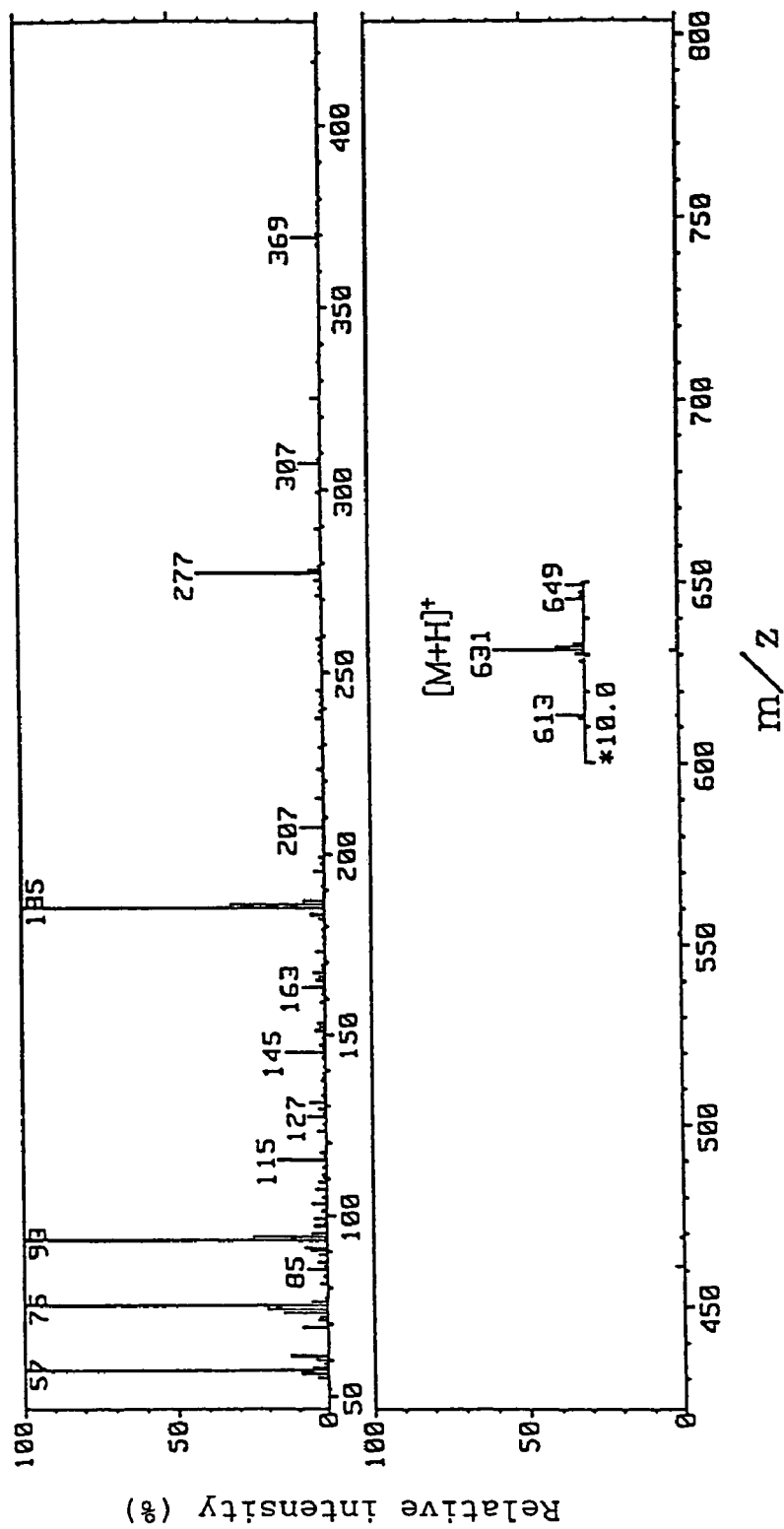
FIG. 9 illustrates a mass spectrum of the peak at 78.5 min.
Figure 10:
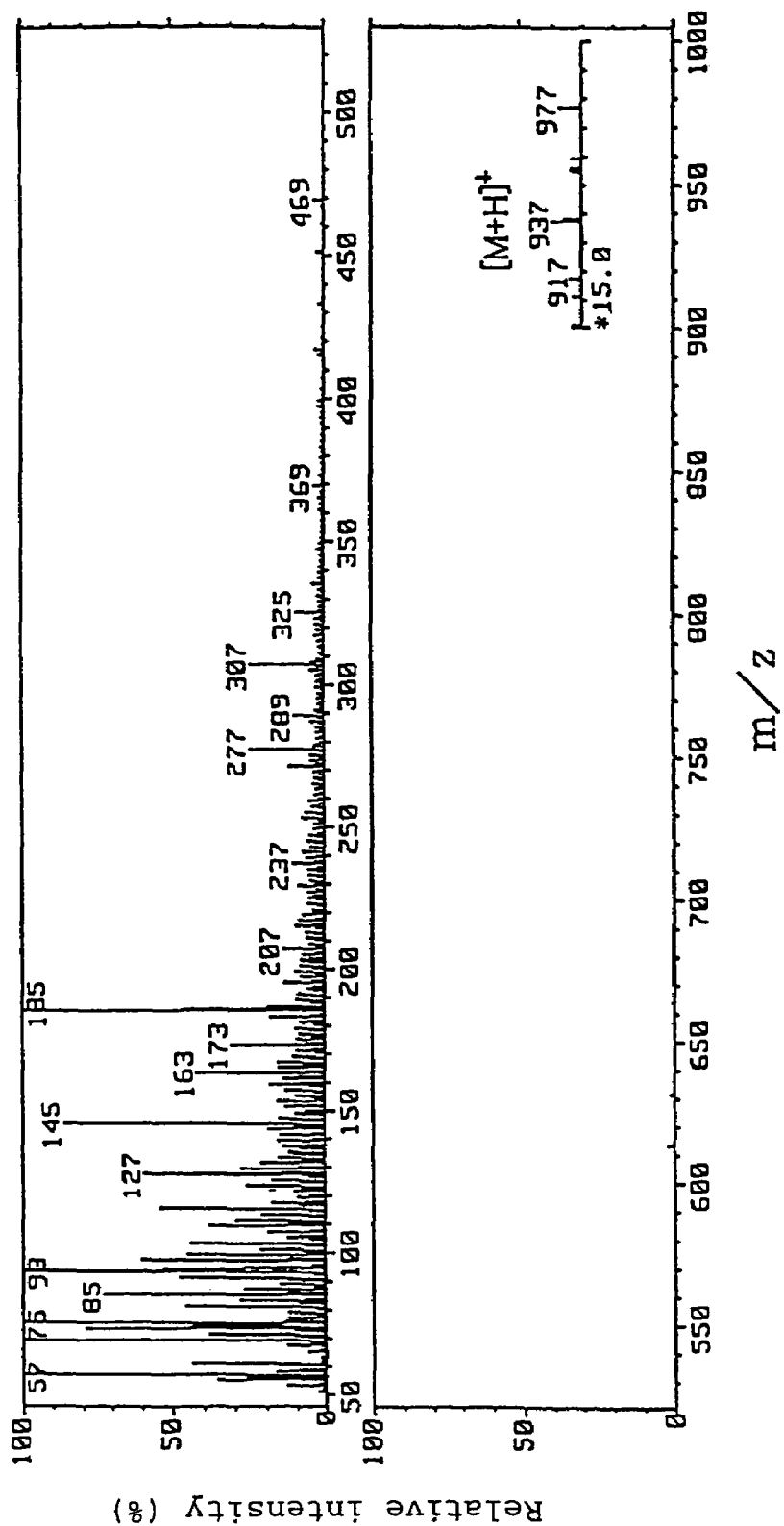
FIG. 10 illustrates a mass spectrum of the peak at 85.5 min.

The results are shown in FIGS. 7 to 10. That is, FIG. 7 illustrates the elution pattern of agarobiose, agarotetraose and agarohexaose in the normal phase HPLC. The horizontal axis represents the retention time (min.) and the vertical axis represents the absorbance at 195 nm. FIG. 8 illustrates the mass spectrum of the peak at 66.7 min. The horizontal axis represents the m/z value and the vertical axis represents the relative intensity (%). FIG. 9 illustrates the mass spectrum of the peak at 78.5 min. The horizontal axis represents the m/z value and the vertical axis represents the relative intensity (%). FIG. 10 illustrates the mass spectrum of the peak at 88.5 min. The horizontal axis represents the m/z value and the vertical axis represents the relative intensity (%).

(2) To 450 μl of 100 mM aqueous agarobiose solution obtained in Example 3-(1) were added 50 μl of 10-fold concentrated phosphate buffered saline (T900, manufactured by Takara Shuzo) and 50 μl of 10 units/μl of β-galactosidase (G5635, manufactured by Sigma) in phosphate buffered saline. The resultant mixture was incubated at 37 C for 1 hours.

To the reaction mixture was added 5 ml of a mixture of 1-butanol:ethanol=1:1 and then insoluble materials were removed by centrifugation. The resultant solution was applied on silica gel BW-300SP for column chromatography (3×50 cm, manufactured by Fuji Silysia Chemical Ltd.) and separated using 1-butanol:ethanol:water=5:5:1 as the eluent with pressurizing at 0.3 kg/cm$^2$ with a compressor. Fractionation was carried out to collect 7 ml fractions, and a portion of each fraction was taken up and analyzed with thin layer chromatography. As a result, Fraction Nos. 14 to 17 contained 3,6-anhydro-L-galactose with high purity. These fractions were combined and evaporated to dryness under reduced pressure to obtain 3.8 mg of 3,6-anhydro-L-galactose. The structure of this substance was confirmed by mass spectrometry and nuclear magnetic resonance.

Figure 11:
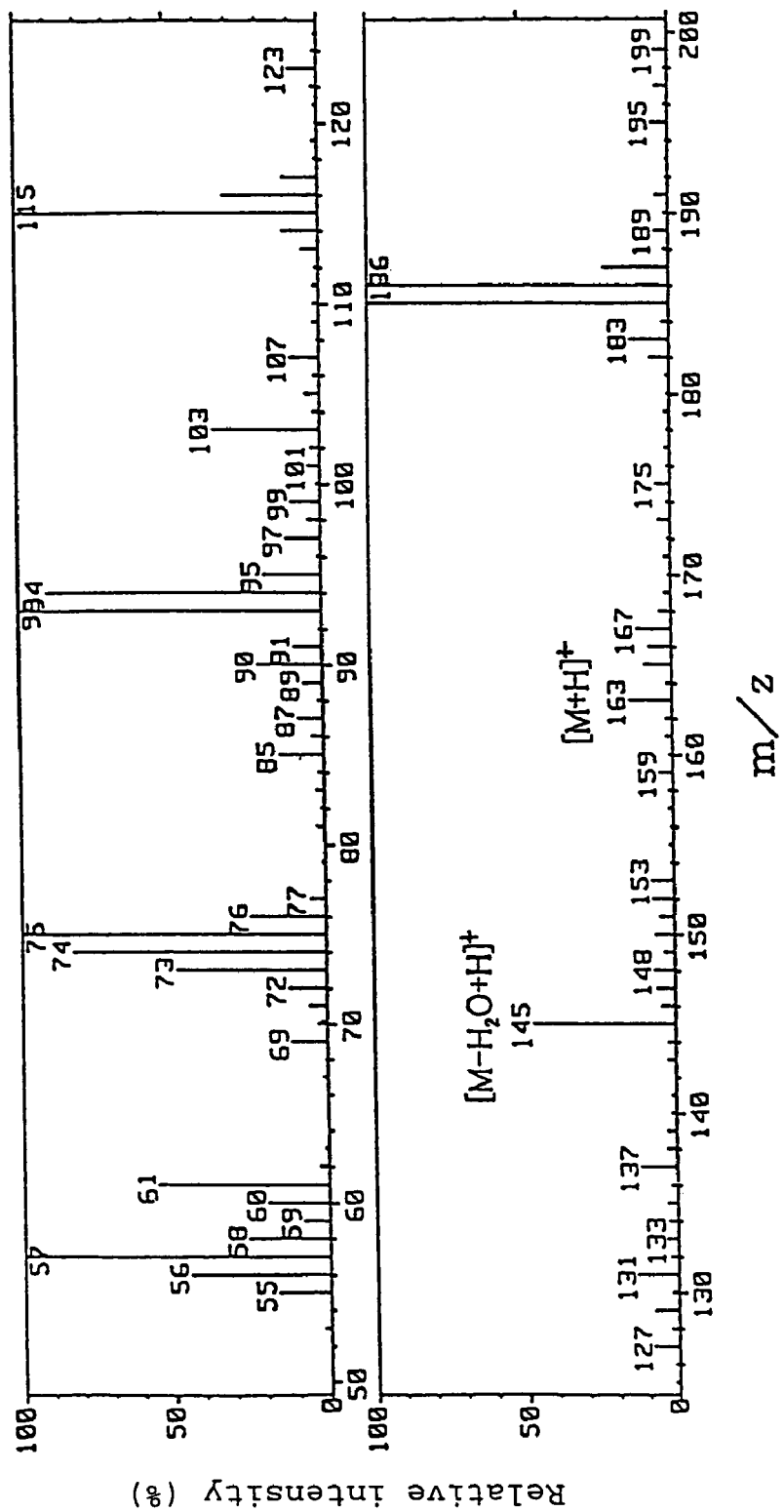
FIG. 11 illustrates a mass spectrum of 3,6-anhydro-L-galactose.
Figure 12:
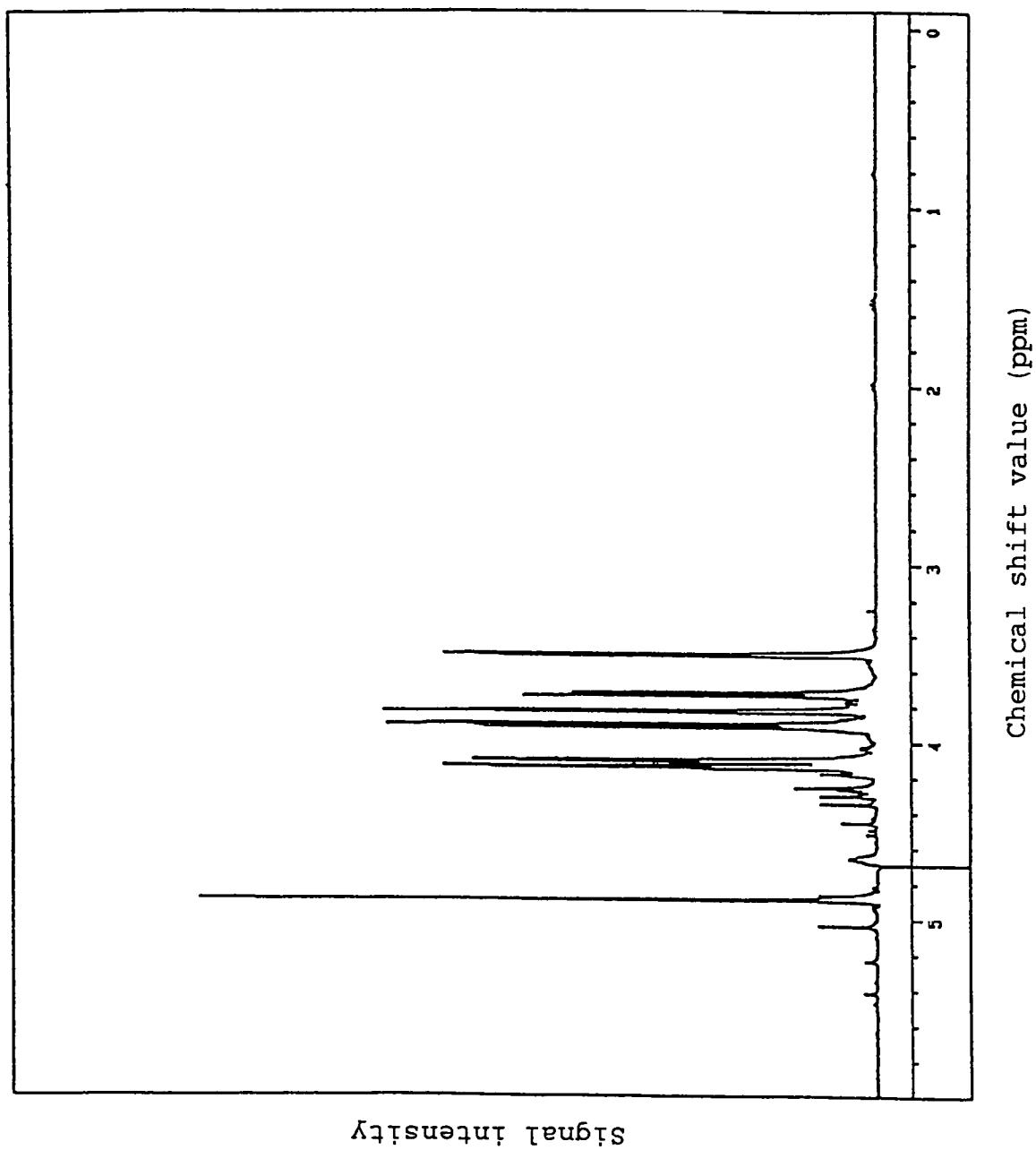
FIG. 12 illustrates a $^1$H-NMR spectrum of 3,6-anhydro-L-galactose (hydrate).
Figure 13:
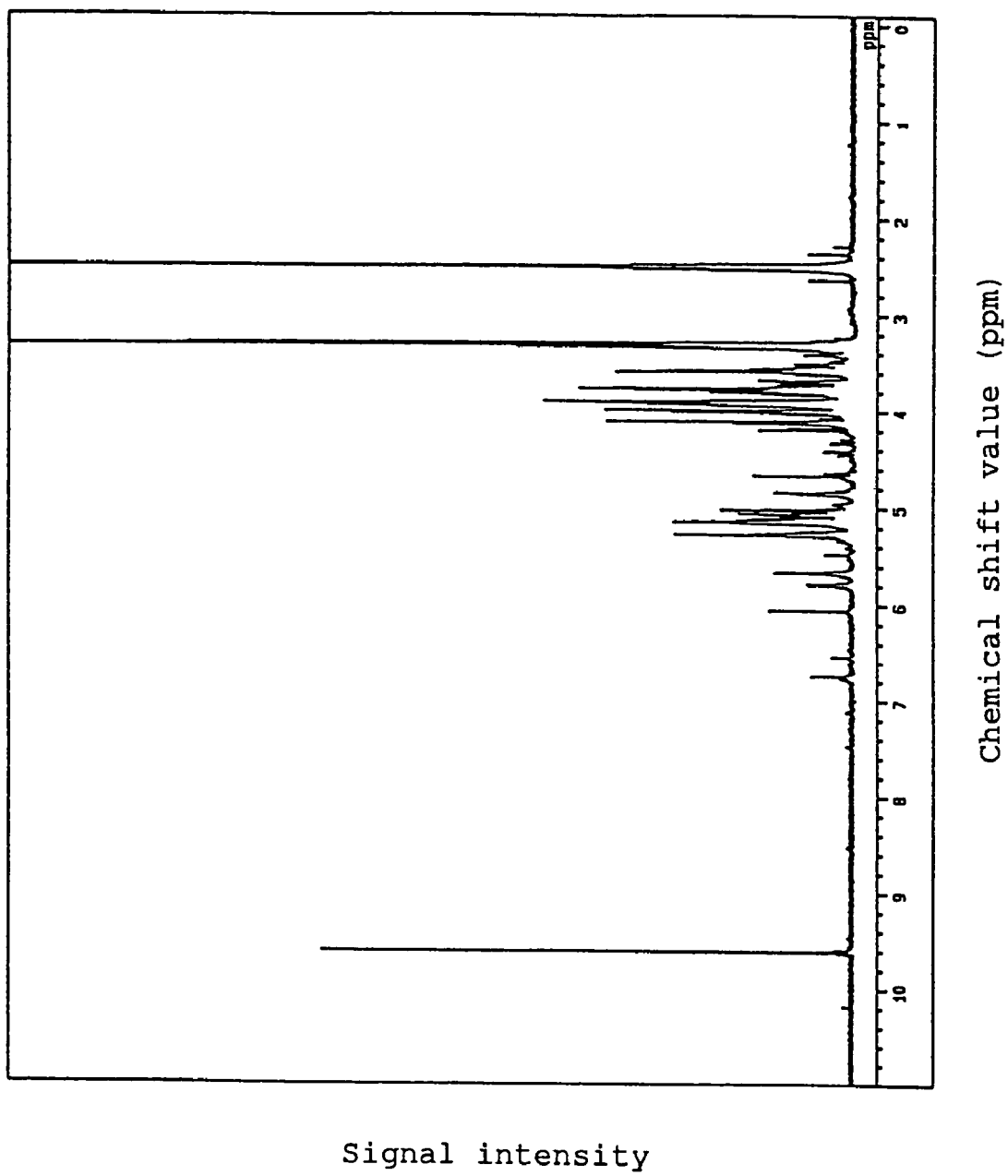
FIG. 13 illustrates a $^1$H-NMR spectrum of 3,6-anhydro-L-galactose (aldehyde).

The results are shown in FIGS. 11 to 13. That is, FIG. 11 illustrates the mass spectrum of 3,6-anhydro-L-galactose. The horizontal axis represents the m/z value and the vertical axis represents the relative intensity (%). FIG. 12 illustrates the $^1$H-NMR spectrum of 3,6-anhydro-L-galactose in heavy water and FIG. 13 illustrates the $^1$H-NMR spectrum of 3,6-anhydro-L-galactose in heavy dimethyl sulfoxide solvent. In the figures, the horizontal axes represent the chemical shift value, and the vertical axes represent the signal intensity.

For 3,6-anhydro-L-galactose, $^1$H-NMR spectrum in heavy dimethyl sulfoxide solvent also showed the proton signal of aldehyde at 9.60 ppm. This demonstrated that it was present as an aldehyde whose ring was opened in a non-aqueous solvent. Furthermore, from the $^1$H-NMR spectrum in heavy water, it was present as a hydrate of the aldehyde in an aqueous solution.

EXAMPLE 4

(1) A 20 mM solution of 3,6-anhydro-L-galactose obtained in Example 3 was diluted 2-, 4- and 8-folds with sterilized water and, according to the same manner as that described in Example 2-(1), an apoptosis-inducing activity and an anti-proliferation activity against tumor cells of respective dilutions were measured. As a result, in the group to which the 2-fold dilution of 3,6-anhydro-L-galactose was added (at the final concentration of 1 mM), apoptosis corpuscles were observed and the absorbance at 590 nm became less than one-half of that of the control group to which water was added.

(2) A 50 mM solution of agarobiose, agarotetraose or agarohexaose obtained in Example 3-(1) was sterilized by filtration and diluted 2-, 4-, 8-, 16-, 32-, 64- and 128-folds with sterilized water. According to the same manner as that described in Example 2-(1), an anti-proliferation activity against various cells of the resultant dilutions was measured. The cells and culture media used are shown in Tables 1 and 2.

TABLE 1

| Cells | Medium |
|---|---|
| Human promyelocytic leukemia HL-60 (ATCC CCL 240) | RPMI 1640 medium (Nissui) supplemented with 10% fetal bovine serum (Gibco) |

TABLE 1-continued

| Cells | Medium |
|---|---|
| Human peripheral lymphocyte RPMI 1778 (ATCC CCL 156) | the same as the above |
| Mouse monocyte RAW 264.7 (ATCC TIB 71) | DMEM medium supplemented with 10% fetal bovine serum (Nissui) |
| Human gastric cancer cell MKN 45 (Riken gene bank, RCB 1001) | RPMI 1640 medium supplemented with 10% fetal bovine serum |
| Human hepatoma cancer cell HepG2 (ATCC HB 8065) | DMEM medium supplemented with 10% fetal bovine serum |
| Human colonic adenocarcinoma HT-29 (ATCC HTB 38) | McCoy's medium supplemented with 10% fetal bovine serum (BioWhittaker) |
| Human colonic adenocarcinoma HCT116 (ATCC CCL-247) | the same as the above |
| Fibrosarcoma HT-1080 (ATCC CCL-121) | DMEM medium supplemented with 10% fetal bovine serum (BioWhittaker) |

TABLE 2

| Cells | Medium |
|---|---|
| Glial blast cell A-172 (ATCC CRL1620) | DMEM medium supplemented with 10% fetal bovine serum |
| Human breast cancer MCF7 (ATCC HTB-22) | DMEM medium supplemented with 10% fetal bovine serum |
| Human breast cancer T-47D (ATCC HTB-133) | RPMI 1640 medium supplemented with 10% fetal bovine serum |
| Human bladder carcinoma T24 (ATCC HTB-4) | McCoy's medium supplemented with 10% fetal bovine serum |
| Human cancer of the uterine cervix cell HeLa S3 (ATCC CCL-22) | DMEM medium supplemented with 10% fetal bovine serum |
| Human lung cancer A549 (ATCC CCL-185) | the same as the above |
| Human colonic adenocarcinoma WiDr (ATCC CCL-218) | RPMI 1640 medium supplemented with 10% fetal bovine serum |

As a result, agarobiose, agarotetraose and agarohexaose exhibited an antiproliferation activity against these cells. The results are shown in Table 3.

The number in Table 3 represents the dilution rate of the dilution added to the group whose absorbance at 590 nm was less than one-half of that of the control group to which water was added. The dilution rate 1 corresponds to the concentration of 5 mM in the cell culture medium. Then, for agarobiose, agarotetraose and agarohexaose, the concentrations required for 50% proliferation inhibitory rate (IC$_{50}$) are calculated based on the change in the absorbance at 590 nm, and are shown in Table 4.

TABLE 3

| Cells | Agarobiose | Agarotetraose | Agarohexaose |
|---|---|---|---|
| HL-60 | 32 | 64 | 64 |
| RPMI1788 | 64 | 128 | 128 |
| RAW264.7 | 16 | 32 | 32 |
| MKN45 | 8 | 16 | 16 |
| HepG2 | 8 | 8 | 16 |
| HT-29 | 8 | 16 | 32 |
| HCT116 | 16 | 32 | 32 |
| HT-1080 | 8 | 16 | 16 |
| A-172 | 16 | 16 | 16 |
| MCF7 | 16 | 16 | 16 |
| T-47D | 16 | 16 | 16 |
| T24 | 8 | 8 | 8 |

TABLE 3-continued

| Cells | Agarobiose | Agarotetraose | Agarohexaose |
|---|---|---|---|
| HeLa S3 | 8 | 8 | 16 |
| A549 | 8 | 8 | 16 |
| WiDr | 8 | 8 | 16 |

TABLE 4

| | $IC_{50}$ (μM) | | |
|---|---|---|---|
| Cells | Agarobiose | Agarotetraose | Agarohexaose |
| HL-60 | 170 | 97 | 78 |
| RPMI1788 | 44 | 28 | 22 |
| RAW264.7 | 179 | 133 | 109 |
| MKN45 | 344 | 196 | 166 |
| HepG2 | 652 | 413 | 430 |
| HT-29 | 622 | 208 | 144 |
| HCT116 | 244 | 158 | 136 |
| HT-1080 | 317 | 216 | 185 |
| A-172 | 289 | 185 | 151 |
| MCF7 | 274 | 276 | 238 |
| T-47D | 210 | 183 | 158 |
| T24 | 352 | 399 | 365 |
| HeLa S3 | 353 | 400 | 334 |
| A549 | 570 | 494 | 279 |
| WiDr | 405 | 399 | 334 |

EXAMPLE 5

A suspension of 5 g of commercially available agar in 50 ml of 0.1 N HCl was heated at 100 C for 13 minutes. After cooling to room temperature, the solution was neutralized to about neutral pH with NaOH and 2 ml of the solution was applied to a column (10×255 mm) packed with activated carbon (60-150 mesh, 079-21, manufactured by Nacalai Tesque) washed with water. The column was washed with 200 ml of water and then eluted with each 200 ml of 2.5%, 5%, 7.5%, 10%, 12.5%, 15%, 17.5%, 20%, 22.5%, 25%, 27.5%, 30%, 35%, 40%, 45% and 50% aqueous ethanol in this order.

Each eluted fraction was concentrated 10-folds under reduced pressure and spotted on a silica gel sheet $60F_{254}$ (manufactured by Merck) and developed with 1-butanol:ethanol:water=5:5:1. Orcinol reagent [prepared by dissolving 400 mg of orcinol monohydrate (manufactured by Nacalai Tesque) in 22.8 ml of sulfuric acid and adding water thereto to make the final volume up to 200 ml] was sprayed to observe the resultant spots.

As a result, agarobiose with high purity was contained in the fractions eluted with 5% and 7.5% aqueous ethanol; agarotetraose with high purity was contained in the fractions eluted with 15% and 17.5% aqueous ethanol; agarohexaose with high purity was contained in the fractions eluted with 22.5% and 25% aqueous ethanol; and agarooctaose with high purity was contained in the fractions eluted with 27.5% and 30% aqueous ethanol.

EXAMPLE 6

Agarobiose, agarotetraose, agarohexaose and agarooctaose (hereinafter, sometimes, these oligosuccharaides are referred to as agarooligosaccharides) obtained in Example 5 were dissolved in water at a concentration of 2.5 mM or 1.25 mM separately, and were sterilized by filtration. HL-60 cells were suspended in RPMI 1640 medium containing 10% fetal bovine serum at a concentration of $2.5 \times 10^5$ cells/4.5 ml and to this suspension was added 0.5 ml of each of the oligosaccharide solutions. The resultant mixture were incubated with 5% $CO_2$ at 37° C. for 24 hours or 48 hours. A part of the cell culture was taken up, followed by addition of Trypan Blue thereto and observing under a microscope to count the number of viable cells. As a result, the number of viable cells in each group was decreased as compared with the group to which water was added (control) and apoptosis corpuscles were observed.

Figure 14:
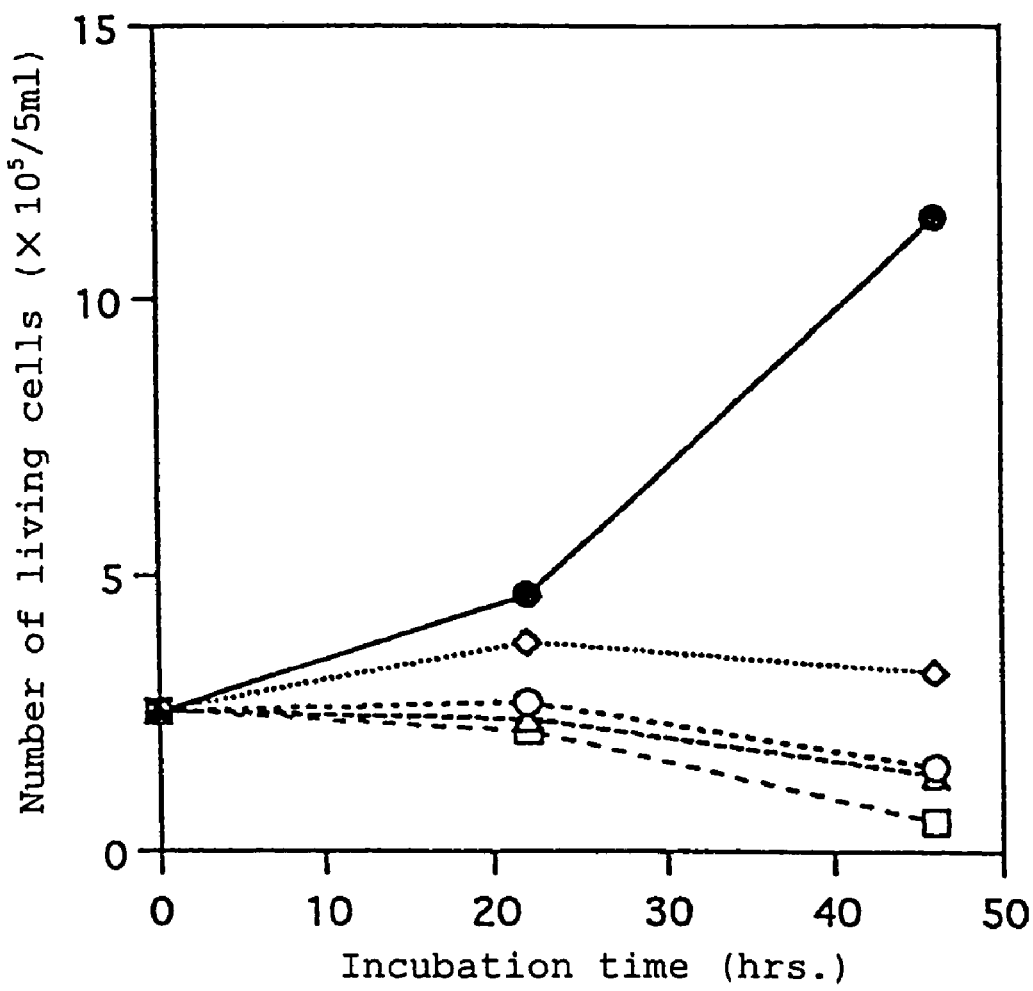
FIG. 14 illustrates the relation between the incubation time and the number of viable cells obtained by incubating HL-60 cells with addition of one of oligosaccharides at a final concentration of 250 μM.
Figure 15:
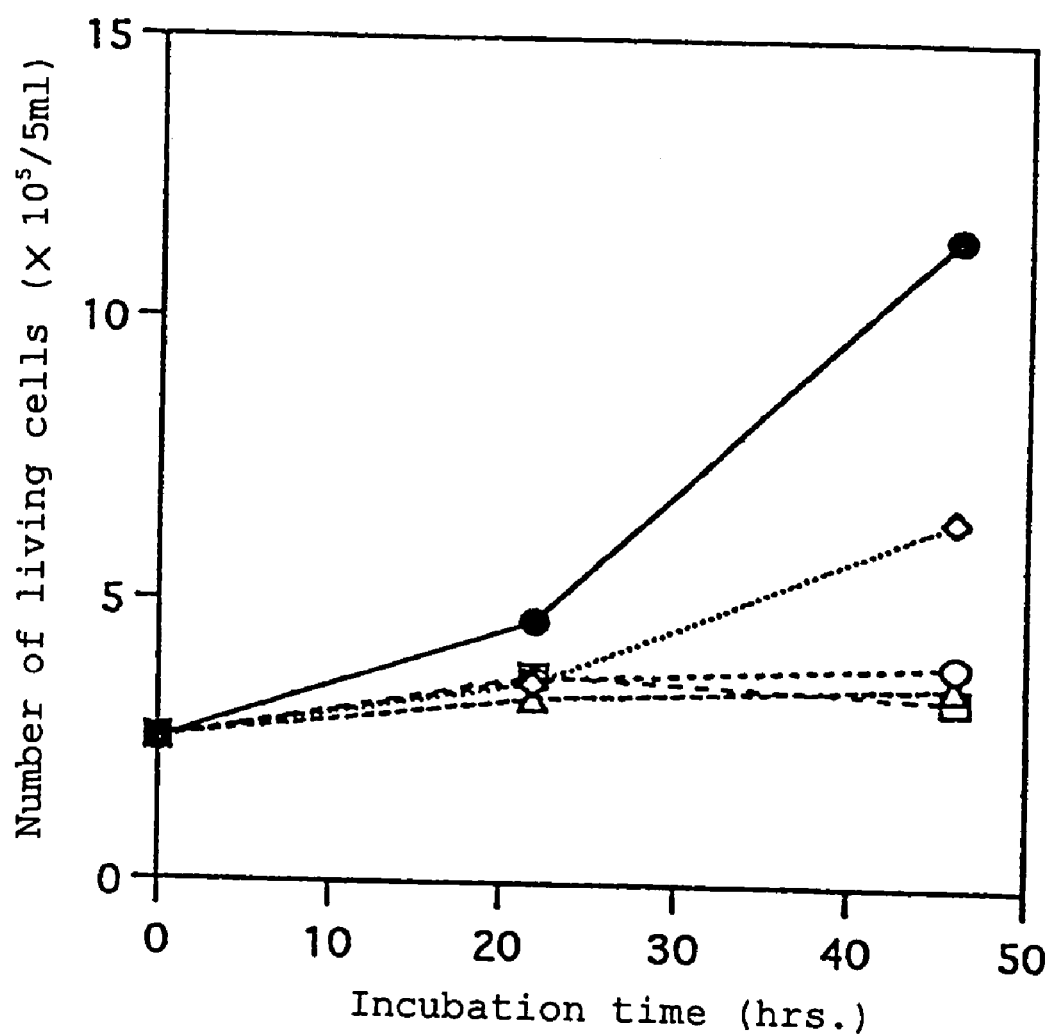
FIG. 15 illustrates the relation between the incubation time and the number of viable cells obtained by incubating HL-60 cells with addition of one of oligosaccharides at a final concentration of 125 μM.

The results are shown in FIGS. 14 and 15. That is, FIG. 14 illustrates the relation between the incubation time and the number of viable cells when HL-60 cells were cultured with addition of one of the oligosaccharides at the final concentration of 250 μM. FIG. 15 illustrates the relation between the incubation time and the number of viable cells when HL-60 cells were cultured with addition of one of the oligosaccharides at the final concentration of 125 μM. In FIGS. 14 and 15, the horizontal axes represent the incubation time (hrs.) and the vertical axes represent the number of viable cells ($\times 10^5/5$ ml). The closed circle (●) represents the addition of water (control), the open diamond (□) represents the addition of agarobiose, the open circle (□) represents the addition of agarotetraose, the open triangle (□) represents the addition of agarohexaose and the open square (□) represents the addition of agarooctaose.

EXAMPLE 7

(1) A suspension of 0.2 g of κ-carrageenan (manufactured by Sigma, C-1263) or λ-carrageenan (manufactured by Wako Pure Chemical Industries, Ltd., 038-14252) in 20 ml of 0.1 N HCl was heated at 95 C for 10 minutes. After neutralizing with 1N NaOH, the resultant mixture was diluted 1.5-, 2.25-, 3.38- and 5.06-folds with water and an anti-proliferation activity against HL-60 cells was measured according to the same manner as that described in Example 2-(1). As a result, in the groups to which the 1.5-, 2.25- and 3.38-fold dilutions of heated κ-carrageenan and the 1.5- and 2.25-fold dilutions of heated λ-carrageenan were added, the absorbance at 590 nm was less than one-half of that of the control group to which water was added, and apoptosis corpuscles were observed.

(2) Commercially available agar (Agar Noble), agarose L03 (manufactured by Takara Shuzo) and commercially available bar-shaped agar were suspended in 1N HCl at a concentration of 1%, respectively, and heated at 100 C for 15 minutes. After cooling, the heated mixtures were neutralized with 1N NaOH and diluted 2-, 4-, 8- and 16-folds with water, respectively. An anti-proliferation activity against HL-60 cells of the resultant dilutions were measured according to the same manner as that described in Example 2-(1). As a result, in the groups to which the 2- to 8-fold dilutions of the acid decomposition products of agar and agarose and the 2- and 4-fold dilutions of the acid decomposition product of bar-shaped agar were added, the absorbance at 590 nm was less than one-half of that of the control group to which water was added, and apoptosis corpuscles were observed.

When each of the acid decomposition products was analyzed with normal phase HPLC, agarooligosaccharaides such as agarobiose, etc. were detected for all the decomposition products.

EXAMPLE 8

(1) Commercially available agar was suspended in each of the following aqueous acid solutions at a concentration of 1%.

0.5 M, 1M or 2M citric acid; 0.1 M, 0.5 M, 1 M or 2 M nitric acid; 0.1 M or 0.5 M sulfuric acid; 0.1 M, 0.5 M or 1 M phosphoric acid; 0.1 M hydrochloric acid.

The resultant agar suspensions were heated with a microwave oven until the agar was dissolved, followed by neutralization with NaOH. The solutions were diluted with 2-, 4-, 8-, 16- or 32-folds with distilled water. Then, an apoptosis-inducing activity and an antiproliferation activity against HL-60 cells were measured according to the same manner as that described in Example 2-(1).

As a result, agar heated in the above-listed various acids induced apoptosis in HL-60 cells and inhibited cell proliferation. The results are shown in Table 5. The number in Table 5 represents the dilution rate of the dilution added to the group whose absorbance at 590 nm was less than one half of that of the control group to which water was added. In addition, the number in the parentheses represents the dilution rate of a solution (prepared, without adding agar, by neutralizing the highest concentration of the acid used in this Example with NaOH and diluting the resulting solution with distilled water) added to the group whose absorbance at 590 nm was less than one-half of that of the control group to which water was added.

TABLE 5

|  | 0.1 M | 0.5 M | 1 M | 2 M |
|---|---|---|---|---|
| Citric acid |  | 4 | 8 | 16(8) |
| Nitric acid | 8 | 16 | 16(2) |  |
| Sulfuric acid | 8 | 16(2) |  |  |
| Phosphoric acid | 4 | 8 | 16(1) |  |
| Hydrochloric acid | 16 |  |  |  |

(2) The substances obtained by heating agar in the acids in Example 8-(1) were analyzed with normal phase HPLC as follows.

Column: PALPAK type S (4.6×250 mm, manufactured by Takara Shuzo, CA8300)
Solvent A: aqueous 90% acetonitrile solution
Solvent B: aqueous 50% acetonitrile solution
Flow rate: 1 ml/min.
Elution: solvent A (10 min.) linear gradient from solvent A to solvent B (40 min.) solvent B (10 min.)
Detection: absorbance at 195 nm
Column temperature: 40° C.

As a result, the samples heated in 0.5 M, 1 M and 2 M citric acid, 0.1 M, 0.5 M, 1 M and 2 M nitric acid, 0.1 M and 0.5 M sulfuric acid, 0.1 M, 0.5 M and 1 M phosphoric acid, and 0.1 M hydrochloride acid contained agarooligosaccharides such as agarobiose, etc.

Figure 16:
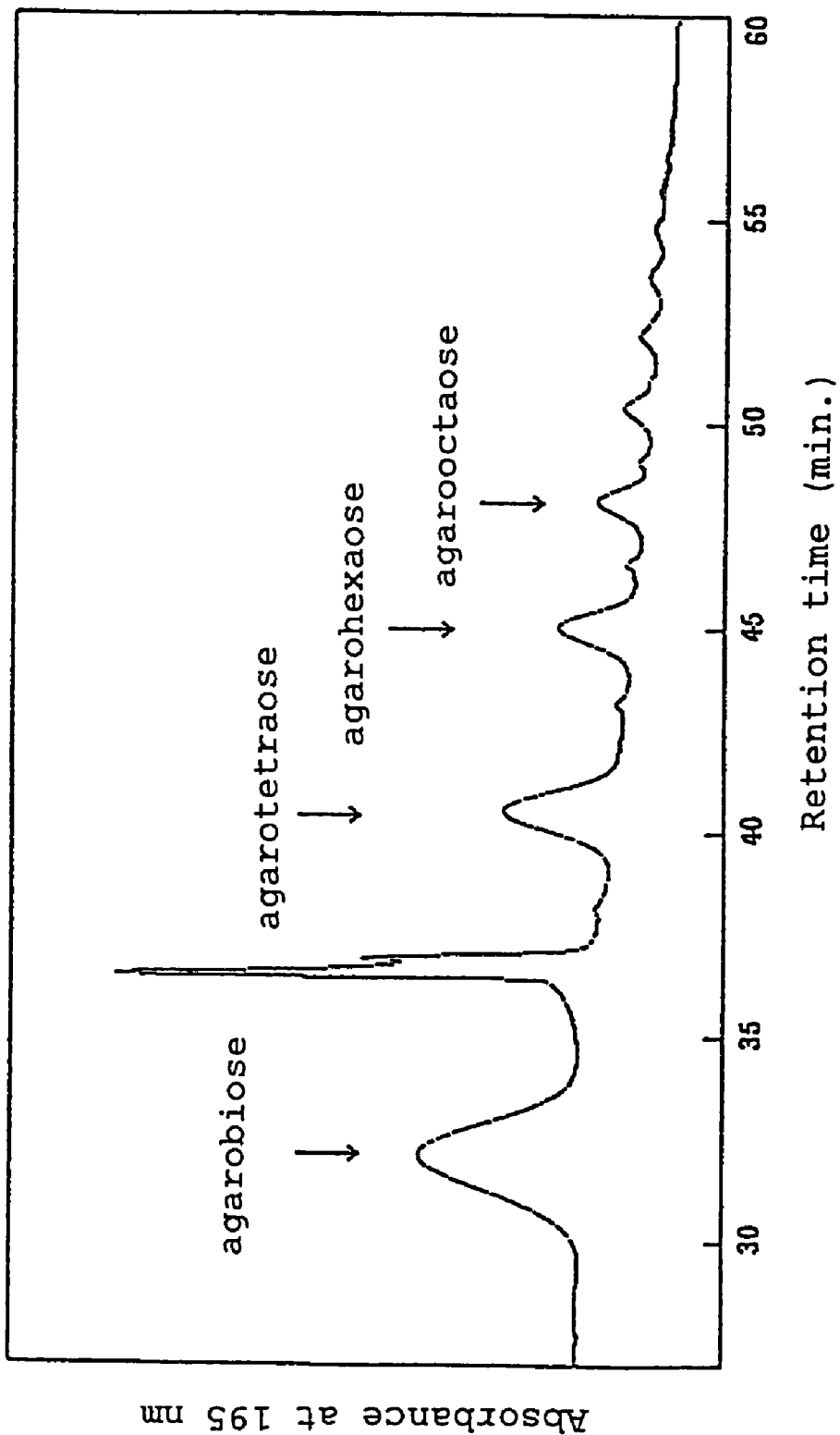
FIG. 16 illustrates an elution pattern in normal phase HPLC chromatogram of agar treated by heating in 0.5 M phosphate.

The representative result is shown in FIG. 16. That is, FIG. 16 illustrates the normal phase HPLC elution pattern of agar heated in 0.5 M phosphoric acid. In FIG. 16, the horizontal axis represents the retention time (min.) and the vertical axis represents the absorbance at 195 nm.

EXAMPLE 9

A suspension of 5 g of commercially available agar (Ina agar type S-7, manufactured by Ina Shokuhin Kogyo) in 45 ml of 20, 50 or 100 mM citric acid was heated at 95° C. Samples were obtained after heating for a period of time as described below.

For 20 mM citric acid, 310 min., 350 min., 380 min., 440 min. and 530 min.

For 50 mM citric acid, 100 min., 120 min., 140 min., 160 min., 180 min., 200 min., 220 min., 240 min., 260 min., 290 min. and 320 min.

For 100 mM citric acid, 60 min., 70 min., 80 min., 90 min., 100 min., 120 min., 140 min., 160 min., 180 min., 200 min., 220 min. and 240 min.

1 µl of 10-fold dilution of each sample was spotted on a silica gel 60 sheet $F_{254}$ (manufactured by Merck), developed with 1-butanol:ethanol:water=5:5:1 and detected by orcinol-sulfuric acid method.

As a result, each sample contained agarooligosaccharides such as agarobiose, agarotetraose and agarohexaose, etc.

For the samples treated with 20 mM citric acid, the agarooligosaccharide content was increased by heating for as long as 350 minutes and, thereafter, remained almost constant.

For the samples treated with 50 mM citric acid, the agarooligosaccharide content was increased by heating for as long as 200 minutes and, thereafter, remained almost constant.

For the samples treated with 100 mM citric acid, the agarooligosaccharide content was increased by heating for as long as 160 minutes and, thereafter, remained almost constant.

The final agarooligosaccharide content increased with the increase in the concentration of citric acid.

Each sample was analyzed with the normal phase HPLC according to the same manner as that described in Example 8-(2). As a result, results consistent with those obtained by thin layer chromatography were obtained. However, the sample treated with 100 mM citric acid contained more impurities than that treated with 50 mM citric acid, and the impurities increased with the increase in the heating time.

EXAMPLE 10

(1) Agarobiose prepared in Example 3-(1) was dissolved at a concentration of 0.05 mM, 0.1 mM, 0.2 mM, 0.4 mM, 0.6 mM, 0.8 mM or 1 mM in water. One microliter of each sample was spotted on a silica gel 60 sheet $F_{254}$, developed three times with chloroform:methanol:acetic acid=7:2:2 and color-developed by orcinol-sulfuric acid method. Image data of the color-developed sheet was obtained using FOTODYNE FOTO/Analyst Archiver Ecripse (sold by Central Kagaku Bouekisha). The image data was image-processed using an image analysis software 1-D Basic (manufactured by Advanced American Biotechnology) and the intensity of the agarobiose spot at each concentration was converted to a numerical value to prepare a calibration curve.

Figure 17:
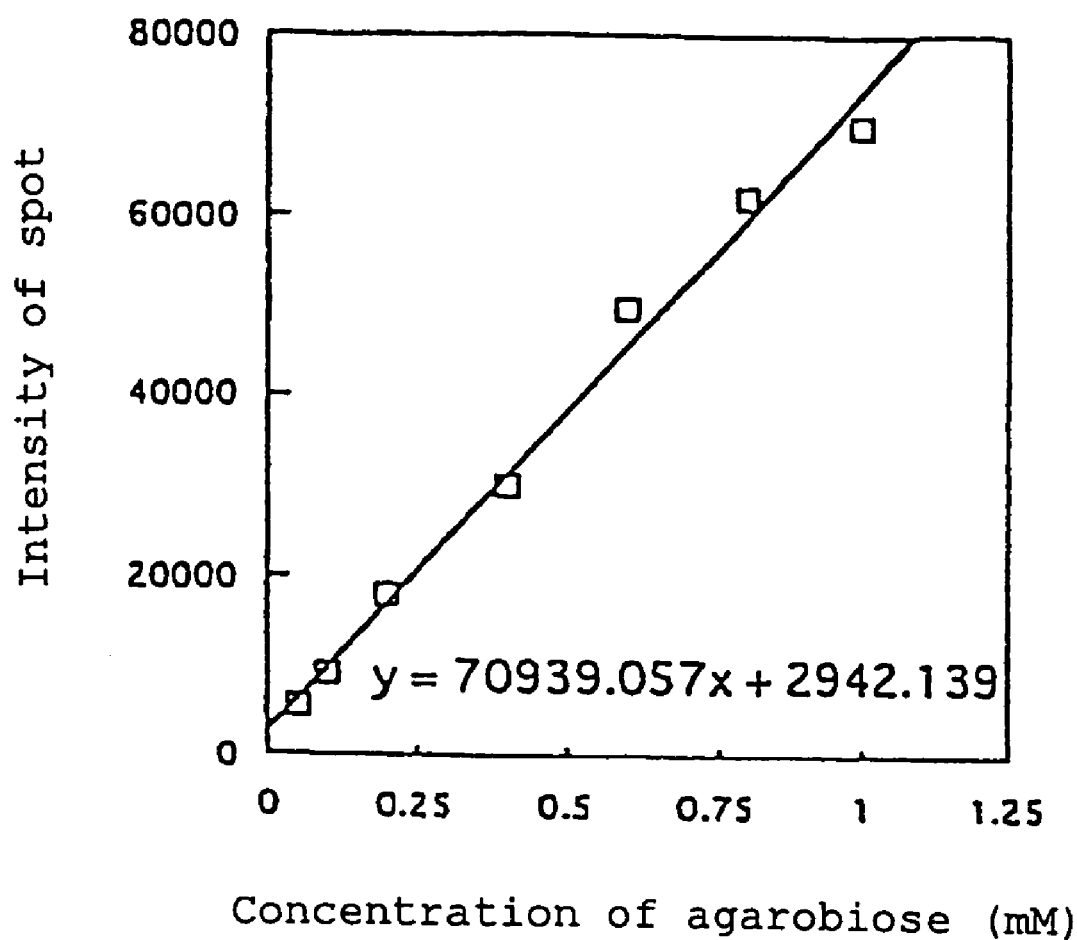
FIG. 17 illustrates a calibration curve of agarobiose.

A graph of the calibration curve is shown in FIG. 17. That is, FIG. 17 illustrates the calibration curve for agarobiose, and the graph was prepared by plotting each agarobiose concentration versus the intensity of each spot. In FIG. 17, the horizontal axis represents the agarobiose concentration (mM) and the vertical axis represents the intensity of spot. The equation in FIG. 17 represents the relation of the intensity of spot (y) and the agarobiose concentration (x). For a sample whose agarobiose concentration is unknown, the agarobiose concentration can be calculate from the equation by determining the intensity of spot.

Likewise, calibration curves for agarotetraose, agarohexaose and agarooctaose obtained in Example 5 were prepared.

(2) A suspension of 0.2 g of commercially available agar (Agar Noble) in 90 ml of water was heated with a microwave oven and cooled to about room temperature. To this resultant solution was added 10 ml of 1 M HCl or 1 M citric acid to prepare 0.2% agar solution in 0.1 M HCl or 0.2% agar solution in 0.1 M citric acid. The solution was heated at 90 C and samples were obtained at 5 min., 10 min., 20 min., 30 min., 1 hour, 2 hours, 4 hours, 8 hours and 21 hours after initiation of heating. Each sample was subjected to the thin layer chromatography according to the same manner as that described in Example 10-(1) and the intensity of spot was determined to calculate the agarobiose concentration. Each sample was appropriately diluted to make the agarobiose concentration within a range between 0.05 mM and 1 mM.

Figure 18:
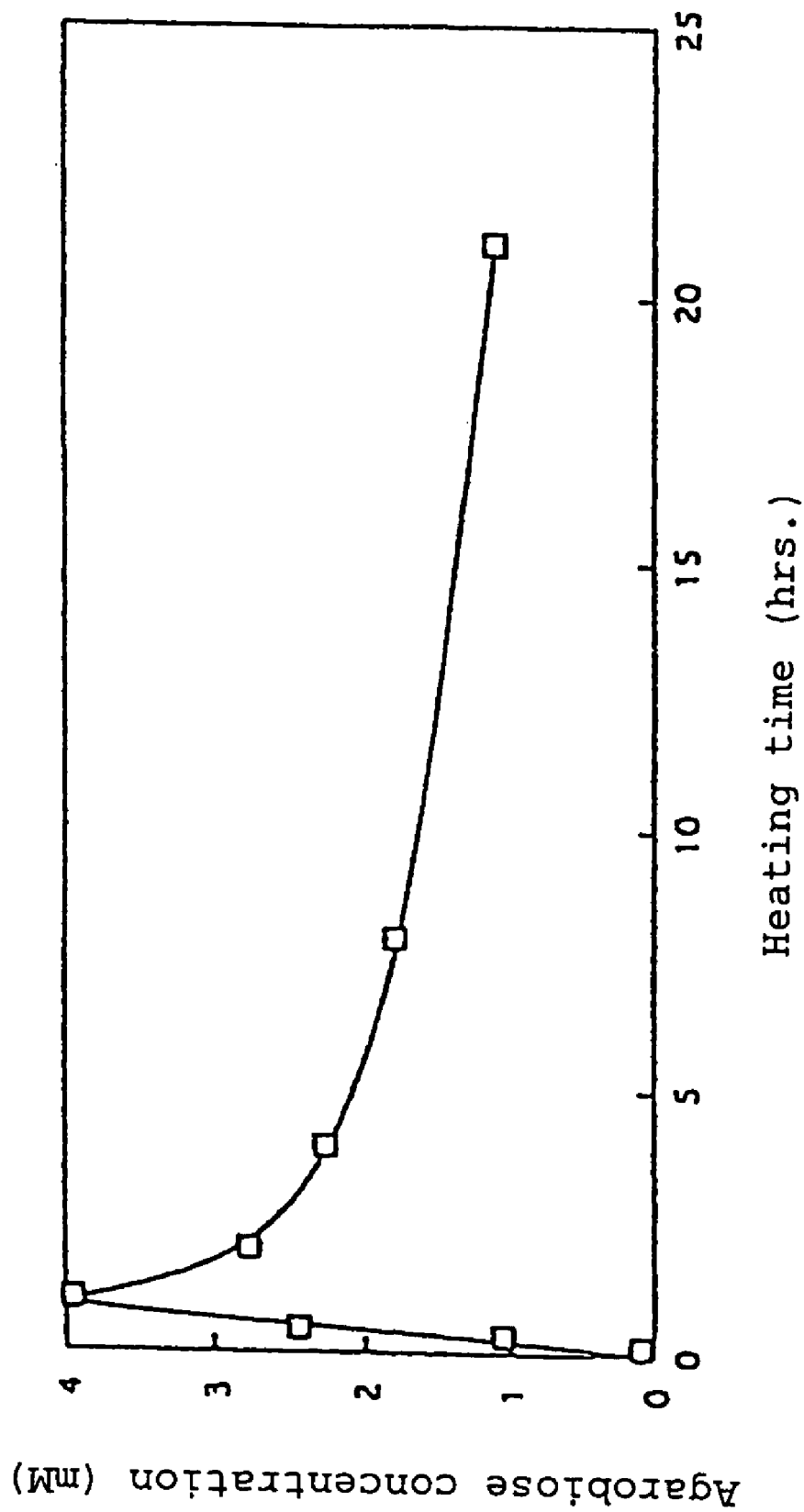
FIG. 18 illustrates the relation between the heating time and the amount of agarobiose produced in 0.2% agar solution in 0.1 M HCl.
Figure 19:
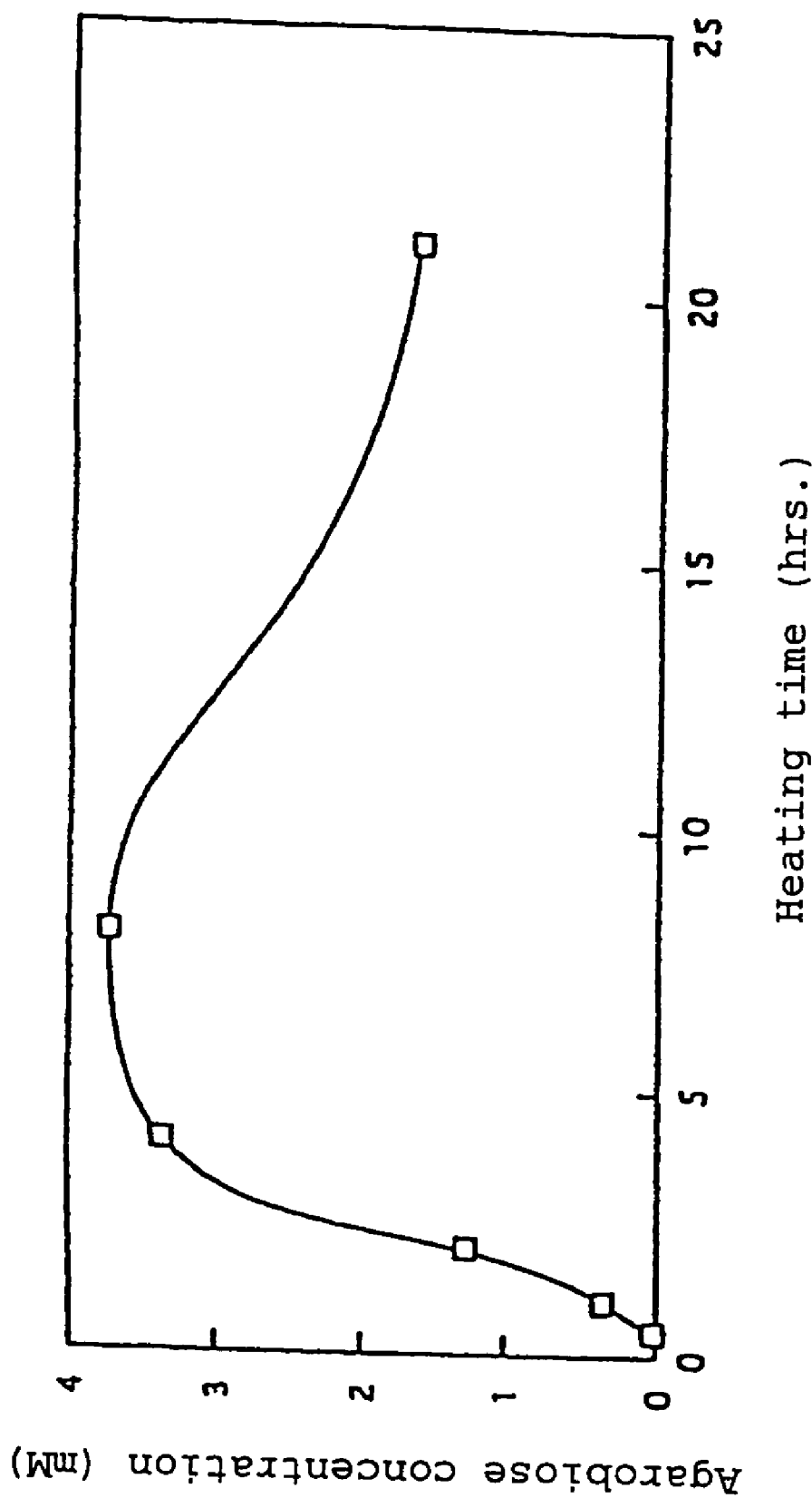
FIG. 19 illustrates the relation between the heating time and the amount of agarobiose produced in 0.2% agar solution in 0.1 M citric acid.

In FIGS. 18 and 19, the relation between the heating time and the amount of agarobiose formed in 0.2% agar solution in 0.1 M HCl and 0.2% agar solution in 0.1 M citric acid. That is, FIG. 18 illustrates the relation between the heating time and the amount of agarobiose formed in 0.2% agar solution in 0.1 M HCl. FIG. 19 illustrates the relation between the heating time and the amount of agarobiose formed in 0.2% agar solution in 0.1 M citric acid. In FIG. 18 and FIG. 19, each horizontal axis represents the heating time (hrs.) and the vertical axis represents the agarobiose concentration (mM).

As shown in FIG. 18, in 0.2% agar solution in 0.1 M HCl, the agarobiose concentration reached the maximum by heating for one hour and reduced thereafter. And, as shown in FIG. 19, in 0.2% agar solution in 0.1 M citric acid, the agarobiose concentration increased gradually by heating as long as 8 hours and reduction was observed at 21 hours. The agarobiose concentration in a sample obtained by heating 0.2% agar solution in 0.1 M HCl for 5 minutes, or by heating 0.2% agar solution in 0.1 M citric acid for 5, 10, or 20 minutes was below the detectable limitation.

(3) Agar Noble was suspended in 5, 50 and 500 mM citric acid at a concentration of 10%, heated at 65, 80 or 95° C. Samples were obtained at 30 min., 1, 2, 4, 8 or 24 hours after the initiation of heating and, according to the same manner as that described in Example 10-(1), the amount of agarooligosaccharides formed was measured.

As a result, when agar was dissolved in 5 mM citric acid, although small amounts of agarooligosaccharides were formed at 80° C., they were scarcely formed at 65° C. At 95° C., a large amount of agarobiose was formed by heating for 8 to 24 hours, and a large amount of agarotetraose was also formed by heating for 8 to 24 hours. When agar was dissolved in 50 mM citric acid, agarooligosaccharides were scarcely formed at 65° C. At 80° C., a large amount of agarobiose was formed by heating for 24 hours, and large amounts of agarotetraose, agarohexaose and agarooctaose were formed by heating for 4 to 8 hours. At 95° C., a large amount of agarobiose was formed by heating for 24 hours, and large amounts of agarotetraose, agarohexaose and agarooctaose were formed by heating for 4 to 8 hours. When agar was dissolved in 500 mM citric acid, small amounts of agarooligosaccharides were formed by heating at 65° C. for 4 to 24 hours. At 80° C., a large amount of agarobiose was formed by heating for 2 to 24 hours, and large amounts of agarotetraose and agarohexaose were formed by heating for 1 to 6 hours. A large amount of agarooctaose was formed by heating for 1 to 2 hours. At 95° C., a large amount of agarobiose was formed by heating for 1 to 24 hours, and a large amount of agarotetraose was formed by heating for 1 to 2 hours. Large amounts of agarohexaose and agarooctaose were formed by heating for 30 minutes to 1 hour.

Figure 20:
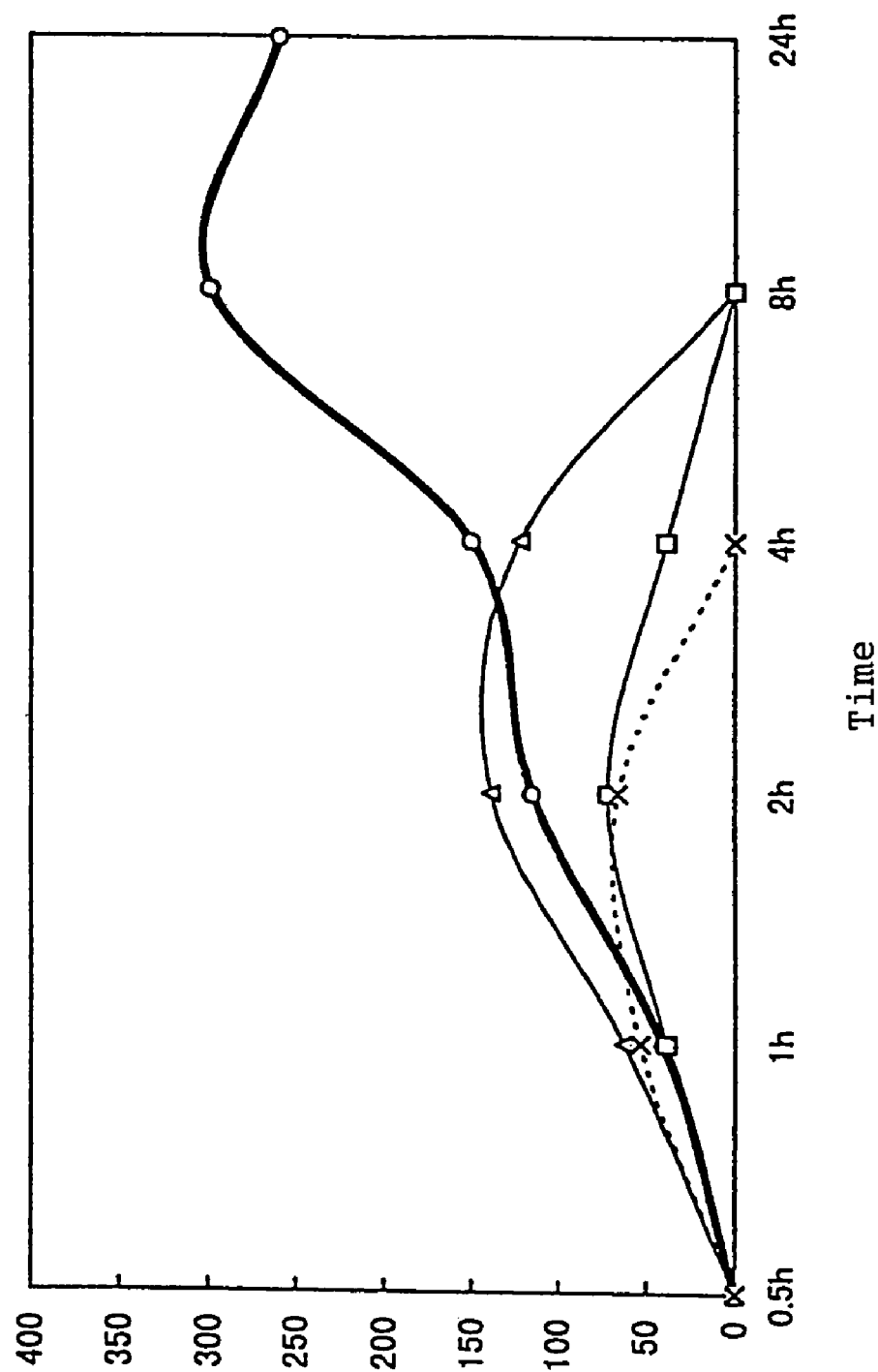
FIG. 20 illustrates the production of agarooligosaccharides in 500 mM citric acid at 80 C.
Figure 21:
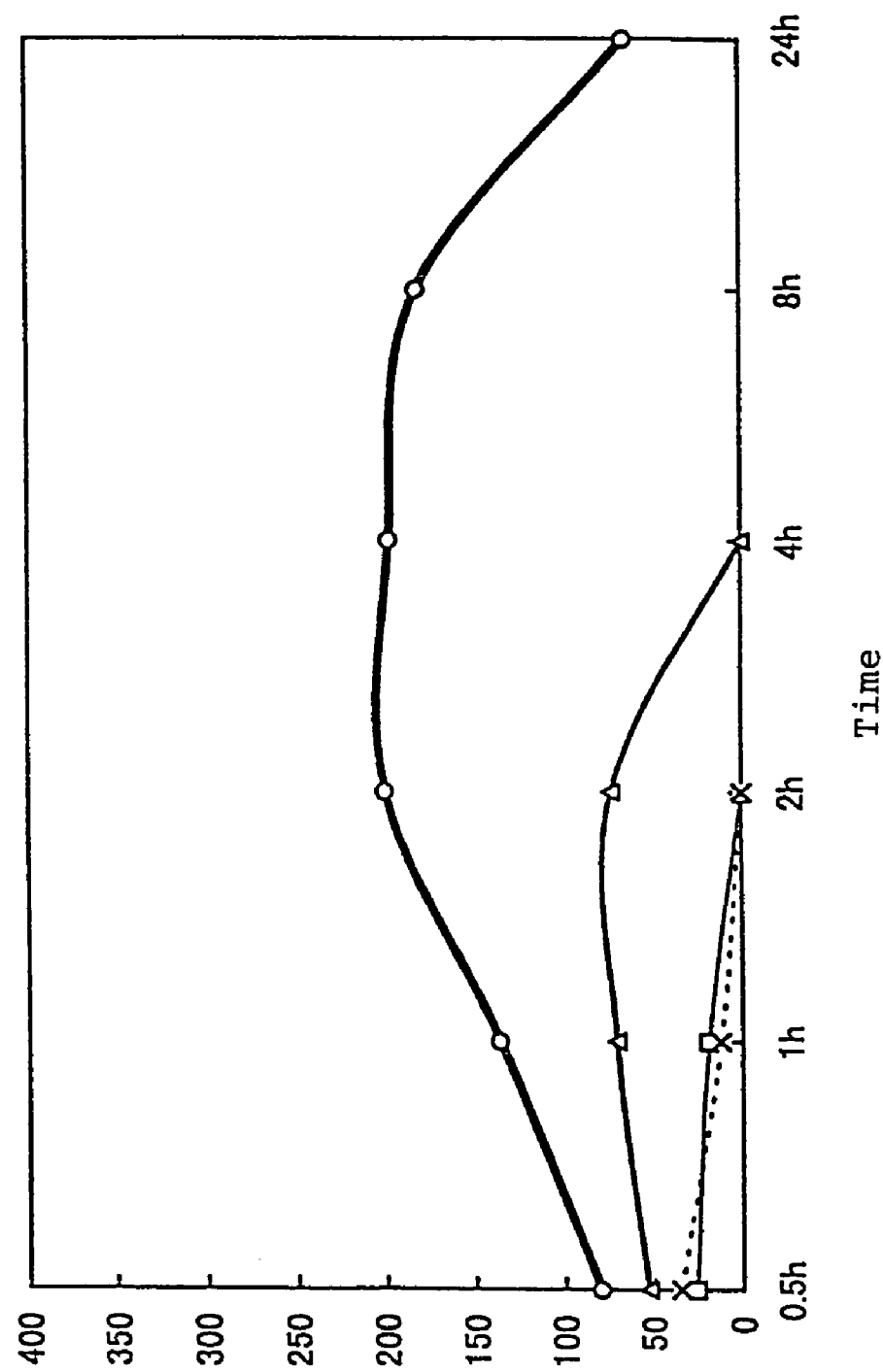
FIG. 21 illustrates the production of agarooligosaccharides in 500 mM citric acid at 95 C.

Examples of hydrolysis by 500 mM citric acid are shown in FIGS. 20 and 21. That is, FIG. 20 illustrates agarooligosaccharide formation in 500 mM citric acid by heating at 80° C. In FIG. 20, the vertical axis represent the amounts of agarooligosaccharides formed (open circle: agarobiose, open triangle: agarotetraose, open square: agarohexaose, symbol x: agarooctaose) and the horizontal axis represents the time. FIG. 21 illustrates the amounts of agarooligosaccharide formation in 500 mM citric acid by heating at 95° C. In FIG. 21, the vertical axis represents the amounts of agarooligosaccharides formed (open circle: agarobiose, open triangle: agarotetraose, open square: agarohexaose, symbol x: agarooctaose) and the horizontal axis represents the time.

(4) According to the same manner as that described in Example 10-(3), agarooligosaccharide formation in 50, 500 or 1000 mM acetic acid was measured.

As a result, when agar was dissolved in 50 mM acetic acid, small amounts of agarooligosaccharides were formed at 80° C., while agarooligosaccharides were scarcely formed at 65° C. When agar was dissolved in 500 mM acetic acid, agarooligosaccharides were scarcely formed at 65° C. At 80° C. and 95° C., small amounts of agarooligoshaccharides were formed. When agar was dissolved in 1000 mM acetic acid, agarooligoshaccharides were scarcely formed at 65° C. At 80° C., a large amount of agarobiose was formed by heating for 24 hours, and small amounts of agarotetraose, agarohexaose and agarooctaose were formed by heating for 8 hours. At 95° C., a large amount of agarobiose formed by heating for 8 hors, and large amounts agarotetraose, agarohexaose and agarooctaose were also formed by heating for 8 hours.

(5) According to the same manner as that described in Example 10-(3), agarooligosaccharide formation in 60, 600 or 1200 mM lactic acid was measured.

As a result, when agar was dissolved in 60 mM lactic acid, small amounts of agarooligosaccharides were formed at 95° C., while agrooligosaccharides were scarcely formed at 65 and 80° C. When agar was dissolved in 600 mM lactic acid, large amounts of agarobiose were formed by heating at 80° C. for 8 to 24 hours, and large amounts of agarotetraose and agarohexaose were formed by heating for 4 to 8 hours. A large amount of agarooctaose was formed by heating for 4 hours. At 95° C., a large amount of agarobiose was formed by heating for 4 to 8 hours, and large amounts of agarotetoraose and agarohexaose were formed by heating for 2 to 6 hours. When agar was dissolved in 1200 mM lactic acid, a large amount of agarobiose was formed by heating at 80° C. for 4 to 24 hours, and large amounts of agarotetoraose and agarohexaose were formed by heating for 2 to 6 hours. A large amount of agarooctaose was formed by heating for 2 hours. At 95° C., a large amount of agarobiose was formed by heating for 2 to 8 hours, and large amounts of agarotetraose and agarohexaose were formed by heating for 1 to 2 hours.

Figure 22:
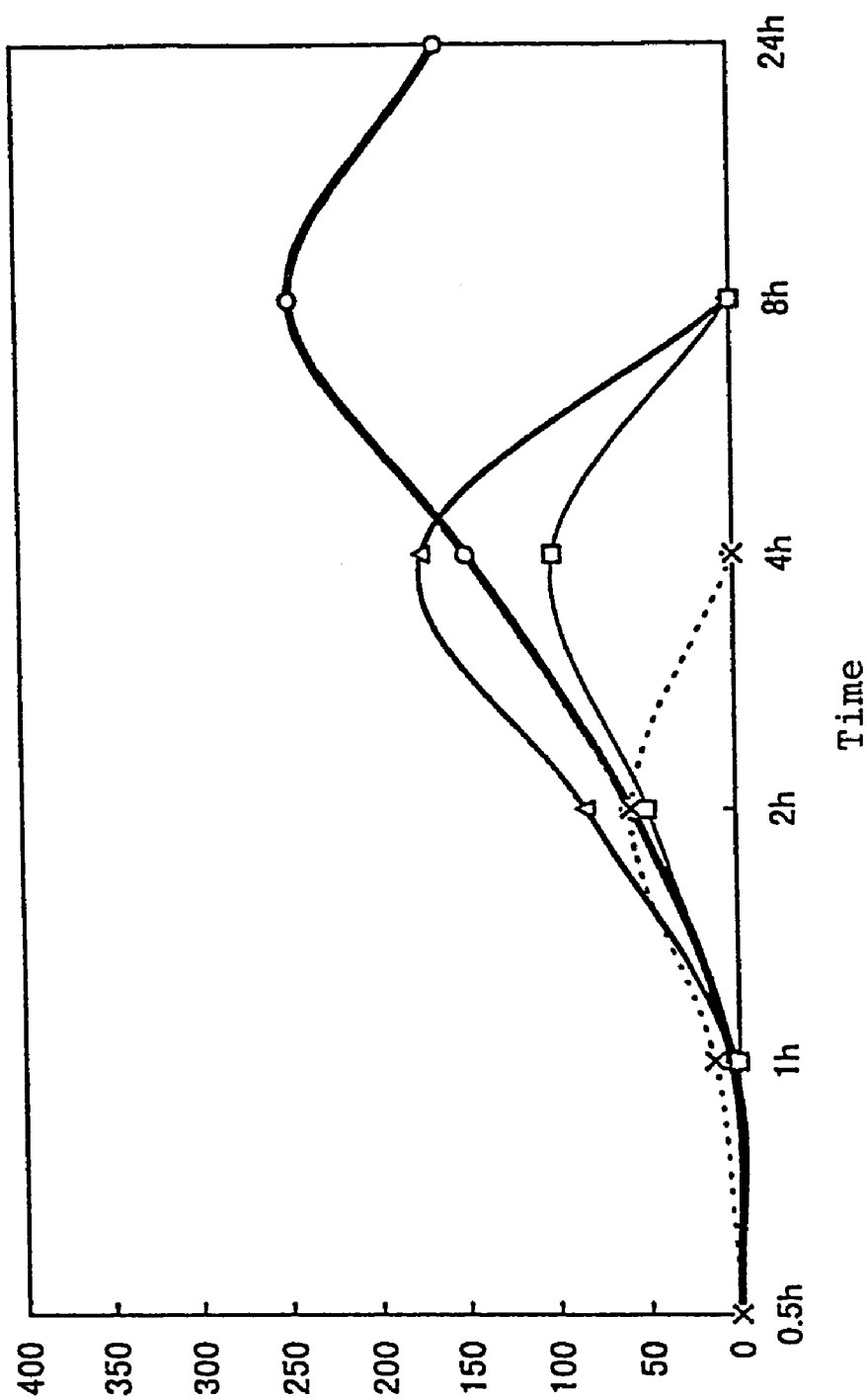
FIG. 22 illustrates the production of agarooligosaccharides in 1200 mM lactic acid at 80 C.
Figure 23:
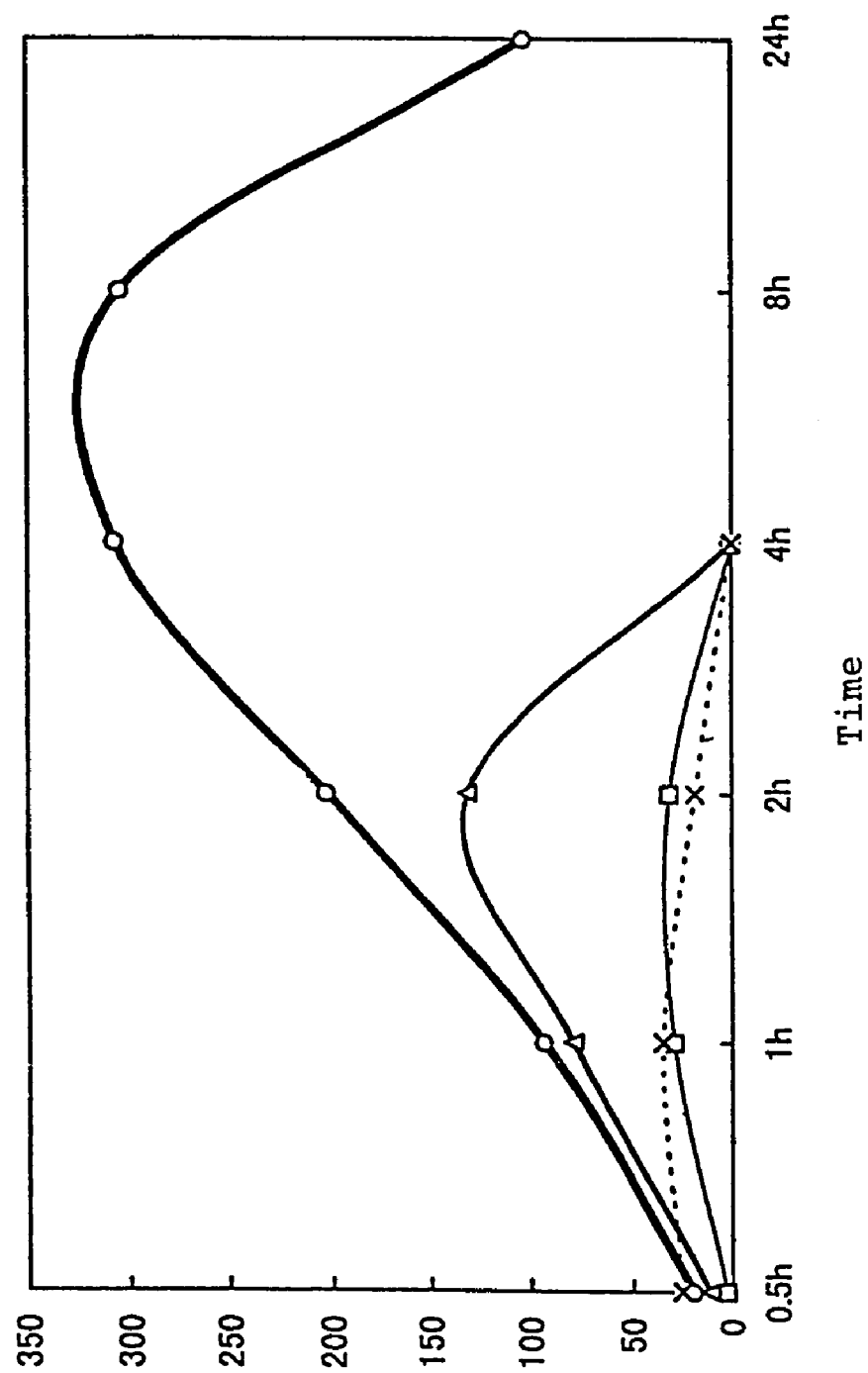
FIG. 23 illustrates the production of agarooligosaccharides in 1200 mM lactic acid at 95 C.

Examples of hydrolysis by 1200 mM lactic acid are shown in FIGS. 22 and 23. That is, FIG. 22 illustrates agarooligosaccharide formation in 1200 mM lactic acid by heating at 80° C. In FIG. 22, the vertical axis represents the amounts of agarooligosaccharides formed (open circle: agarobiose, open triangle: agarotetraose, open square: agarohexaose, symbol x: agarooctaose) and the horizontal axis represents the time. FIG. 23 illustrates agarooligosaccharide formation in 1200 mM citric acid by heating at 95° C. In FIG. 23, the vertical axis represents the amounts of agarooligosaccharides formed (open circle: agarobiose, open triangle: agarotetraose, open square: agarohexaose, symbol x: agarooctaose) and the horizontal axis represents the time.

(6) According to the same manner as that described in Example 10-(3), agarooligosaccharide formation in 20, 200, or 1000 mM malic acid was measured.

As a result, when agar was dissolved in 20 mM malic acid, small amounts of agarooligosaccharides were formed at 95° C., but agarooligosaccharides were scarcely formed at 65° C. and 80° C. When agar was dissolved in 200 mM malic acid, small amounts of agarooligosaccharides were formed by heating at 65° C. for 24 hours. At 80° C., a large amount of agarobiose was formed by heating for 8 to 24 hours, and a large amount of agarotetoraose was formed by heating for 4 to 8 hours. A large amount of agarohexaose was formed by heating for 4 hours. A large amount of agarooctaose was formed by heating for 4 hours. At 95° C., a large amount of agarobiose was formed by heating for 4 to 8 hours, and a large amount of agarotetraose was formed by heating for 4 hours. When agar was dissolved in 1000 mM malic acid, at 65° C., small amounts of agarooligosaccharides were formed by heating for 24 hours. At 80° C., a large amount of agarobiose was formed by heating for 2 to 24 hours, and a large amount of agarotetraose was formed by heating for 2 to 6 hours. Large amounts of agarohexaose and agarooctaose were formed by heating for 2 hours. At 95° C., a large amount of agarobiose was formed by heating for 1 to 8 hours, and a large amount of agarotetoraose was formed by heating for 1 to 2 hours. Large amounts of agarohexaose and agarooctaose were formed by heating for at 1 hour.

Figure 24:
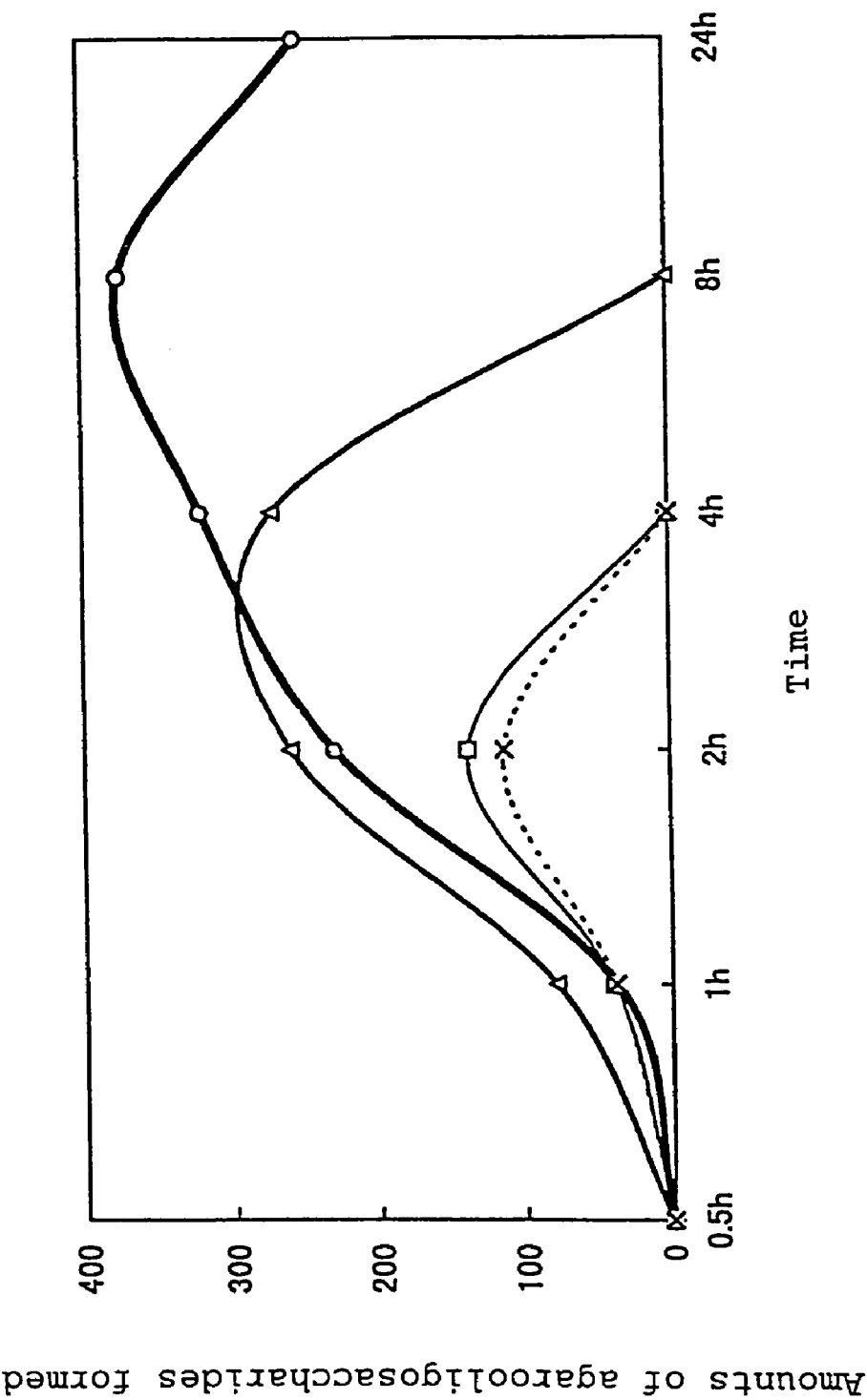
FIG. 24 illustrates the production of agarooligosaccharides in 1000 mM malic acid at 80 C.
Figure 25:
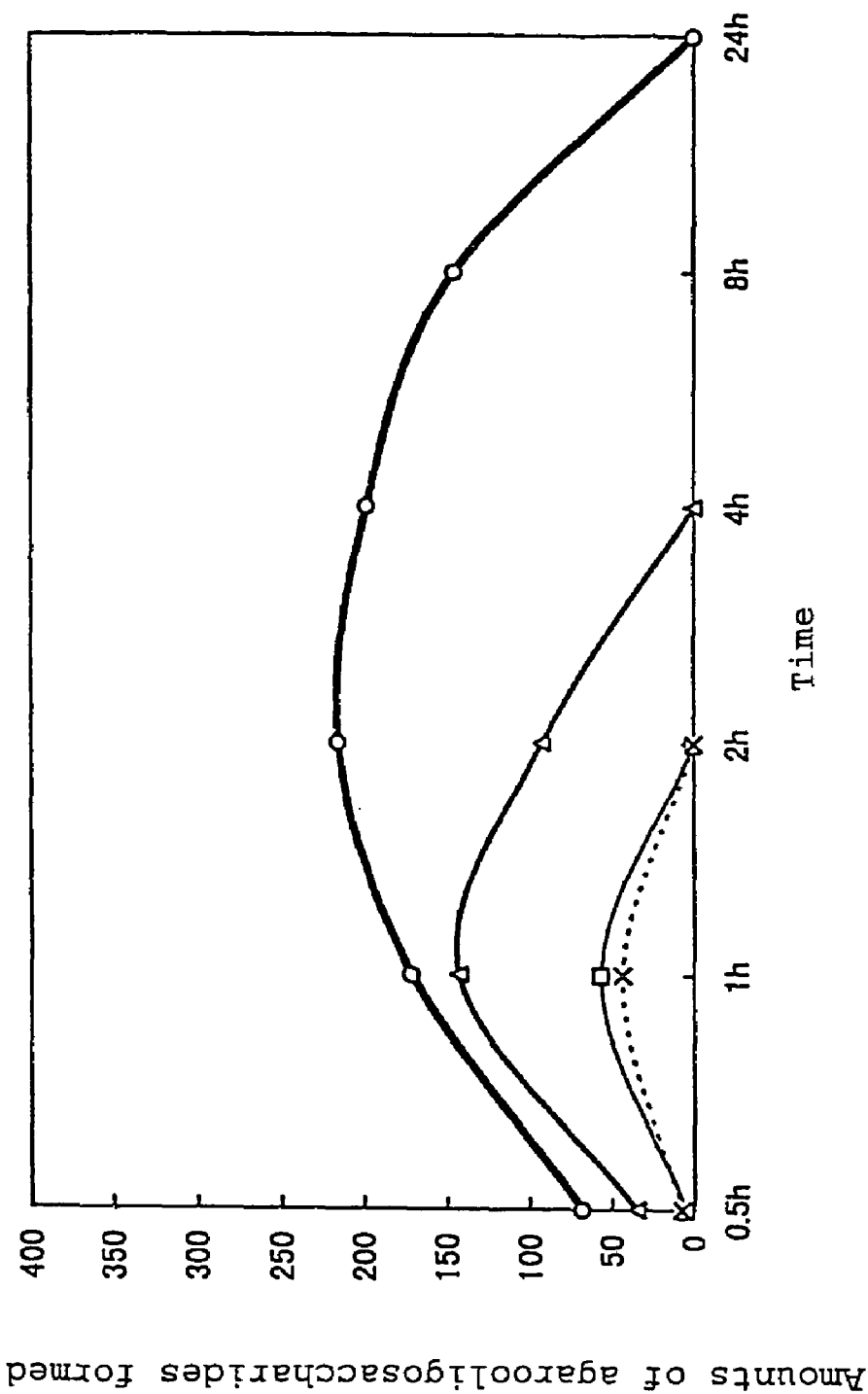
FIG. 25 illustrates the production of agarooligosaccharides in 1000 mM malic acid at 95 C.

Examples of hydrolysis by 1000 mM malic acid are shown in FIGS. 24 and 25. That is, FIG. 24 illustrates agarooligosaccharides formation in 1000 mM malic acid by heating at 80° C. In FIG. 24, the vertical axis represents the amounts of agarooligosaccharides formed (open circle: agarobiose, open triangle: agarotetraose, open square: agarohexaose, symbol x: agarooctaose) and the horizontal axis represents the time. FIG. 25 illustrates agarooligosaccharide formation in 1000 mM malic acid by heating at 95° C. In FIG. 25, the vertical axis represents the amounts of agarooligosaccharides formed (open circle: agarobiose, open triangle: agarotetraose, open square: agarohexaose, symbol x: agarooctaose) and the horizontal axis represents time.

(7) Noble agar was suspended in 100, 200, 300, 400, 500, 600, 700, 800, 900 or 1000 mM malic acid at a concentration of 10% and the suspensions were heated at 70, 80 or 90° C. Samples were obtained at 30 min., 1, 2, 3, 4, 8, or 24 hours after initiation of heating and, according to the same manner as that described in Example 10-(3), agarooligosaccharide formation was measured.

Figure 26:
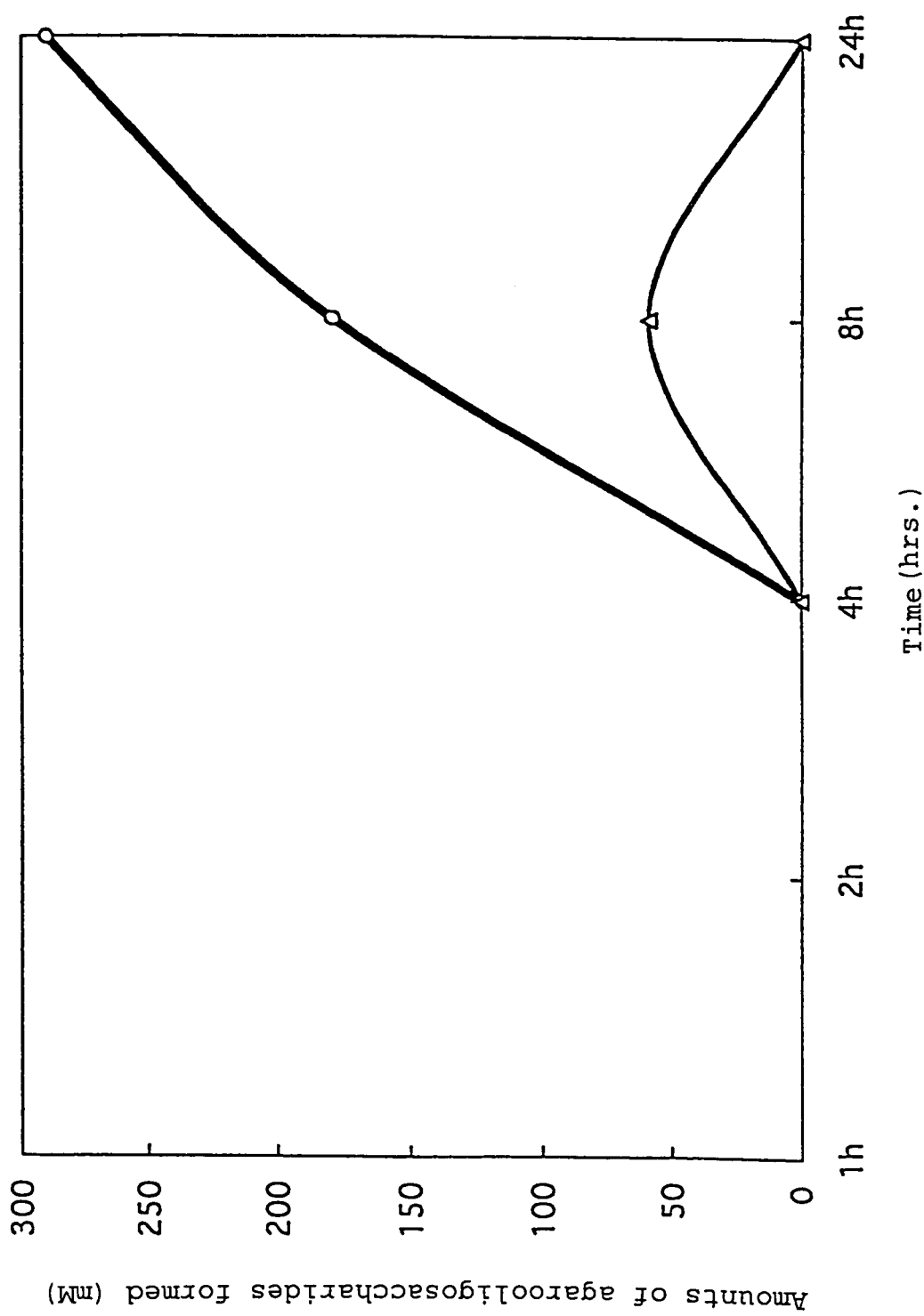
FIG. 26 illustrates the production of agarooligosaccharides in 1000 mM malic acid at 70 C.

At the malic acid concentration of 300 mM or more, large amounts of agarooligosaccharides were formed even by heating at 70° C. for 8 hours or longer. Examples of hydrolysis in 1000 mM malic acid at 70° C. are shown in FIG. 26. That is, FIG. 26 illustrates agarooligosaccharides formation in 1000 mM malic acid by heating at 70° C. In FIG. 26, the vertical axis represents the amounts of agarooligosaccharides formed (open circle: agarobiose, open triangle: agarotetraose) and the horizontal axis represents the time.

Based on the results of Example 10-(3) to (7) as described above, agarooligosaccharides are preferably produced by using an acid such as citric acid, lactic acid or malic acid at a concentration of several ten mM to several M and heating at 70 to 95° C. for several ten minutes to 24 hours.

(8) Agarobiose was determined using F-kit lactose/galactose (manufactured by Boehringer Mannheim, code 176303). In the above-mentioned method, agarobiose was determined by measuring the concentration of galactose generated from agarobiose by the action of β-galactosidase in F-kit.

The determination was carried out according to the instructions attached to the kit except that β-galactosidase was reacted at 37° C. for 1 hours. A calibration curve was prepared using lactose. A molar concentration (mM) was calculated in terms of lactose, which was then converted to agarobiose concentration (mg/ml).

According to the above method, the determination of agarobiose, agarotetraose, agarohexaose and agarooctaose prepared in the above-mentioned Example was tried. As a result, for agarobiose, the calculated value agreed with the actually determined value. On the other hand, agarotetraose, agarohexaose and agarooctaose were not substantially detected by the above-mentioned method. Namely, in practice, it was found that agarooligosaccharides except agarobiose were not detected by the above-mentioned method and that the agarobiose concentration in agarooligosaccharides can be measured using the above-mentioned method.

(9) A mixture of 100 g of commercially available agar (Ina agar type S-7: manufactured by Ina Shokuhin Kogyo) and 10 g of H-type strong cation exchange resin (Diaion SK104H: manufactured by Mitsubishi Chemical) was prepared by mixing them in 900 g of desalted water at 95° C. The mixture was stirred at 95° C. for 180 minutes to carry out acid decomposition of agar. Then, the resulting mixture was cooled to room temperature, filtrated by body feed of 1% w/w of activated carbon and 0.5% w/w of Celite 545 (manufactured by Celite) to obtain a filtrate.

According to the same manner as that described in Example 8-(2), the filtrate obtained was analyzed by normal phase HPLC to confirm that agarobiose, agarotetraose, agarohexaose and agarooctaose were mainly formed as agarooligosaccharides.

The filtrate was at pH 2.4, and it had the acidity of 1.7, the brix of 9.4% and the agarobiose content of 7.4% as measured by using F-kit lactose/galactose described in Example 10-(8).

(10) To 100 g of desalted water was added 18.5 g of H-type strong cation exchange resin (Daiyaion SK104H) and the mixture was stirred at 95° C. At 10 minutes intervals, 10 g of agar (Ina agar type S-7) was added 5 times, then 15 g of agar was added 2 times, 20 g of agar was added 3 times, and finally 30 g of agar was added. After adding a total of 185 g of agar, the mixture was stirred at 95° C. for 150 minutes and then cooled to room temperature. The resultant mixture was decanted to separate the resin from the liquid phase. Then, the separated liquid phase was filtrated by body feed of 3% w/w of activated carbon and 0.5% w/w of Celite 545 (manufactured by Celite) to obtain a filtrate.

According to the same manner as that described in Example 8-(2), the filtrate was analyzed by normal phase HPLC to confirm that agarobiose, agarotetraose, agarohexaose and agarooctaose were mainly formed as agarooligosaccharides.

The filtrate was at pH 1.2 and it had the acidity of 11.9, the brix of 64% and the agarobiose content of 24.4% as measured by using F-kit lactose/galactose described in Example 10-(8).

(11) Liquefaction of agar was carried out by preparing a suspension containing 100 g of commercially available agar (Ina agar type S-7) in deionized water having various phosphoric acid concentrations added to a volume of 1 liter, and stirring the resultant suspension at 95° C.

According to the same manner as that described with respect to the suspension containing phosphoric acid, liquefaction of agar was carried our by preparing a suspension containing agar in deionized water containing 1% w/v citric acid added to a volume of 1 liter. The term "liquefaction" used herein means a state in which gelation does not take place even at a freezing point. Time required for achieving such a state (liquefaction time) was measured. In addition, agarobiose contents upon liquefaction and thereafter were measured by using F-kit lactose/galactose described in Example 10-(8). The results are shown in Tables 6 and 7.

TABLE 6

| Phosphate conc. (% w/v) | Liquefaction time (min.) | Time held at 95 C. (min.) | Agarobiose (g/l) |
|---|---|---|---|
| 0.2 | 150 | 150 | 2.57 |
|  |  | 180 | 3.80 |
|  |  | 300 | 7.97 |
| 0.3 | 120 | 120 | 4.88 |
|  |  | 180 | 7.07 |
|  |  | 300 | 13.90 |
| 0.5 | 110 | 110 | 6.09 |
|  |  | 180 | 8.48 |
|  |  | 300 | 21.40 |
| 1.0 | 90 | 90 | 7.58 |
|  |  | 120 | 18.80 |

TABLE 7

| Citric acid concentration (% W/V) | Liquefaction time (min.) | Time held at 95° C. (min.) | Agarobiose (g/liter) |
|---|---|---|---|
| 1.0 | 90 | 90 | 0.95 |
|  |  | 120 | 3.40 |
|  |  | 150 | 4.09 |
|  |  | 300 | 5.70 |
|  |  | 360 | 14.80 |

EXAMPLE 11

(1) A mixture of 150 g of commercially available agar (Ina agar type S-7, manufactured by Ina Shokuhin Kogyo) and 15 g of citric acid (anhydrate) for food additives (manufactured by San-Ei Gen F.F.I. was made up to 1.5 liter with deionized water. The mixture was warmed to 92° C. and then held at 92-95° C. for 130 minutes with stirring. Then, the mixture was cooled to room temperature and filtrate by body feed of 0.5% of Celite 545 (manufactured by Celite) to obtain a filtrate (agar decomposition oligosaccharide solution). According to the same manner as that described in Example 8-(2), the filtrate obtained was analyzed by normal phase HPLC to confirm that agarobiose, agarotetraose, agarohexaose and agarooctaose were mainly formed as saccharaide compounds.

The filtrate was at about pH 2.6 and it had the acidity of 0.92, the brix of 9.2% and the agarobiose content of 43.1 mM as measured by the method described in Example 10-(8).

(2) The filtrate (agar decomposition oligosaccharide solution) prepared in Example 11-(1) was diluted 20-folds and to this were added acidulant, sweetener and flavor to prepare soft drinks containing 2.25 mM agarobiose.

The formulations are shown in Tables 8 and 9. Table 8 shows the formulation of a grapefruit soft drink and Table 9 shows the formulation of perilla flavored soft drink.

The components shown in each table were added to water and dissolved to prepare the soft drink, and the soft drink was distributed in 200 ml cans. The soft drink shown in Table 8 was carbonated to prepare a carbonated drink whose gas pressure was 0.8 kg/cm² (20° C.).

The analytical values for each drink are shown in the lower columns of Tables 8 and 9.

TABLE 8

| Agar decomposition oligosaccharide solution | 50 ml |
|---|---|
| ½ grapefruit | 20 g |
| Vitamin C | 0.2 g |
| Citric acid | 0.2 g |
| Maltose | 1.25 g |
| Grapefruit flavor | 1 g |
| Desalted water | rest |
| Total | 1000 ml |
| pH | 3.2 |
| Acidity* | 0.23 |
| Brix | 2.2 |

Acidity*: 0.1 N NaOH ml/10 ml (hereinafter the same)

TABLE 9

| Agar decomposition oligosaccharide solution | 50 ml |
|---|---|
| Perilla extract | 20 g |
| Vitamin C | 0.2 g |
| Citric acid | 0.2 g |
| Perilla flavor | 0.5 g |
| Desalted water | rest |
| Total | 1000 ml |
| pH | 2.9 |
| Acidity* | 0.10 |
| Brix | 0.6 |

Each carbonated drink of the present invention was assessed by 10 panelists in a sensory test which scores in five grades (5: good, 1: bad). As a control, a soft drink prepared by using an aqueous citric acid solution having the same acidity instead of the agar decomposition oligosaccharide solution was used.

The average scores obtained in the sensory test for the grapefruit tasted ones and those for the perilla flavored ones are shown in Tables 10 and 11.

TABLE 10

|  | Product of the present invention | Control |
|---|---|---|
| Texture |  |  |
| mildness | 4.6 | 3.1 |
| smoothness | 4.8 | 3.0 |
| Flavor balance | 4.5 | 2.9 |
| General assessment | 4.6 | 3.1 |

TABLE 11

|  | Product of the present invention | Control |
|---|---|---|
| Texture |  |  |
| mildness | 4.5 | 2.5 |
| smoothness | 4.3 | 2.4 |
| Flavor balance | 4.2 | 2.5 |
| General assessment | 4.3 | 2.4 |

As compared with the control, the products of the present invention were assessed to have better flavor balance as well as milder and smoother texture. Thus, the products are drinks having novel tastes. Likewise, the soft drinks without carbonation of the present invention had novel tastes.

(3) Ethyl alcohol was added to each of the soft drinks described in Tables 8 and 9 at ethyl alcohol concentrations of 6% v/v or 8% v/v and the resulting mixtures were distributed in 200 ml cans. The alcohol drinks were carbonated to prepare the carbonated alcohol drinks of the present invention in which gas pressure was 0.8 kg/cm$^2$ (20° C.).

As compared with the control which did not contain the agar decomposition oligosaccharide solution, the carbonated alcohol drinks of the present invention were to have better flavor balance as well as milder and smoother texture. Thus, the carbonated alcohol drinks of the present invention had novel tastes.

EXAMPLE 12

(1) A drink containing an agar decomposition product decomposed by citric acid was prepared as follows. The formulation is shown in Table 12. Namely, for Product 1 of the present invention in Table 12, 0.1% w/v of the filtrate prepared in Example 11-(1) (agar oligosaccharide solution), 0.25% w/v of agar (Ultra Agar AX-30: manufactured by Ina Shokuhin Kogyo) and 0.07% w/v of citric acid were used. For Product 2 of the present invention, 0.25% w/v of agar and 0.08% w/v of citric acid were used without addition of the agar oligosaccharide solution. In either case of Products 1 and 2 of the present invention, the drinks containing the agar decomposition products decomposed by citric acid were prepared by dissolving agar with hot water, mixing it with the other components and heating under acidic conditions at 93° C. for 10 seconds, at 93-80° C. for 20 minutes and at 80-75° C. for 15 minutes. On the other hand, a control was prepared according to the same formulation as that of Product 2 of the present invention except that heating was carried out at 93° C. for 10 seconds.

Each drink with thickness containing the agar decomposition product decomposed by citric acid was assessed by 10 panelists in a sensory test which scores in five grades (5: good, 1: bad). The mean scores obtained in the sensory test are shown in Table 13.

TABLE 12

|  | Product 1 | Product 2 |
| --- | --- | --- |
| Agar (g) | 2.5 | 2.5 |
| Agar oligosaccharide solution (ml) | 1.0 | 0 |
| ½ grapefruit juice (g) | 1.5 | 1.5 |
| Granulated sugar (g) | 66.0 | 66.0 |
| Citric acid (g) | 0.7 | 0.8 |
| Sodium citrate (g) | 0.5 | 0.5 |
| Flavor (g) | 2.0 | 2.0 |
| Desalted water | rest | rest |
| Total | 1000 ml | 1000 ml |
| pH | 3.68 | 3.67 |
| Acidity* | 1.53 | 1.57 |
| Brix | 7.5 | 7.4 |
| Agarobiose (mM)** | 0.06 | 0.02 |

Agarobiose (mM)** was measured by the method described in Example 10-(8).

TABLE 13

|  | Product 1 | Product 2 | Control |
| --- | --- | --- | --- |
| Texture |  |  |  |
| mildness | 4.4 | 4.1 | 3.6 |
| smoothness | 4.5 | 4.3 | 3.8 |
| Flavor balance | 4.4 | 4.2 | 3.6 |
| General assessment | 4.5 | 4.3 | 3.7 |

As compared with the control, Products 1 and 2 of the present invention were assessed to have better flavor balance, suitable thickness as well as milder and smoother texture. Thus, the products were drinks with novel tastes. The formation of an oligosaccharide for an antioxidant, agarobiose, by heat treatment in the presence of citric acid added in Products 1 and 2 of the present invention was recognized. Thus, the novel drinks containing an oligosaccharides for an antioxidant were provided.

According to the same manner as that described in Example 10-(8), a mounts of agarobiose formed were measured using heating conditions at 75° C. for 1 day; at 85° C. for 5 minutes; at 103° C. for 5 minutes; or at 122° C. for 45 seconds in stead of 80-75° C. for 15 minutes. As a result, it was confirmed that the amounts of agarobiose formed were 0.03 mM, 0.02 mM, 0.04 mM and 0.05 mM, respectively, that agarobiose was formed by heat treatment, and that the more severe the heating conditions became, the more agarobiose was formed.

(2) Ethyl alcohol was added to Product 1 and Product 2 of the present invention, and the control described in Example 12-(1) at ethyl alcohol concentration of 2% v/v or 4% v/v. The total volume was adjusted by reducing the volume of desalted water which corresponds to that of ethyl alcohol added. Thus, alcohol drinks were prepared.

As compared with the control, the alcohol drinks corresponding to Products 1 and 2 were assessed to have better flavor balance, suitable thickness as well as milder and smoother texture. Thus, the products were drinks having novel taste.

Additionally, frozen products of the above-described alcohol drinks exhibited good sherbet-like texture.

EXAMPLE 13

(1) Commercially available agar (Agar Noble) was suspended in 0.1 N hydrochloric acid at a concentration of 1% and the suspension was treated at 37° C. for 5 hours, 16 hours or 48 hours. The suspension thus treated was diluted 10-folds with distilled water and analyzed with thin layer chromatography as described in Example 9. As a result, the formation of small amounts of agarooligosaccharides was observed by the treatment for 5 hours. The amounts thereof were increased by the treatment for 16 hours and were further increased by the treatment for 48 hours.

(2) Commercially available agar (Agar Noble) was suspended in a phosphate buffered saline or distilled water at a concentration of 1% and the suspension was heated at 121° C. for 4 hours. The suspension thus heated was diluted 10-folds with distilled water and analyzed with thin layer chromatography as described in Example 9. As a result, the formation of trace amounts of agarooligosaccharides was observed in the sample heat-treated in the phosphate buffered saline. In the sample heat-treated in distilled water, the formation of clearly more amounts of agarooligosaccharides was observed. The former was at about pH 7 after the heat treatment, while the latter was at about pH 5. After cooling to room temperature, the former gelated but the latter did not.

EXAMPLE 14

(1) Agar (Agar Noble) was suspended in 0.1N HCl at a concentration of 10% and heated at 100° C. for 19 minutes. TOYOPEARL HW40C (manufactured by Toso) column (4.4 cm×85 cm) was equilibrated with water and 10 ml of the above-mentioned sample was applied to this column. Gel filtration chromatography was carried out using water as a mobile phase at a flow rate of 1.4 ml/min. The eluted substances were detected using a differential refractometer and each 7 ml fraction was collected.

Peaks were recognized at elution time 406, 435, 471 and 524 minutes. The analysis of the fractions corresponding to respective peaks with thin layer chromatography as described in Example 9 demonstrated that these were agarooctaose, agarohexaose, agarotetraose and agarobiose in this order. The fractions were lyophilized to obtain 30 mg agarooctaose, 100 mg agarohexaose, 150 mg agarotetraose and 140 mg agarobiose.

(2) Agarobiose and agarohexaose obtained in Example 14-(1) were dissolved in water to prepare 100 mM aqueous solutions thereof. To each 25 µl of these solutions was added 50 µl of 100 mM aqueous L-cysteine solution, followed by addition of 925 µl of phosphate buffered saline. Then, the mixture was treated at 37 C for 1 hour or 16 hours. The same reaction was repeated except that an aqueous solution containing the same concentration of L-lysine was used instead of the aqueous L-cysteine solution.

1 µl of a sample from each reaction was spotted on a silica gel sheet 60 $F_{254}$, developed with 1-butanol:ethanol:water=5: 5:1 and detected by orcinol-sulfate method.

As a result, the spots of agarobiose and agarotetraose were disappeared in the sample from the reaction for 1 hours with L-cysteine. In the samples from the reaction for 16 hours with L-cysteine and L-lysine, the spots of agarobiose and agarotetraose were disappeared.

When each sample was analyzed with normal phase HPLC as described in Example 8-(2), the results were consistent with those obtained with the thin layer chromatography.

(3) According to the same manner as that described in Example 2-(1), an antiproliferation activity against HL-60 cells was measured by placing 10 µl of each sample from the reaction prepared in Example 14-(2) into a well of a 96 well microtiter plate.

As a result, it was observed that the activities were disappeared in the sample whose spots of agarobiose and agarotetraose were disappeared. Namely, antiproliferation activities in the samples from the reaction of agarobiose and agarotetraose with L-cysteine for 1 hour and from the reaction of agarobiose and agarotetraose with L-cysteine or L-lysine for 16 hours were reduced to about 1/10 relative to the same concentrations of agarobiose and agarotetraose.

EXAMPLE 15

(1) A suspension of 2.5 g of κ-carrageenan (manufactured by Sigma, C-1263) in 50 ml of 0.1 N HCl was heated at 100 C for 16 minutes. The resultant solution was cooled to room temperature, neutralized to about neutral pH with NaOH, filtrated through Cosmonice filter and separated with normal phase HPLC as follows.

Figure 27:
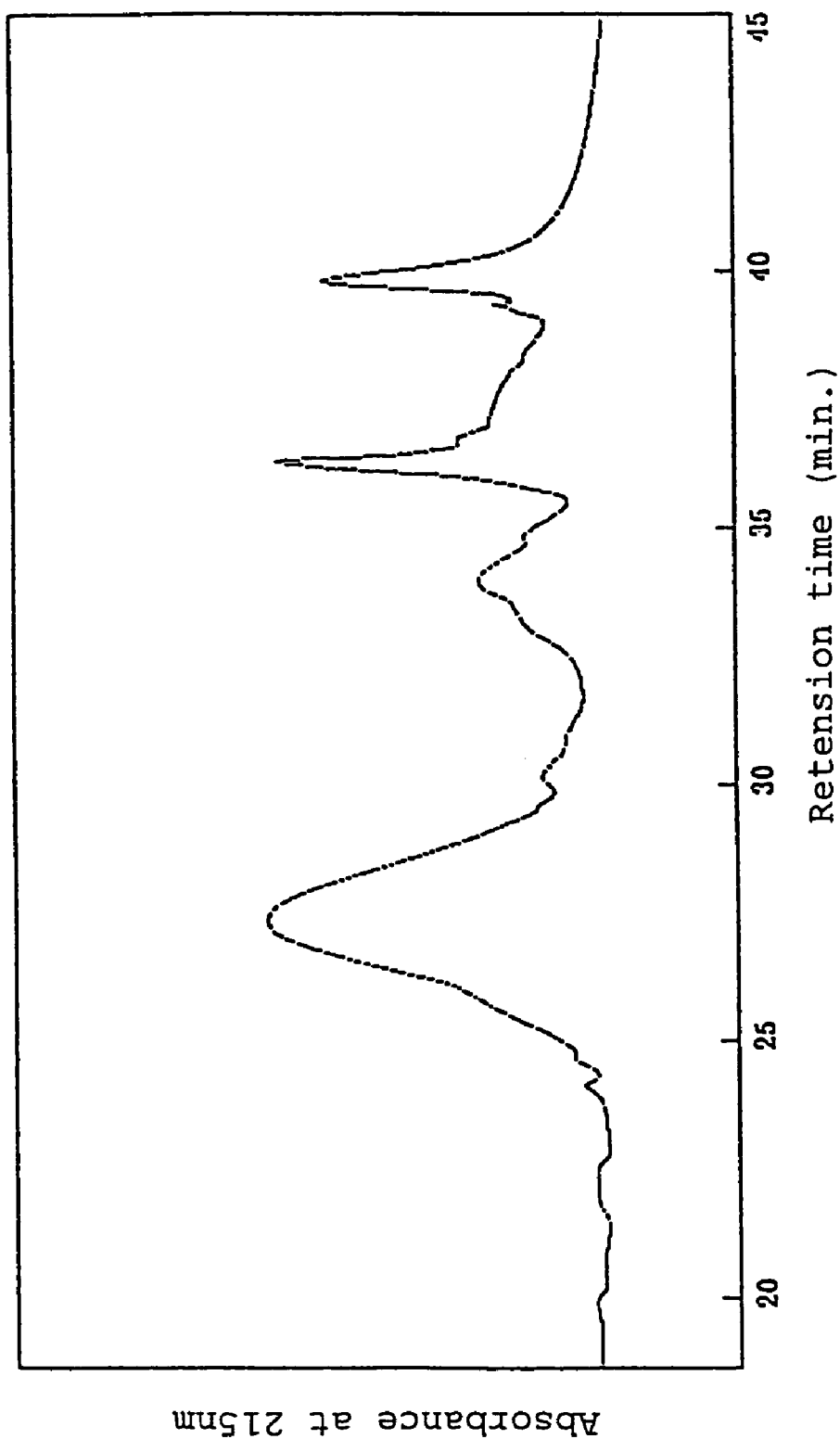
FIG. 27 illustrates a normal phase HPLC chromatogram of κ-carrageenan decomposed with an acid.

Column: PALPAK type S (4.6×250 mm, manufactured by Takara Shuzo, CA8300)
Solvent A: aqueous 90% acetonitrile solution
Solvent B: aqueous 50% acetonitrile solution
Flow rate: 1 ml/min.
Elution: solvent A (10 minutes) linear gradient from solvent A to solvent B (40 minutes) solvent B (10 minutes)
Detection: absorbance at 215 nm
Column temperature: 40° C.
Amount of sample applied: 50 µl The separation pattern of normal phase HPLC is shown in FIG. 27. That is, FIG. 27 illustrates normal phase HPLC chromatogram of acid decomposition product of κ-carrageenan. The horizontal axis represents the retention time (min.) and the vertical axis represents the absorbance at 215 nm.

Each elution peak was fractionated, collected, evaporated to dryness under reduced pressure and dissolved in 100 µl of water. Each fraction was sterilized by filtration and, according to the same manner as that described in Example 2-(1), an antiproliferation activity against HL-60 cells was measured. As a result, in groups to which the fractions from peaks at 27.797, 33.905 to 34.784, and 36.226 to 36.654 min. were added, apoptosis corpuscles were observed. The absorbance at 590 nm thereof was lower than that of the control group to which water was added, and cell proliferation was inhibited.

The fraction from the peak at elution time 27.797 min. was separated 12 times under the above-mentioned HPLC conditions and the fractions were combined and evaporated to dryness under reduced pressure to obtain an apoptosis-inducing and carcinostatic substance.

(2) Mass spectrometry of the apoptosis-inducing and carcinostatic substance described in Example 15-(1) was carried out using DX302 mass spectrometer (manufactured by Nippon Denshi). Glycerol was used as a matrix and the measurement was performed with negative ion mode.

FAB-MS
m/z 403 [M–H]⁻
495 [M+glycerol–H]⁻

Figure 28:
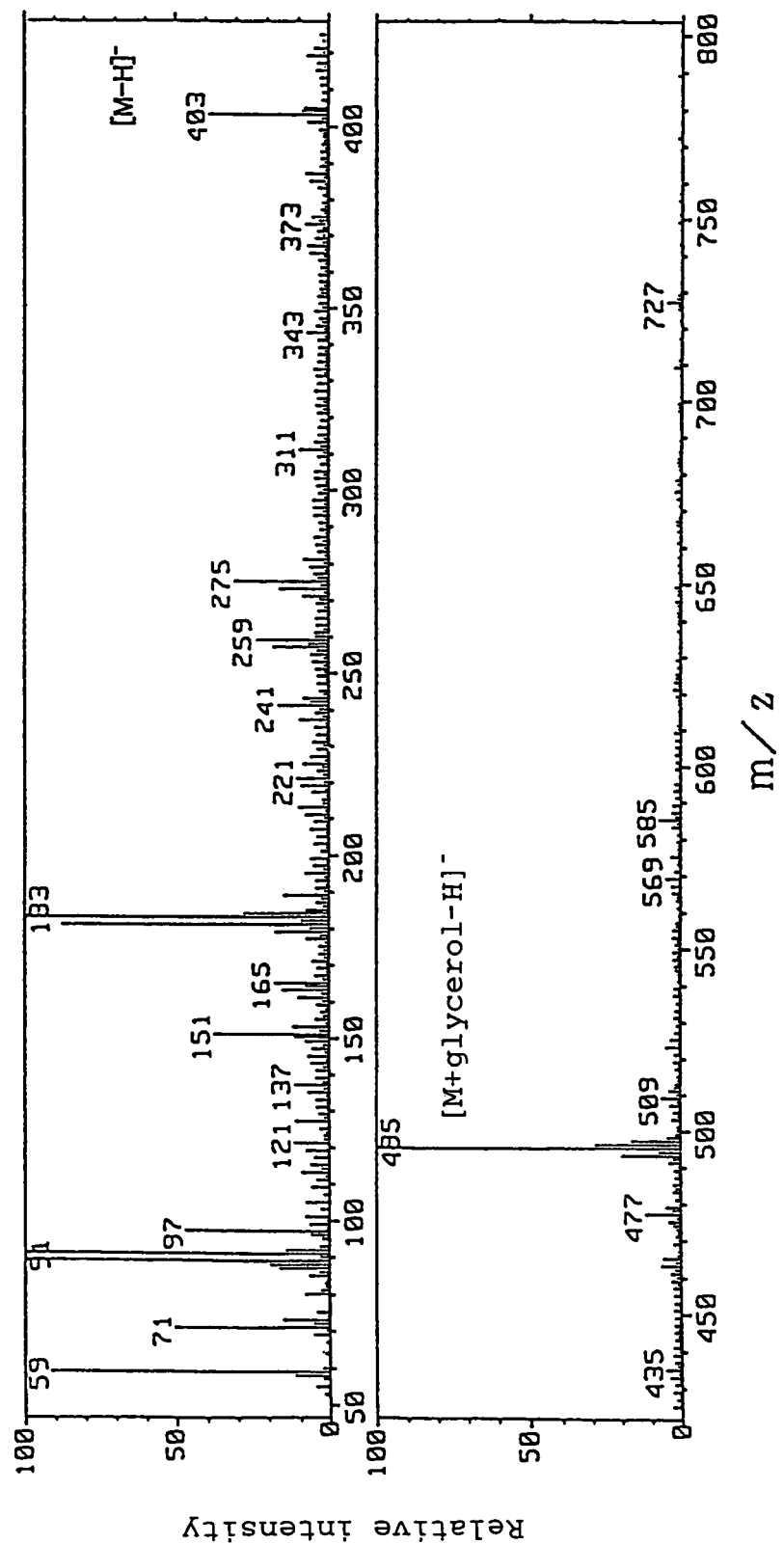
FIG. 28 illustrates a mass spectrum of an apoptosis-inducing and carcinostatic substance.

The results are shown in FIG. 28. That is, FIG. 28 illustrates mass spectrum of the apoptosis-inducing and carcinostatic substance. The horizontal axis represents the m/z value and the vertical axis represents the relative intensity.

A nuclear magnetic resonance spectrum of the apoptosis-inducing and carcinostatic substance obtained in Example 15-(1) was measured with JNM-A500 nuclear magnetic resonance apparatus (manufactured by Nippon Denshi).

Figure 29:
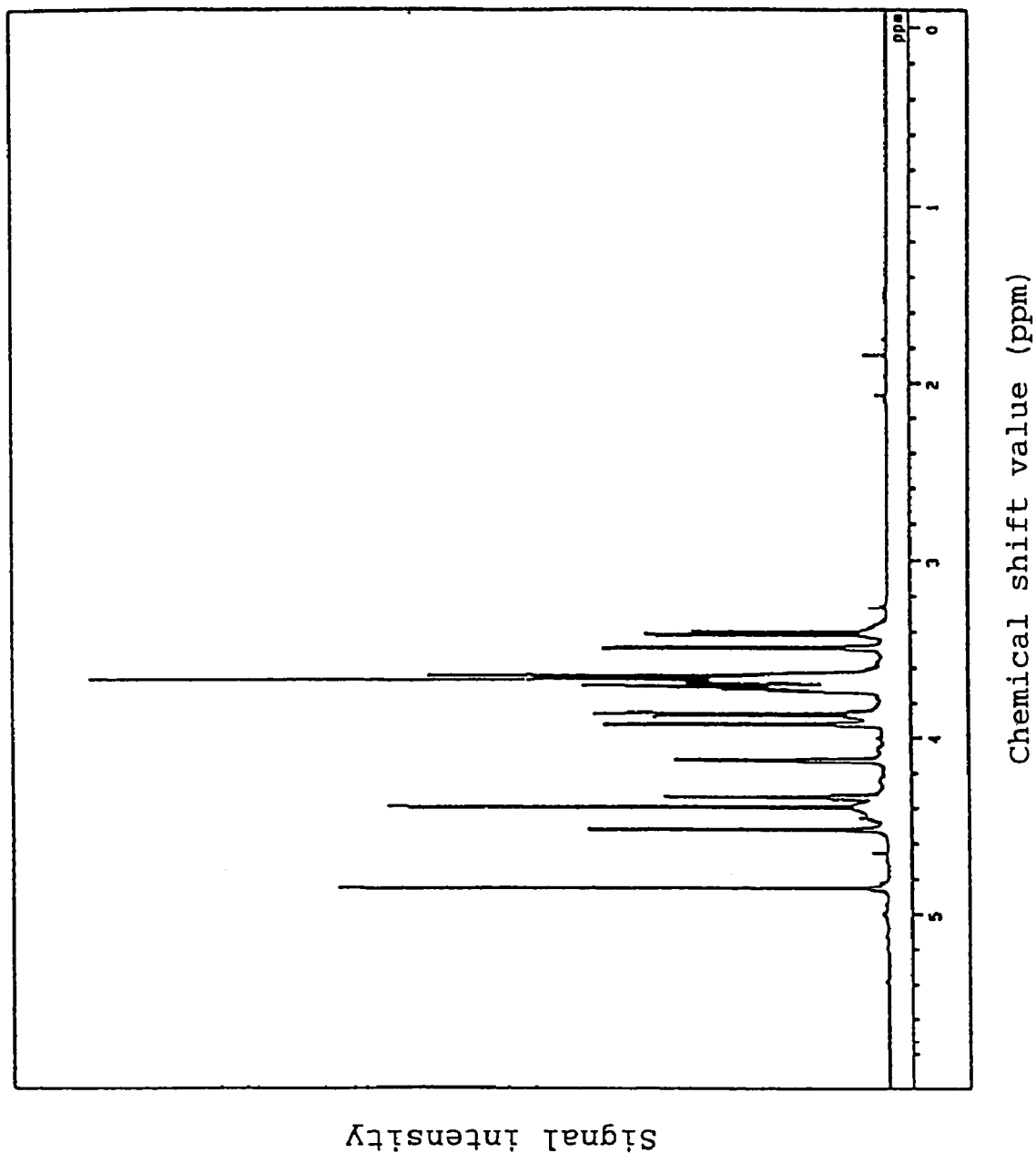
FIG. 29 illustrates a $^1$H-NMR spectrum of an apoptosis-inducing and carcinostatic substance.

In FIG. 29, ¹H-NMR spectrum of the apoptosis-inducing and carcinostatic substance is shown. In FIG. 29, the horizontal axis represents the chemical shift value and the vertical axis represents the signal intensity.

Based on these analytical results of mass spectrometry and ¹H-NMR, the apoptosis-inducing and carcinostatic substance described in Example 15-(1) was identified as κ-carabiose [β-D-galactopyranosyl-4-sulfate-(1  4)-3,6-anhydro-D-galactose].

In view of the above, it has been found that the apoptosis-inducing and carcinostatic substance obtained in Example 15-(1) is κ-carabiose.

(3) κ-Carabiose obtained in Example 15-(1) was dissolved in water at a concentration of 1.56 mM, 10 µl of the solution was placed in a well of a 96 well microtiter plate and, according to the same manner as that described in Example 2-(1), an apoptosis-inducing activity and an antiproliferation activity were measured. As a result, apoptosis corpuscles were observed under an optical microscope and, as compared with a control group to which water was added, cell proliferation in the group to which κ-carabiose was added was suppressed by about 70%. Therefore, κ-carabiose induced apoptosis in HL-60 cells and inhibited cell proliferation at 156 μM.

EXAMPLE 16

(1) A suspension of 4.5 g of commercially available agar powder (manufactured by Wako Pure Chemical Industries, Ltd.) in 150 ml of 0.1 N HCl was heated with a microwave oven. The resultant solution was held on a boiling bath for 10 minutes. After heating, the solution was allowed to cool to room temperature and insoluble materials were removed by centrifugation. The supernatant was then collected and adjusted to pH 6.8 with 1 N sodium hydroxide. To 150 ml of the supernatant was added the equal volume of ethyl acetate, and the mixture was stirred vigorously and partitioned between the ethyl acetate phase and the aqueous phase. The partitioned aqueous phase was evaporated to dryness with an evaporator and the residue was dissolved in 150 ml of water again. Insoluble materials were removed by centrifugation to obtain a supernatant. The ethyl acetate phase was evaporated to dryness with an evaporator, dissolved in 100 ml of ion-exchanged water and adjusted to pH 6.5 with 1 N sodium hydroxide.

The ethyl acetate phase and the aqueous phase were sterilized by filtration with a filter of 0.2 μm pore size (manufactured by Corning), diluted 10-, 20- and 30-folds with water and, according to the same manner as that described in Example 2-(1), an antiproliferation activity against HL-60 cells was measured. As a result, an antiproliferation activity was observed in the aqueous phase, but was not in the ethyl acetate phase.

Figure 30:
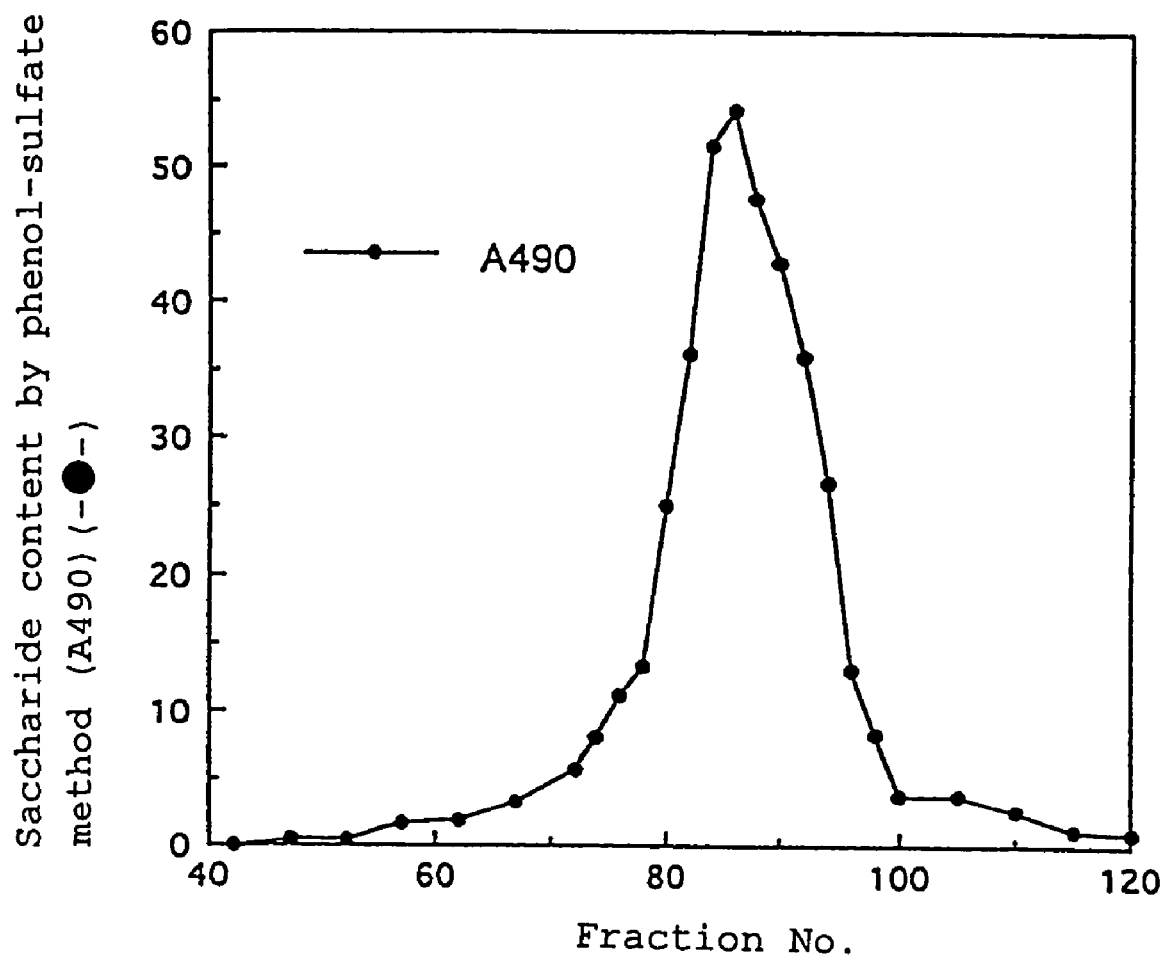
FIG. 30 illustrates the results of gel filtration with Cellulofine GCL-25.

50 ml of the aqueous phase solution thus prepared was subjected to gel filtration with Cellulofine GCL-25 column (41×905 mm). The eluent was 0.2 M NaCl containing 10% ethanol. The elution pattern is shown in FIG. 30. That is, FIG. 30 illustrates the results of gel filtration with Cellulofine GCL-25 column. In FIG. 30, the vertical axis represents the saccharide content in the eluate measured by phenol-sulfuric acid method (absorbance at 490 nm: closed circle) and the horizontal axis represents the fraction number (10 ml/fraction).

1 μl of each eluted fraction was spotted on a silica gel sheet 60 $F_{254}$ (manufactured by Merck) and developed with 1-butanol:acetic acid:water=4:1:2. Orcinol reagent [prepared by dissolving 400 mg of orcinol monohydrate (manufactured by Wako Pure Chemical Industries, Ltd.) in 22.8 ml of sulfuric acid and adding thereto water to make the total volume up to 200 ml] was sprayed and the sheet was heated on a hot plate heated at 150 C to observe the spots.

Every 5 fractions of Fraction Nos. 40 to 120 whose spots were confirmed by the above-mentioned TLC analysis were combined and sterilized by filtration. Then, an antiproliferation activity against HL-60 cells was measured. As a result, Fraction Nos. 86 to 90 had the strongest antiproliferation activity.

Figure 31:
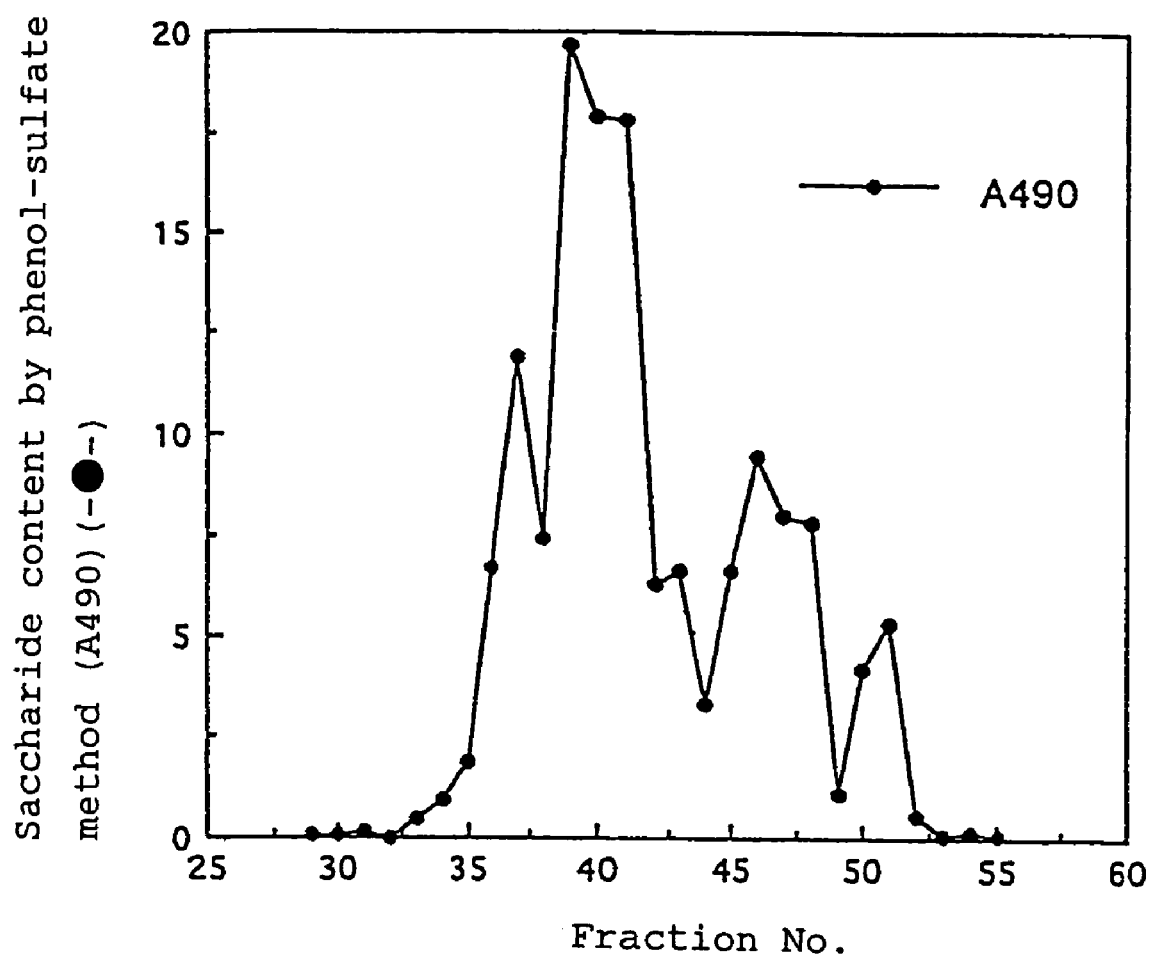
FIG. 31 illustrates the results of gel filtration with a Sephadex LH-20 column.

(2) Fraction Nos. 86 to 88 were recovered, and evaporated to dryness with an evaporator to obtain 0.94 g of powder. The powder obtained was dissolved in 30 ml of 90% ethanol, and then white precipitate was removed using 5C filter (manufactured by ADVANTEC). The resultant was subjected to gel filtration with Sephadex LH-20 column (35×650 mm). The eluent was 90% ethanol. The elution pattern was shown in FIG. 31. That is, FIG. 31 illustrates the results of gel filtration with Sephadex LH-20 column. In FIG. 31, the vertical axis represents the saccharide content in the eluate measured by phenol-sulfuric acid method (absorbance at 490 nm: closed circle) and the horizontal axis represents the fraction number (10 ml/fraction).

Each eluate fraction was analyzed with a silica gel sheet as described above.

Components detected by TLC analysis were roughly divided into five groups, i.e., Fraction Nos. 30 to 35, 36 to 40, 41 to 44, 45 to 48 and 49 to 53. For each group, 125 μl portions from the respective fractions of the group were combined and evaporated to dryness with an evaporator. The residue was dissolved in 500 μl of ion-exchanged water and its antiproliferation activity against HL-60 cells was measured.

Fraction Nos. 36 to 40 which had the strongest antiproliferation activity against HL-60 cells were evaporated to dryness with an evaporator, and dissolved in 5 ml of 1-butanol: acetic acid:water=4:1:2. The solution was applied to column (20×710 mm) packed with silica gel 60 $F_{254}$ and washed with 1-butanol:acetic acid:water=4:1:2. As the eluent, 1-butanol: acetic acid:water=4:1:2 was used (3 ml/fraction).

Each eluted fraction was analyzed by using a silica gel sheet as described above. As a result, components detected were roughly divided into five groups as follows: Fraction Nos. 46 to 52 (group 1), 60 to 70 (group 2), 72 to 84 (group 3), 86 to 94 (group 4) and 96 to 120 (group 5).

Each group was evaporated to dryness with an evaporator, dissolved in 5 ml of ion-exchanged water and filtrated through a filter having pore size of 0.45 μm (manufactured by IWAKI). An antiroliferation activity against HL-60 cells of each solution obtained was measured. As a result, an antiproliferation activity was observed in the groups 3, 4 and 5.

Regarding the structure of the substance contained in the groups 4 and 5, it was confirmed to be agarobiose by TLC analysis and mass spectrometry.

Figure 32:
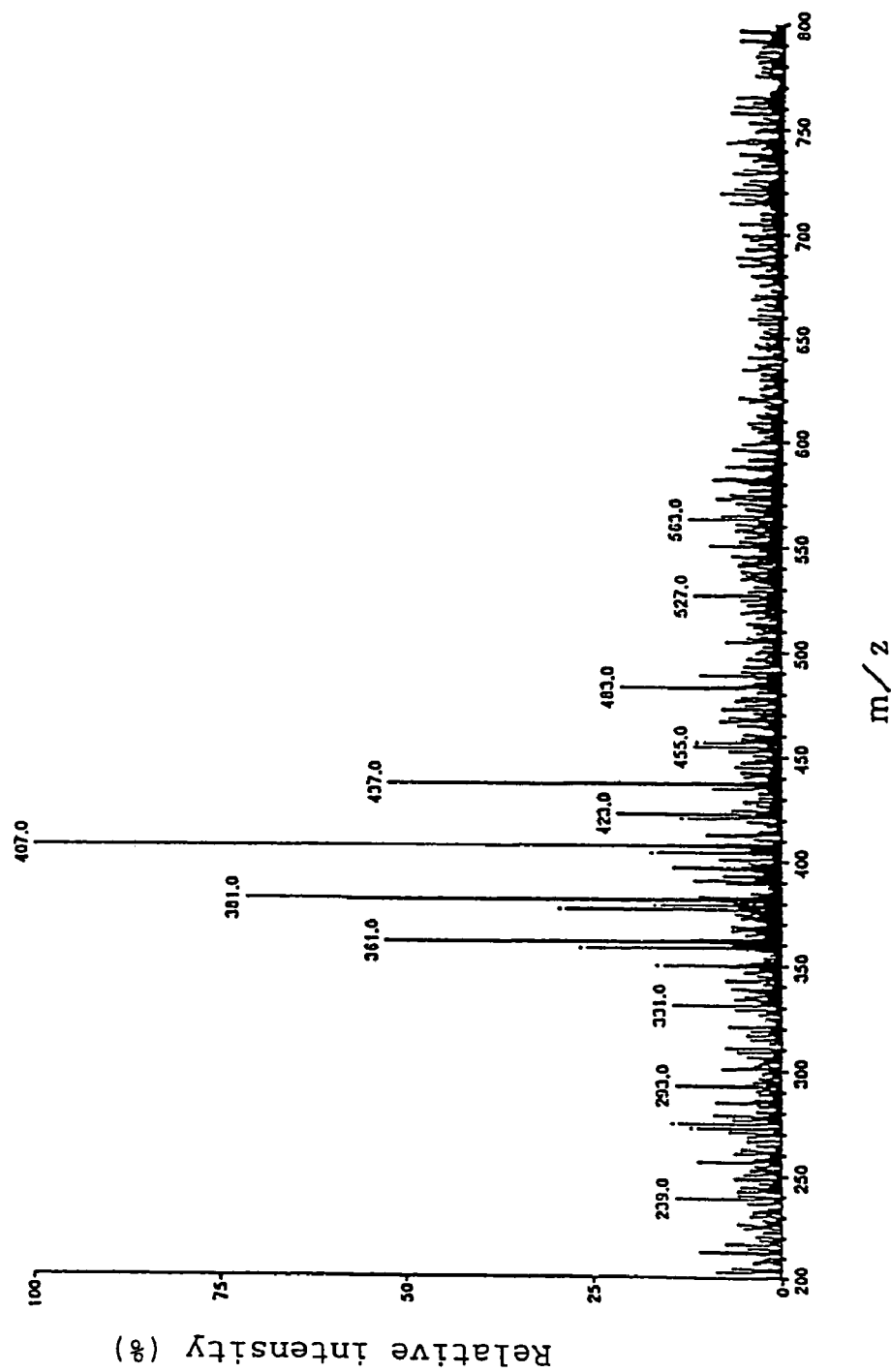
FIG. 32 illustrates a mass spectrum of β-D-galactopyranosyl-(1 4)-3,6-anhydro-2-O-methyl-L-galactose.
Figure 33:
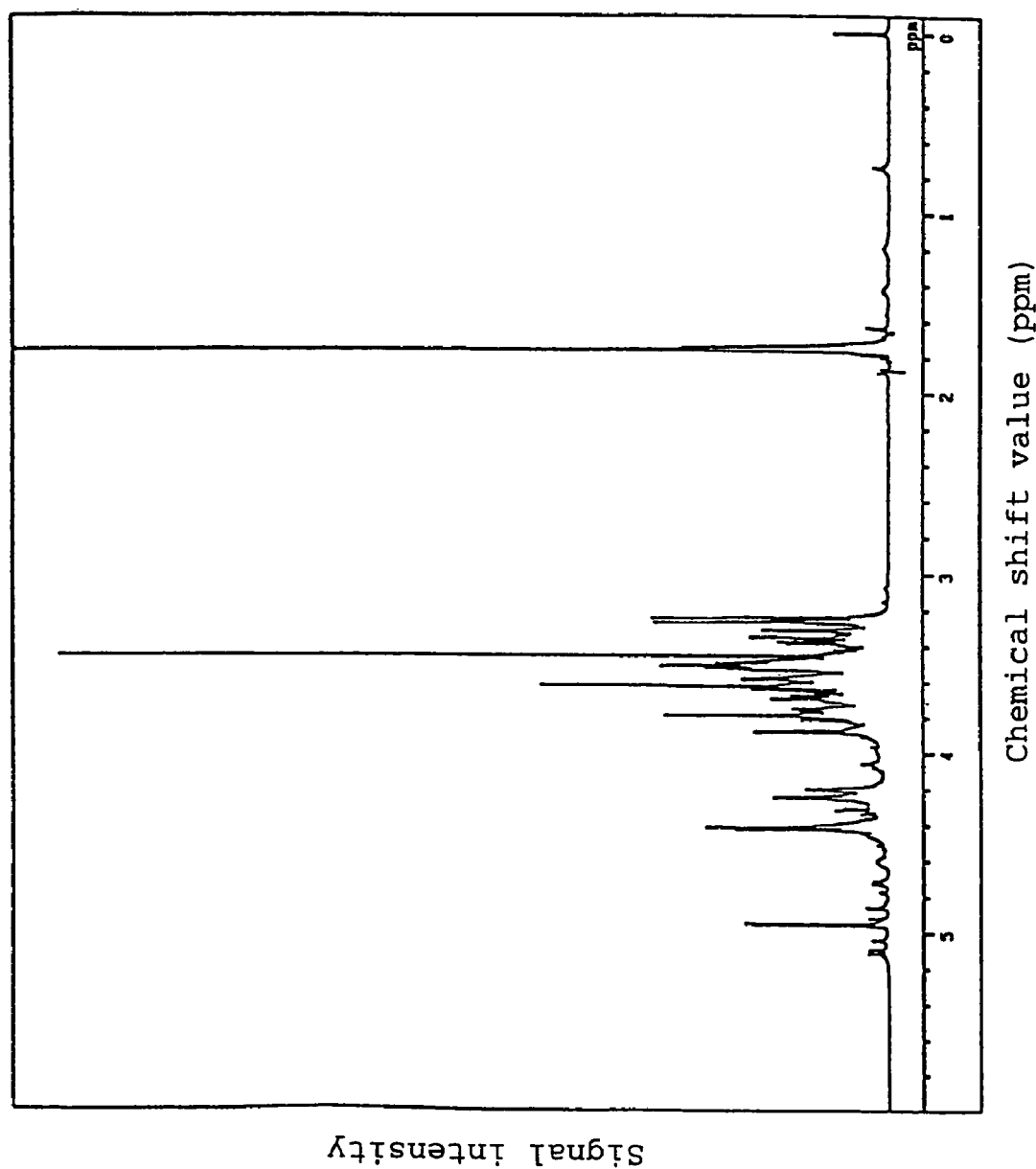
FIG. 33 illustrates a $^1$H-NMR spectrum of β-D-galactopyranosyl-(1 4)-3,6-anhydro-2-O-methyl-L-galactose.

As for the structure of the substance contained in the group 3, it was confirmed to be β-D-galactopyranosyl-(1 4)-3,6-anhydro-2-O-methyl-L-galactose by mass spectrometry and NMR analysis. FIG. 32 illustrates the mass spectrum of β-D-galactopyranosyl-(1 4)-3,6-anhydro-2-O-methyl-L-galactose. The horizontal axis represents the m/z value and the vertical axis represents the relative intensity (%). And, FIG. 33 illustrates the $^1$H-NMR spectrum of be β-D-galactopyranosyl-(1 4)-3,6-anhydro-2-O-methyl-L-galactose. The horizontal axis represents the chemical shift value (ppm) and the vertical axis represents the signal intensity (%).

It was found that, like agarobiose, β-D-galactopyranosyl-(1 4)-3,6-anhydro-2-O-methyl-L-galactose had a strong antiproliferation activity against HL-60 cells.

EXAMPLE 17

(1) Inhibitory activity of the saccharides derived from agar obtained in Example 3 against lipid peroxide radical production was measured as follows.

*Staphylococcus aureus* 3A (National Collection Of Type Culture, NCTC 8319) was inoculated into 5 ml of brain heart infusion medium (manufactured by Difco, 0037-17-8) and cultured at 37° C. overnight. The bacterial cells were collected by centrifugation, washed with phosphate buffered saline 3 times and then suspended in phosphate buffered saline at a concentration of 1×10$^7$ colony forming units/ml. A mixture of 100 μl of the cell suspension, 100 μl of an aqueous sample solution, 100 μl of aqueous 1 mg/ml methemoglobin (manufactured by Sigma M9250) solution, 600 μl of phosphated buffered saline and 100 μl of aqueous 50 mM tert-butyl hydroperoxide (manufactured by Katayama Kagaku, 03-4990) solution were reacted at 37 C for 30 minutes. To the reaction mixture was added 1 ml of 2×NMP medium [prepared by dissolving 8 g of nutrient broth (manufactured by Difco, 0003-01-6), 5 g of trypton (manufactured by Difco, 0123-17-3), 5 g of NaCl, 10 g of mannitol (manufactured by Nacalai Tesque, 213-03) and 0.035 g of phenol red (manufactured by Nacalai Tesque, 268-07) in distilled water to make the volume up to 500 ml. The pH was adjusted to 7.5 with NaOH and then the mixture was sterilized by filtration] to stop the reaction. The resultant mixture was diluted every 3-folds with NMP medium (prepared by diluting 2×NMP medium 2-folds with sterilized water) to prepare 12 serial dilutions and 160 μl of each dilution was placed in each well of a 96-well microtiter plate. The plate was incubated at 37 C overnight. Color of the medium was observed with the naked eye and the sample contained in a well in which the color of the medium changed from red to yellow by growth of the bacterium was identified as that having an activity of inhibiting lipid peroxide radical production.

The results are shown in Table 14. In Table 14, + represents the sample in which the growth of the bacterium was observed, and − represents the sample in which the growth of the bacterium was not observed. The concentration shown in the uppermost line of the table is that of the sample in the reaction mixture in which the sample was reacted with tert-butyl hydroperoxide and the bacterial cells at 37° C. for 30 minutes.

TABLE 14

|  | 0.1 mM | 1 mM |
|---|---|---|
| Agarobiose | + | + |
| Agarotetraose | − | + |
| Galactose | − | − |

As seen from the above results, a strong activity of inhibiting lipid peroxide radical production was found in agarobiose and agarotetraose. Similar activity was confirmed in carabiose and 3,6-anhdro-2-O-methyl-L-galactose.

(2) A suspension of 5 g of commercially available agar (Ina agar type S-7, manufactured by Ina Shokuhin Kogyo) in 45 ml of 50 mM citric acid was heated at 93° C. for 155 minutes and adjusted to pH 6 with NaOH to prepare a sample (citric acid treated sample). Likewise, a suspension of the same agar in 45 ml of 100 mM hydrochloric acid was heated at 95° C. for 13 minutes and adjusted to pH 6 with NaOH to prepare a sample (hydrochloric acid treated sample). Both samples were diluted with water to give 1-, 2-, 4-, 8-, 10- and 100-fold dilutions and, according to the same manner as that described in Example 17-(1), an activity of inhibiting lipid peroxide radical production inhibitory activity thereof was determined. As a result, in both of the citric acid treated sample and the hydrochloric acid treated sample, the activity was confirmed up to 10-fold dilutions and both had equivalent activities of inhibiting lipid peroxide radical production.

EXAMPLE 18

Inhibitory activity of agarobiose against lymphocyte blastgenesis induced by Concanavalin A (Con A)

A spleen was taken out from a ddY mouse (Nippon SLC; male, 7 weeks old), finely minced and suspended in RPMI-1640 medium (Gibco) containing 10% fetal bovine serum (HyClone) to obtain a single cell suspension. The cell suspension was seeded into a plastic Petri dish, incubated at 37° C. for 2 hours in a carbon dioxide incubator. Adhesive cells adhered to the Petri dish were removed and non-adhesive cells were used as spleen lymphocytes. 200 μl of 2×10$^6$ cells/ml spleen lymphocytes suspension was seeded into each well of 96 well microtiter plate. Agarobiose at varying concentration was added to the wells other than the control well. Furthermore, to all the wells was added 5 μg of Con A (Nacalai Tesque) and the plate was incubated at 37° C. for one day in a carbon dioxide incubator. After incubation, 1 μCi of $^3$H-thymidine was added to each well and incubation was continued for additional one day. Then, its uptake into cells was measured using a liquid scintillation counter.

Figure 34:
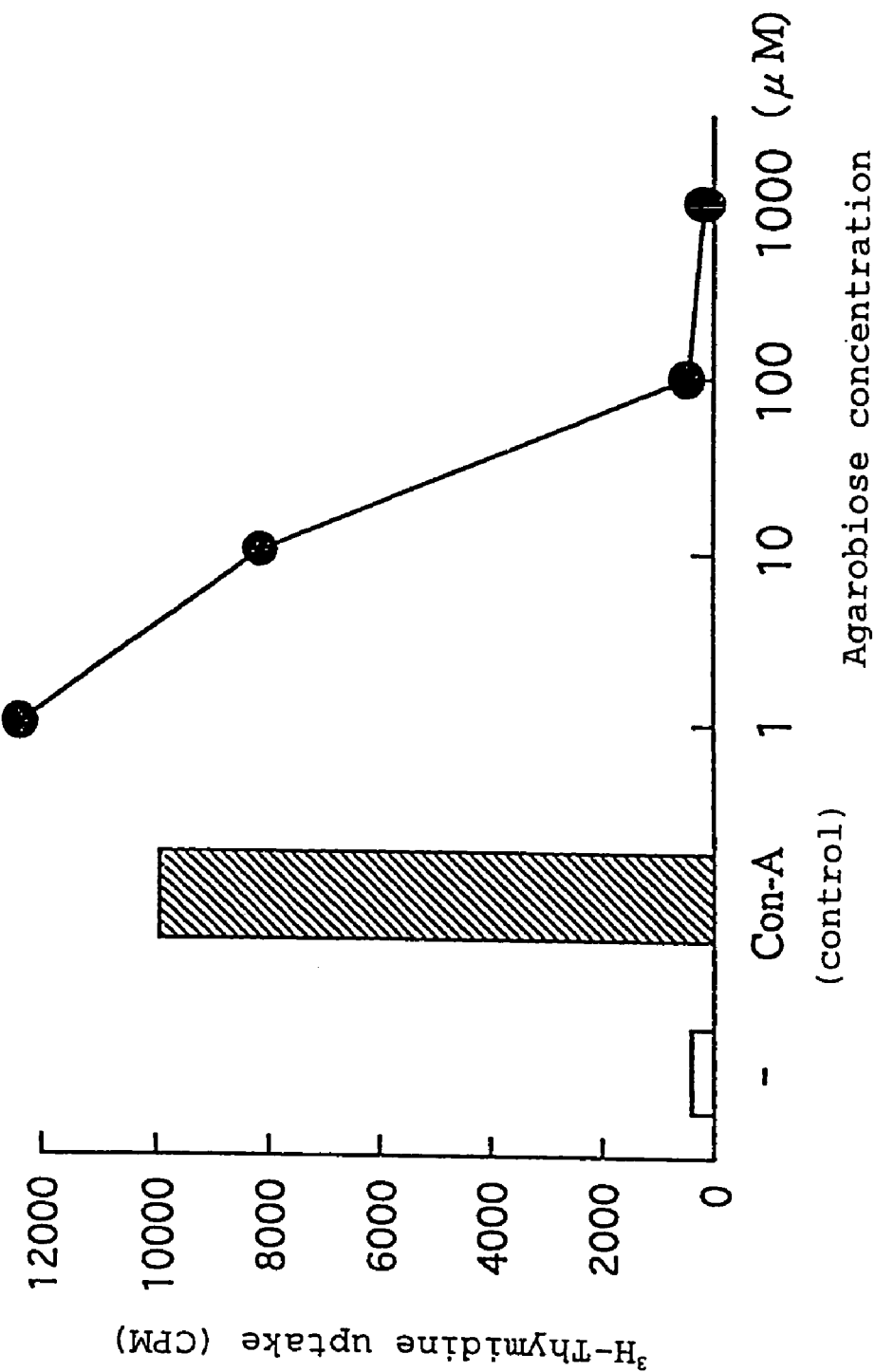
FIG. 34 illustrates the relation between the concentration of agarobiose and the level of $^3$H-thymidine uptake in lymphocyte blastgenesis induced by ConA.

The results are shown in FIG. 34. FIG. 34 illustrates the relation between the agarobiose concentration and the $^3$H-thymidine uptake in lymphocyte blastgenesis induced by Con A. The horizontal axis represents the agarobiose concentration and the vertical axis represents the $^3$H-thymidine uptake (cpm). The open bar and the shaded bar represent the $^3$H-thymidine uptake without stimulation and with stimulation by Con A, respectively. As seen from FIG. 34, agarobiose exhibits the dose-dependent inhibitory activity against mouse lymphocyte proliferation stimulated by mitogen, and almost completely inhibits the proliferation at 100 μg/ml. Thus, the inhibitory activity of agarobiose against lymphocyte activation has been recognized. For 3,6-anhydrogalactopyranose, agarotetraose, agarohexaose, agarooctaose, carabiose and 3,6-anhydro-2-O-methyl-L-galactose, similar activities have also been recognized.

EXAMPLE 19

Inhibitory activity of agarobiose against mixed lymphocyte reaction.

Spleens were taken out from a BALB/c mouse (Nippon SLC; male, 6 weeks old) and a C57BL/6 mouse (Nippon SLC; male, 6 weeks old) and spleen lymphocytes were obtained by the above-described method. Each cell suspension was adjusted to a concentration of 2×10$^6$ cell/ml, 100 μl portions from respective suspensions were mixed together and seeded in a 96 well microtiter plate. Agarobiose at varying concentration was added to the wells other than the control well, and the plate was incubated at 37 C for 4 days in a carbon dioxide incubator. After incubation, 1 μCi of $^3$H-thymidine was added to each well, and the plate was incubated for additional 1 day. Its uptake into cells was measured using a liquid scintillation counter.

Figure 35:
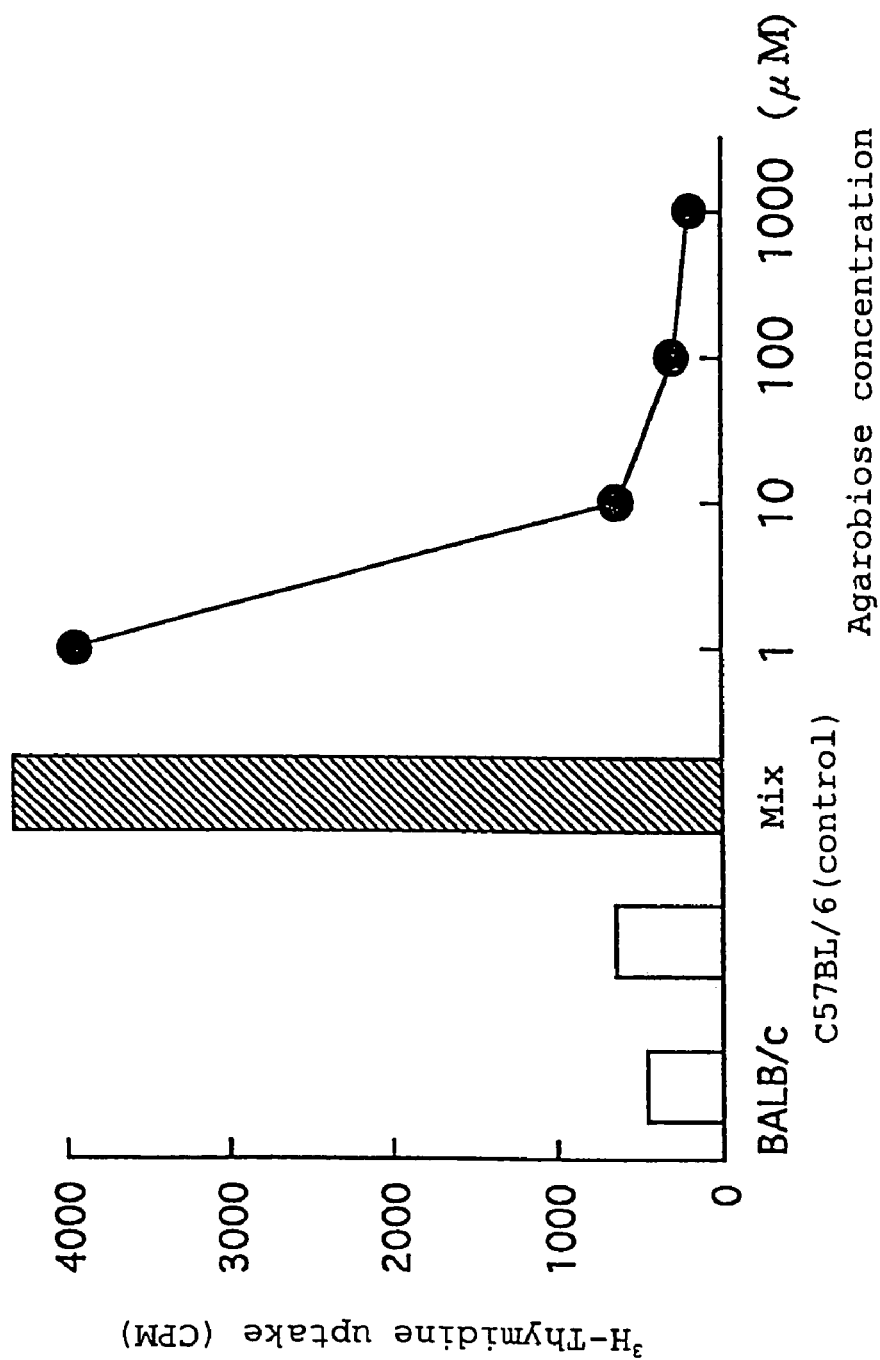
FIG. 35 illustrates the relation between the concentration of agarobiose and the level of $^3$H-thymidine uptake in a mixed lymphocyte reaction.

The results are shown in FIG. 35. That is, FIG. 35 illustrates the relation between the agarobiose concentration and the $^3$H-thymidine uptake in the mixed lymphocyte reaction. The horizontal axis represents the agarobiose concentration and the vertical axis represents $^3$H-thymidine uptake (cpm). The open bar and the shaded bar represent $^3$H-thymidine uptake in case where cells from either one of the lines were used independently, and in case where mixed cells from both of the lines were used, respectively. As is seen from FIG. 35, agarobiose has the dose-dependent inhibitory activity against lymphocytes activation by stimulation with an alloantigen, and almost completely inhibits the lymphocytes activation at 10 μg/ml. Thus, the inhibitory activity against lymphocyte activation of agarobiose has been recognized. For 3,6-anhydrogalactopyranose, agarotetraose, agarohexaose, agarooctaose, carabiose and 3,6-anhydro-2-O-methyl-L-galactose, similar activities have also been recognized.

EXAMPLE 20

(1) RAW 264.7 cells (ATCC TIB 71) were suspended in phenol red-free Dulbecco's modified Eagle's medium containing 10% fetal bovine serum (manufactured by Gibco) and 2 mM L-glutamine (manufactured by Life Technologies Oriental, 25030-149) at a concentration of $3\times10^5$ cells/ml, and 500 µl portions thereof were seeded to respective wells of a 48-well microtiter plate and incubated at 37 C for 12 hours in the presence of 5% $CO_2$. To each well were added 10 µl of 25 µg/ml lipopolysaccharide (LPS, manufactured by Sigma, L-2012) and 10 µl of aqueous 5000, 1500, 500, 150 or 50 µM agarobiose or neoagarobiose (manufactured by Sigma, G4410) solution, and the plate was incubated for additional 12 hours. Then, concentration of $NO_2^-$ produced by oxidation of NO in the medium was measured. As control groups, a group to which LPS was not added and a group to which agarobiose or neoagarobiose was not added were provided.

After incubating as described above, 100 µl of 4% Greece reagent (manufactured by Sigma, G4410) was added to 100 µl of the medium, and the mixture was allowed to stand for 15 minutes at room temperature. Then, the absorbance at 490 nm was measured. $NO_2^-$ concentration in the medium was calculated with reference to a calibration curve prepared by using $NaNO_2$ at given concentrations dissolved in the same medium as that described above. All the measurements were carried out in triplicate.

Figure 36:
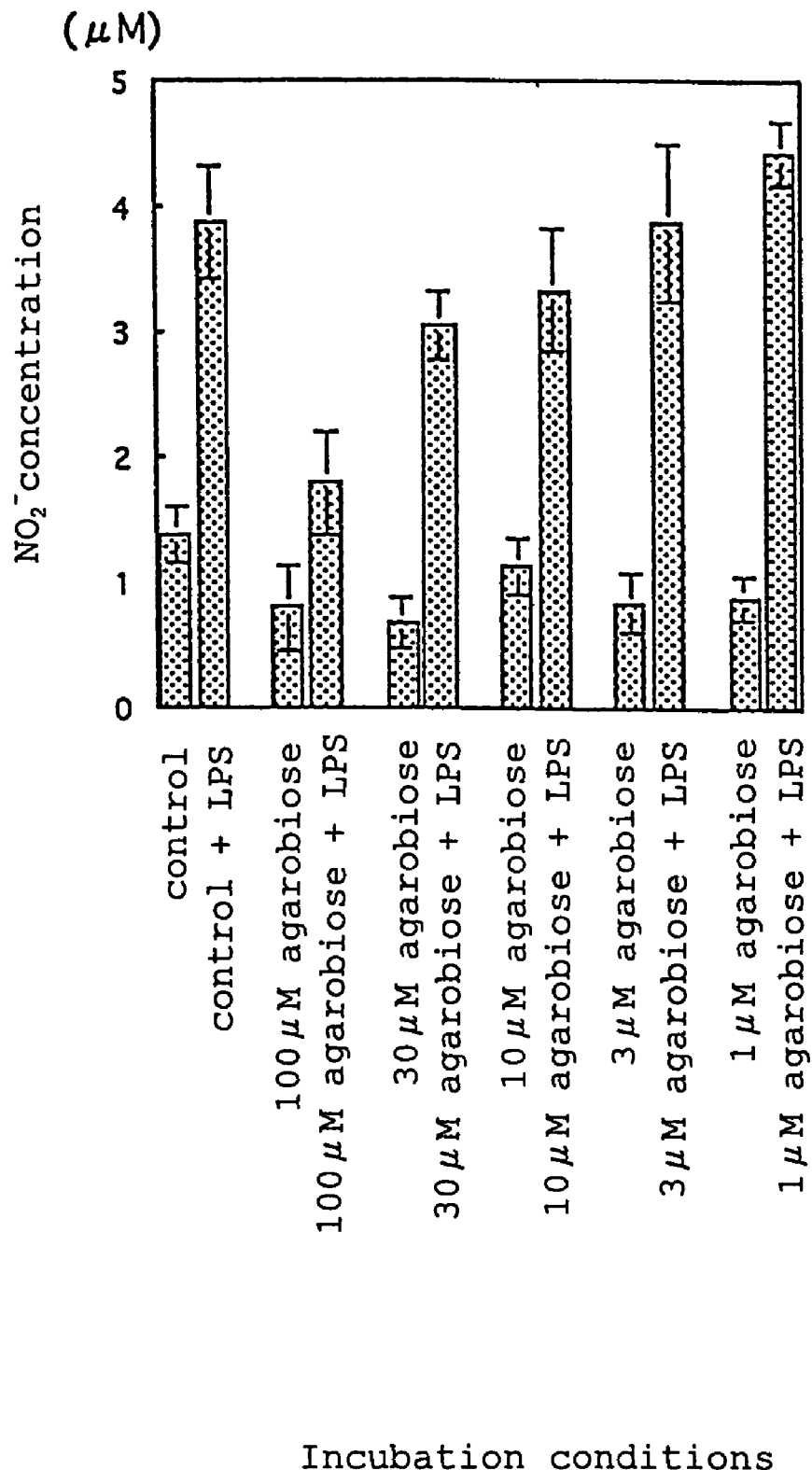
FIG. 36 illustrates $NO_2^-$ concentrations in culture media in the presence of various concentrations of agarobiose.
Figure 37:
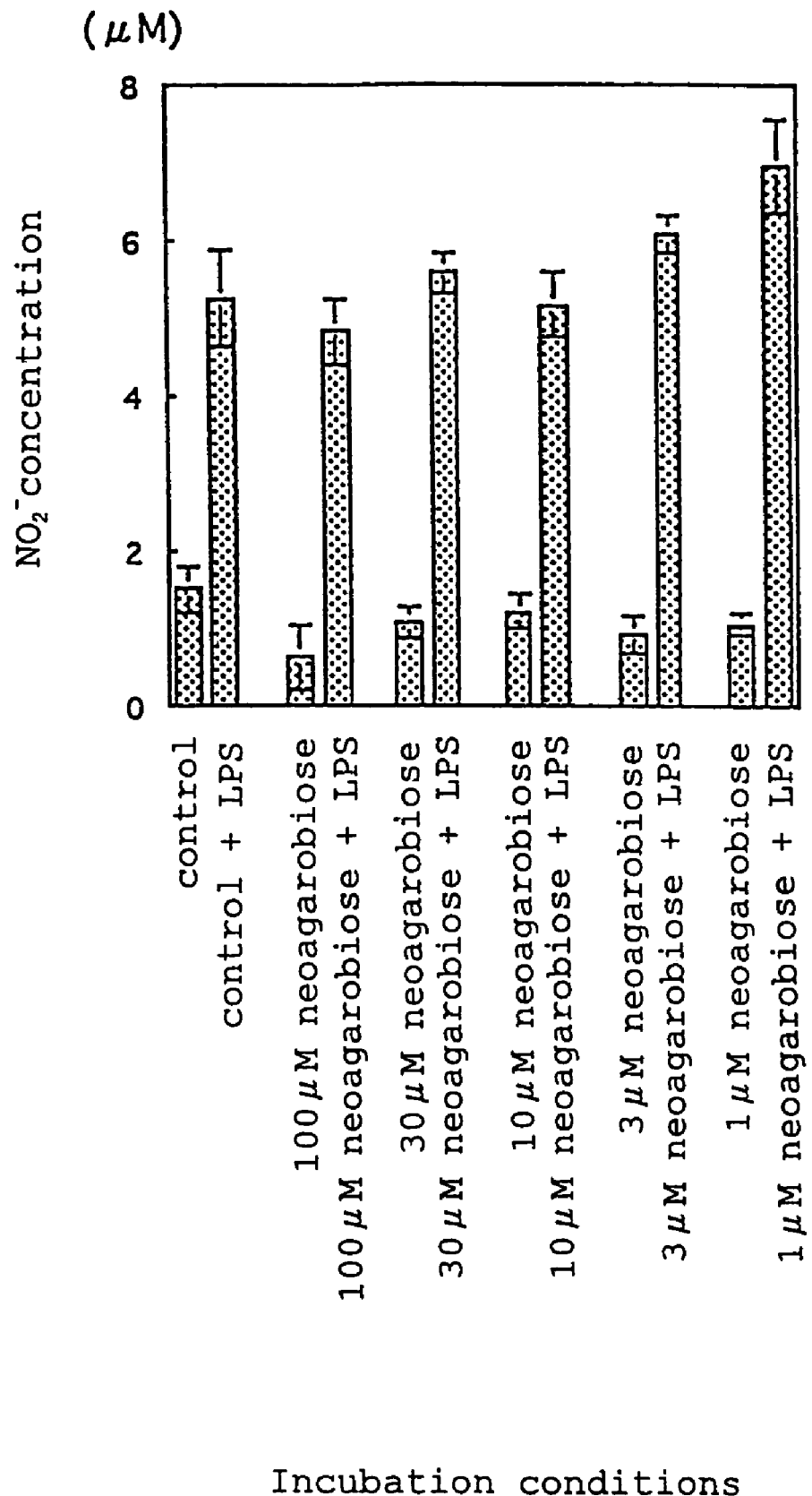
FIG. 37 illustrates $NO_2^-$ concentrations in culture media in the presence of various concentrations of neoagarobiose.

As a result, agarobiose dose-dependently inhibited NO production induced by LPS, while neoagarobiose did not. The results are shown in FIGS. 36 and 37. That is, FIG. 36 illustrates the $NO_2^-$ concentration in the medium incubated under the respective incubation conditions with addition of agarobiose. FIG. 37 illustrates the $NO_2^-$ concentration in the medium incubated under respective incubation conditions with addition of neoagarobiose. In FIGS. 36 and 37, the horizontal axes the represent incubation conditions and the vertical axes represent the $NO_2^-$ concentration (µM)

When 3,6-anhydrogalactopyranose, carabiose, agarotetraose, agarohexaose, agarooctaose and 3,6-anhydro-2-O-methyl-L-galactose were used instead of agarobiose, the similar results were obtained.

(2) A suspension of 5 g of commercially available agar (Ina agar type S-7, manufactured by Ina Shokuhin Kogyo) in 45 ml of 0.1 N HCl was treated at 95 C for 13 minutes. After cooling to room temperature, the suspension was neutralized with NaOH and filtered through 0.22 µm MILLEX-GP filter (manufactured by Milipore, SLGPR25LS). For this sample (agar decomposition product with hydrochloric acid) and agar decomposition oligosaccharide solution as described in Example 11-(1) (agar decomposition product with citric acid), according to the same manner as that described in Example 20-(1), an activity of inhibiting NO production was measured. Namely, 10 µl of 25 µg/ml LPS and 10 µl of a 20-fold dilution of the sample mentioned above were added to wells of a 48 well microtiter plate containing RAW264.7 cells which had been incubated in the wells. The measurement was carried out with the culture medium. As control groups, a group to which LPS was not added, a group to which a sample was not added and a group to which 2.5 mM citric acid was added were provided. All the measurement were carried out in duplicate.

Figure 38:
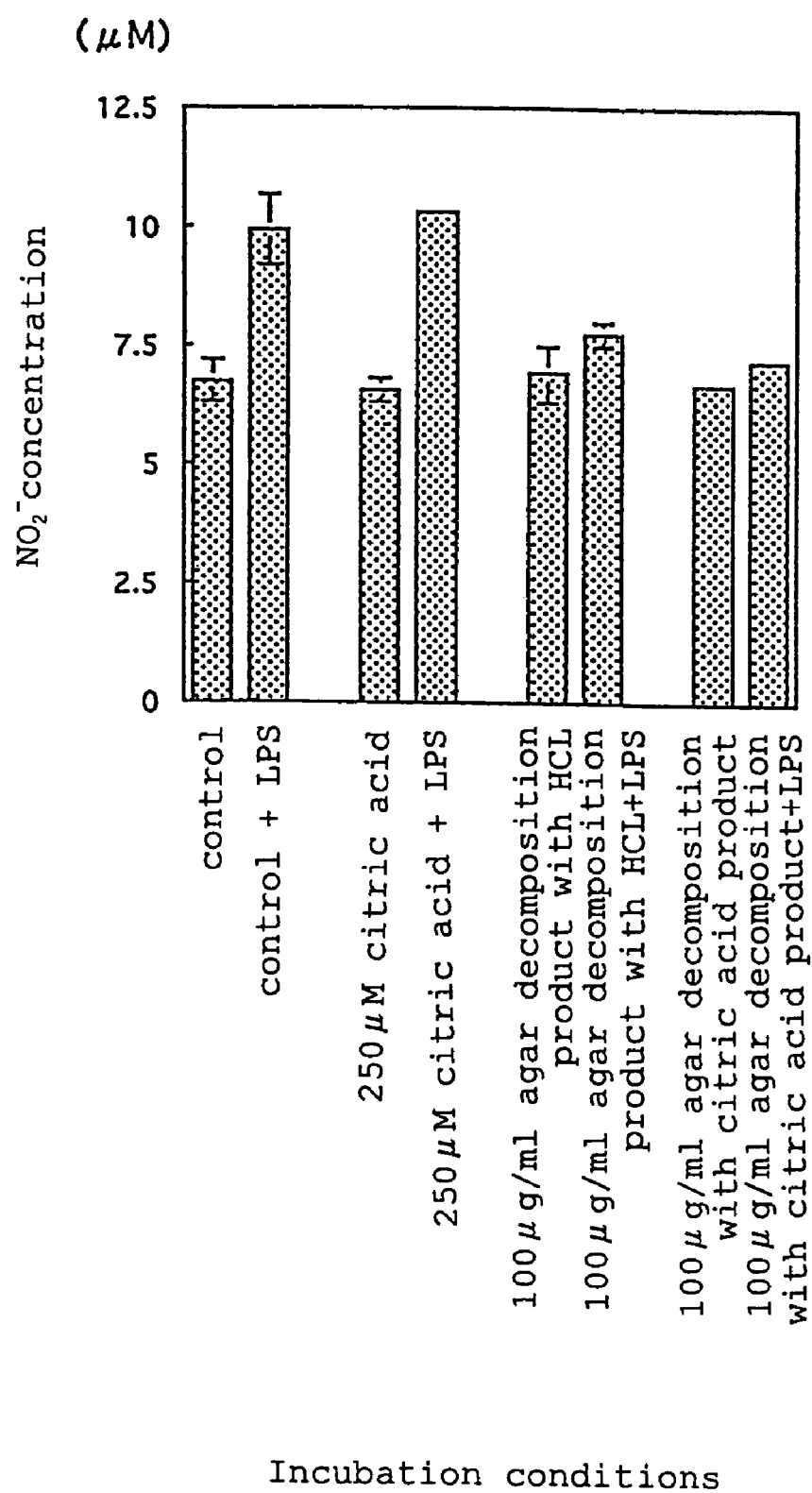
FIG. 38 illustrates $NO_2^-$ concentrations in culture media in the presence of a solution of agar digested by hydrochloric acid or citric acid.

As a result, both of the agar decomposition product with hydrochloric acid and the agar decomposition product with citric acid inhibited the NO production induced by LPS. The results are shown in FIG. 38. That is, FIG. 38 illustrates the $NO_2^-$ concentration in the medium cultured with addition of the agar decomposition product with hydrochloric acid or agar decomposition product with citric acid. In FIG. 38, the horizontal axis represents the incubation conditions and the vertical axis represents the $NO_2^-$ concentration (µM).

(3) According to the same manner as that described in Example 20-(2), an inhibitory activity against NO production was evaluated by using an aqueous 100 mM galactose (manufactured by Nacalai Tesque, code 165-11) or 100 mM 3,6-anhydro-D-galactose (manufactured by Funakoshi, code G0002) solution.

Figure 39:
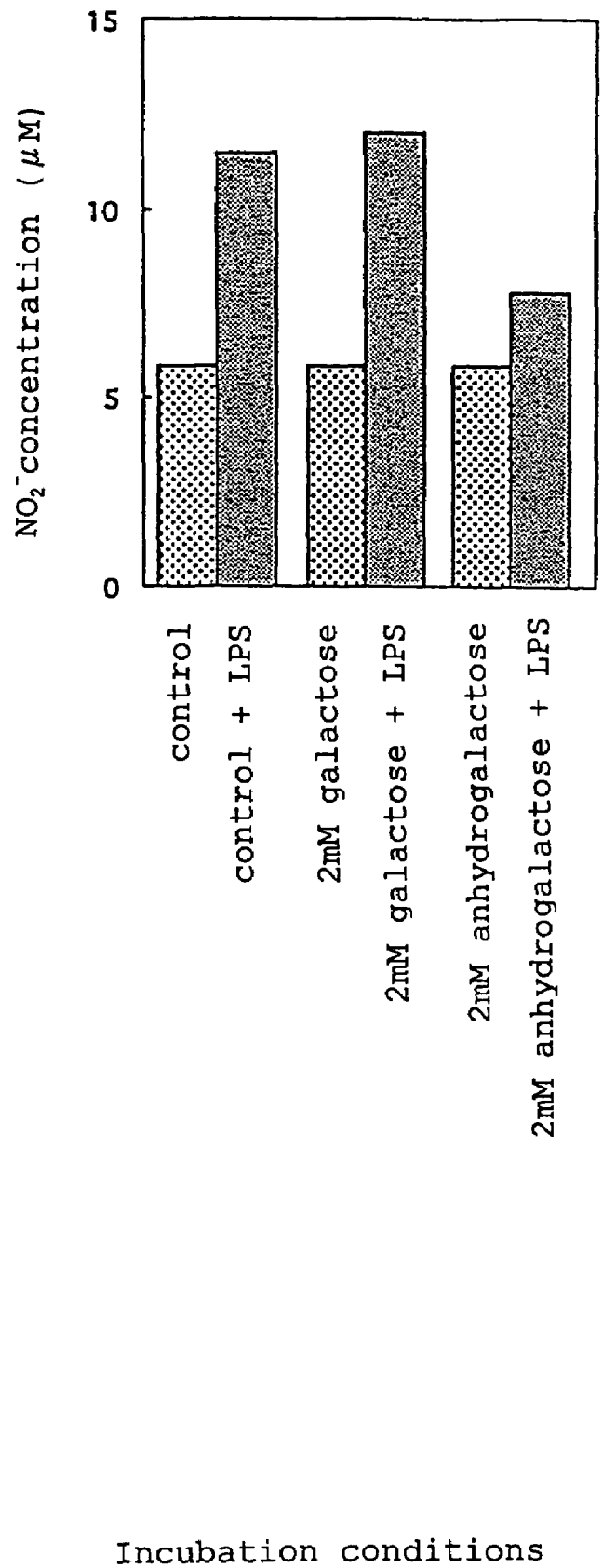
FIG. 39 illustrates $NO_2^-$ concentrations in culture media in the presence of 3,6-anhydro-D-galactose or galactose.

As a result, 3,6-anhydro-D-galactose inhibited NO production, while galactose did not. The results are shown in FIG. 39. That is, FIG. 39 illustrates the $NO_2^-$ concentration in the medium cultured with addition of 3,6-anhydro-D-galactose or galactose. In FIG. 39, the horizontal axis represents the incubation conditions and the vertical axis represents the $NO_2^-$ concentration (µM).

(4) RAW 264.7 cells were suspended in the Dulbecco's modified Eagle's medium described in Example 20-(1) at a concentration of $3\times10^5$ cells/ml, and 500 µl portions thereof were placed in respective wells of a 48 well microtiter plate. The plate was incubated for 37 C for 10 hours in the presence of 5% carbon dioxide. To the wells was added 10 [l of aqueous 5,000 µM agarobiose solution and incubated for additional 1, 2, 4 or 6 hours. Then, the culture supernatant was removed from the well and to each well were added 500 µl of fresh Dulbecco's modified Eagle's medium and then 10 µl of aqueous 2.5 µg/ml LPS and aqueous 800 U/ml interferon-γ (IFN-γ, sold by Cosmobio, GZM-MG-IFN) solution. The plate was incubated for 1 hour. Then, the culture supernatant was removed from the well and to each well was added 500 µl of fresh Dulbecco's modified Eagle's medium and the plate was incubated for additional 16 hours. The concentration of $NO_2^-$ produced by oxidation of NO in the medium was measured according to the same manner as that described in Example 20-(1). As control groups, a group to which neither LPS nor IFN-γ was added and a group to which agarobiose was not added were provided. All the measurements were carried out in duplicate.

Figure 40:
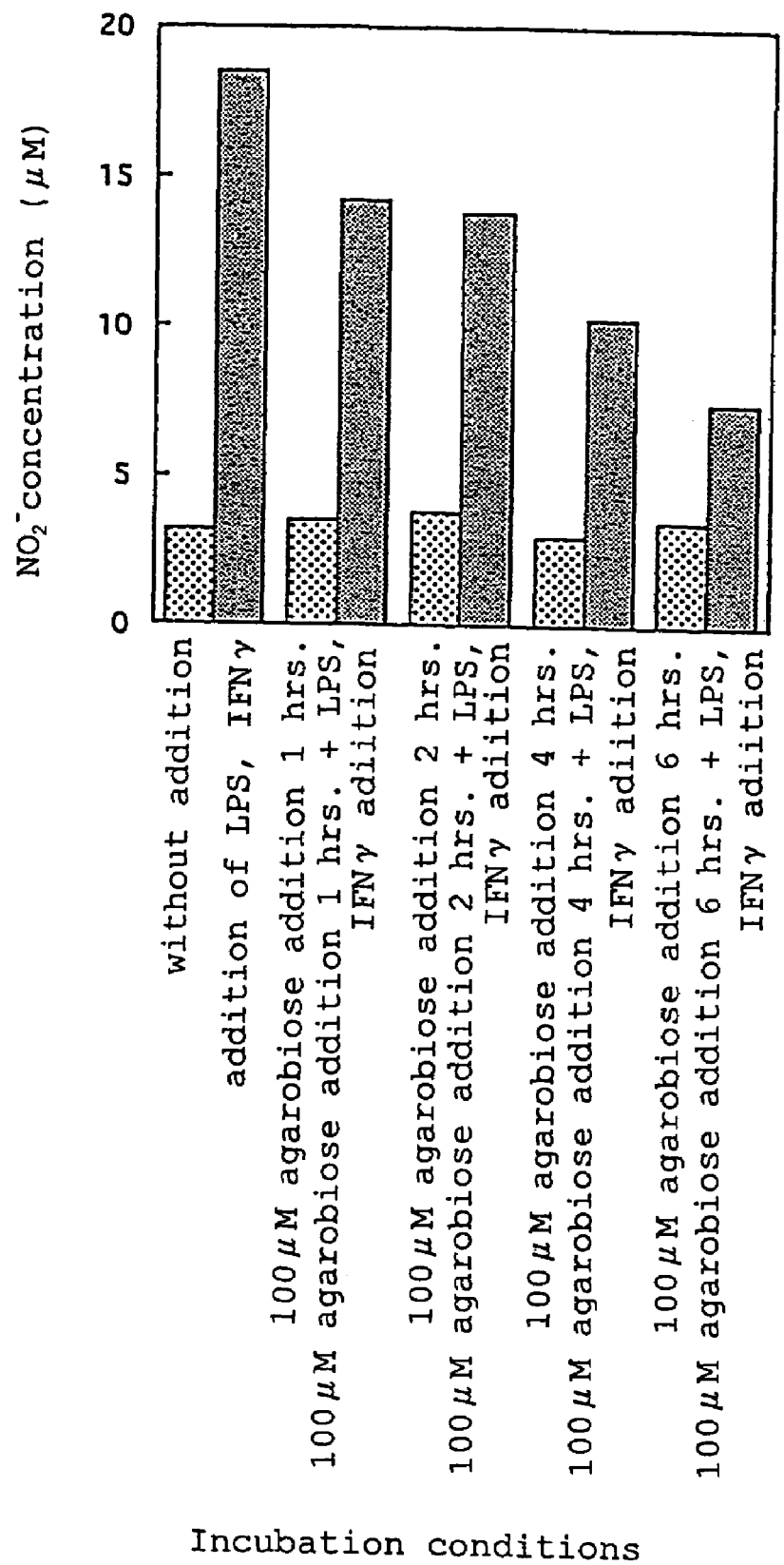
FIG. 40 illustrates $NO_2^-$ concentrations in culture media under various conditions.

As a result, the longer the pre-incubation time was, the higher the inhibition of NO production by agarobiose was. Namely, by addition of agarobiose to a cell culture medium beforehand, NO production induced by LPS and IFN-Y could be inhibited and prevented. The results are shown in FIG. 40. FIG. 40 illustrates the $NO_2^-$ concentration in the medium cultured under respective incubation conditions. In FIG. 40, the horizontal axis represents the incubation conditions and the vertical axis represents the $NO_2^-$ concentration. For 3,6-anhydrogalactopyranose, agarotetraose, agarohexaose, agarooctaose, carabiose and 3,6-anhydro-2-O-methyl-L-galactose, the similar activities have also been recognized.

EXAMPLE 21

(1) Agar powder (manufactured by Wako Pure Chemical Industries, Ltd.) was added to 50 mM citric acid solution at a final concentration of 3%. The resultant was heat-treated at 95 C for 160 minutes to prepare an oligosaccharide solution for a carcinostatic test.

Male nude mice (SPF/VAFBalb/cAnNCrj-nu, 4 weeks old) were purchased from Nippon Charles River and pre-bred for 1 week. Human colon cancer cell line HCT116 (ATCC CCL-247) were transplanted subcutaneously to the mice at $1.5\times10^6$ cells/mouse.

After 2 weeks from the transplantation of the colon cancer cell line, the above oligosaccharide solution for the carcinostatic test which was adjusted to pH 6.5 just before use was freely given to the mice as drinking water for 5 days per week. The average of daily intake per one mouse was 3.5 ml. Furthermore, MF manufactured by Oriental Yeast was freely given to the mice as feed.

After 4 weeks from the beginning of administration of oligosaccharides, the solid cancer was removed from each mouse that received oligosaccharides and the weight of each solid cancer was compared with that of a control to which normal water was given. This test was carried out using 10 mice per one group.

As a result, a significant activity of inhibiting cancer cell growth was observed in the group to which the sample for the carcinostatic test was administrated orally, and a strong carcinostatic activity was observed in the group to which the oligosaccharides derived from agar was administrated orally.

Figure 41:
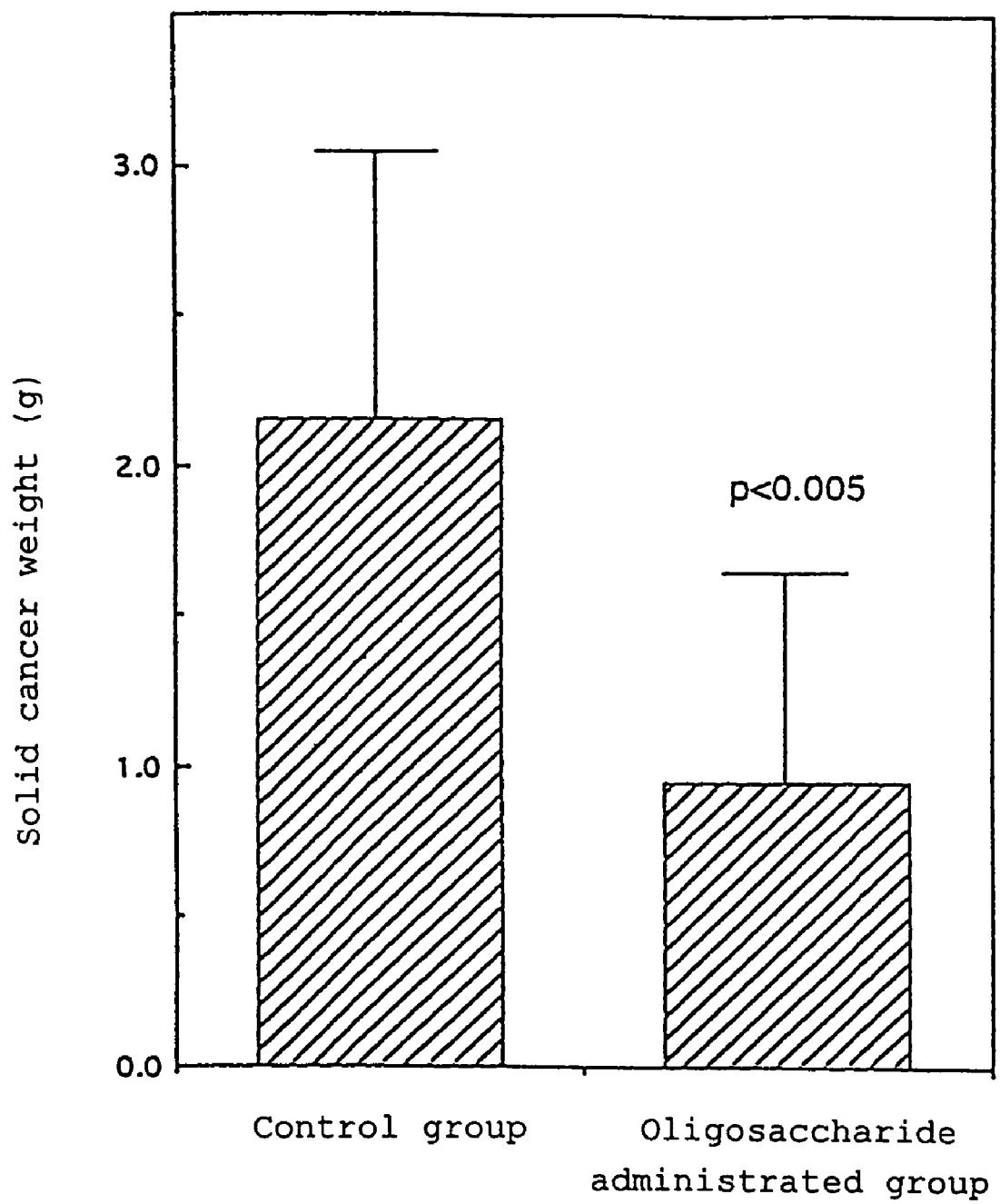
FIG. 41 illustrates carcinostatic activity of the oligosaccharide of the present invention.

The results are shown in FIG. 41. That is, FIG. 41 illustrates the carcinostatic activity of the oligosaccharides of the present invention. The vertical axis represents the weight of solid cancer (g) and the horizontal axis represents the control group and the group administrated with oligosaccharide.

In one mouse of the group to which the neutralized sample for the carcinostatic test was administrated orally, the cancer was completely disappeared.

(2) A carcinostatic test was carried out against Ehrlich's ascites carcinoma using the agar decomposition oligosaccharide solution as described in Example 11-(1).

Ehrlich's carcinoma cells were injected to female ddY line mice (5 weeks old, weighing about 25 g) intraperitoneally ($1.2 \times 10^6$ cells/mouse) and average days of survival and prolongation rates were calculated based on the number of survived animals.

Mice were divided into 3 group each consisting of 8 mice. One was a control, and other two groups received 3.3-fold dilution and 16.7-fold dilution of the agar decomposition oligosaccharide solution described in Example 11-(1), respectively. Namely, each aqueous dilution of the agar decomposition oligosaccharide solution prepared in Example 11-(1) was prepared and was freely given to the mice from 3 days before cancer cell administration. For the group to which the 3.3-fold dilution of the agar decomposition oligosaccharide solution was given, the daily intake of the dilution was 5 ml/day/mouse. For the group to which the 16.7-fold dilution of the agar decomposition oligosaccharide solution was given, the daily intake of the dilution was 6 ml/day/mouse. And, for the control group, the daily intake of water was 7 ml/day.

As a result, while the average days of survival of the control group was 11.8 days for the control group, the average days of survival for the groups received the 3.3-fold dilution and the 16.7-fold dilution were 19.8 days and 14.4 days, and the prolongation rates were 168% and 122%, respectively. Thus, a significant prolongation effect was recognized.

EXAMPLE 22

To Wistar line rat (male, 5 weeks old, weighing about 150 g ; Nippon SLC) were injected 100 µg of ovalbumin (OA; Sigma) and 1 ml of alum (trade name: Imject Alum; Piace) intraperitoneally to sensitized the rat. After 14 days, peripheral blood was collected from the abdominal aorta of the rat and the serum was used as anti-OA antibody.

The back part of Wistar line rat (male, 7 weeks old, weighing about 200 g; Nippon SLC) was shaved and 100 µl of the anti-OA antibody was injected subcutaneously to that part to give passive sensitization. Forty-eight hours after sensitization, 2 ml of agar decomposition oligosaccharide solution described in Example 11-(1) or its 10-fold dilution was administrated intraperitoneally to 4 rats of each group. To rats of a control group, 2 ml of water was administrated intraperitoneally.

Thirty minutes after administration, PCA was raised by injection of 1 ml of saline containing 0.1% OA and 0.5% Evan's blue (Nacalai Tesque) to the tail vein. Thirty minutes after the induction with antigen, rats were killed by decapitating and bleeding, and the skin of the back site where the pigment was leaked was removed and collected.

The collected skins were soaked in 1 ml of 1 N KCl (Nacalai Tesque) and allowed to stand overnight. Then, the pigment was extracted by adding 9 ml of acetone solution (Nacalai Tesque) containing 0.6 N $H_3PO_4$ (Merck) and the absorbance at 620 nm was measured using an ELISA reader. The amount of the pigment leaked from the skin was calculated from a calibration curve of Evan's blue.

Figure 42:
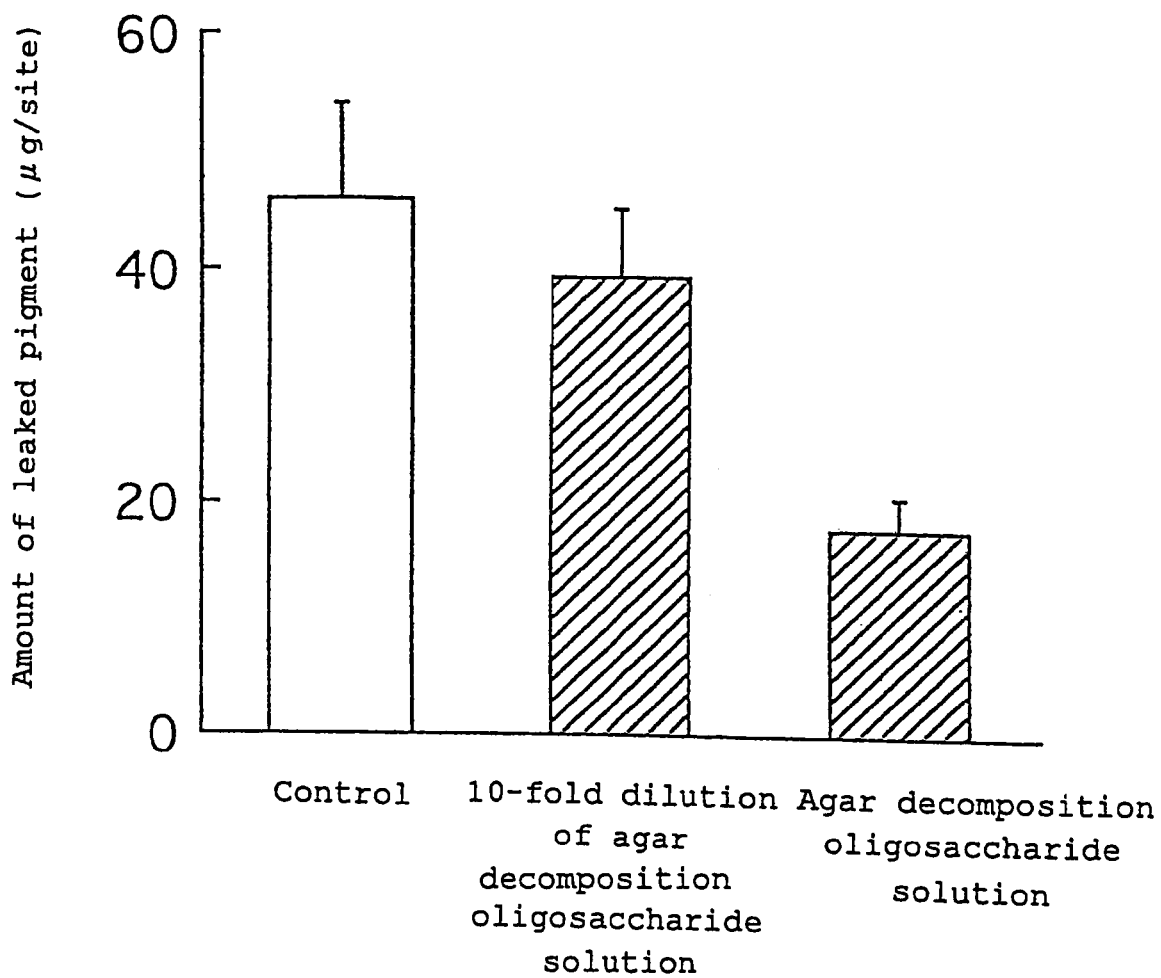
FIG. 42 illustrates inhibition of PCA reaction by the oligosaccharide of the present invention.

The results are shown in FIG. 42. That is, FIG. 42 illustrates inhibition of PCA by the oligosaccharides of the present invention. In FIG. 42, the vertical axis represents the amount of leaked pigment (µg/site), and the horizontal axis represents the agar decomposition oligosaccharide solution used.

As shown in FIG. 42, one half or more pigment leakage by PCA was inhibited by administration of the agar decomposition oligosaccharide solution and, as compared with the control, significant difference ($p<0.05$) was exhibited.

For 3,6-anhydrogalactopyranose, agarobiose, agarotetraose, agarohexaose, agarooctaose, carabiose and 3,6-anhydro-2-O-methyl-L-galactose, the similar activities have also been recognized.

EXAMPLE 23

Mouse melanoma cell B16BL6 suspended in RPMI-1640 containing 10% FBS was placed in a 6 well plate at a concentration of $5 \times 10^4$ cells/2 ml medium/well and incubated at 37 C. On the 2nd day, 100 µl of agarobiose solution (2 mg/ml to 0.2 mg/ml) was added thereto, and on the 7th day, the medium was changed and, at the same time, 100 µl of agarobiose solution (2 mg/ml to 0.2 mg/ml) was added thereto. On the 8th day, the cells were collected, DNA, RNA and protein were decomposed, and then the absorbance at 400 nm was measured to examine an activity of inhibiting melanin production.

Namely, after removing the medium by suction, 0.3 ml of 0.25% trypsin dissolved in 20 mM EDTA solution was added to each well and the plate was incubated at 37 C for 10 minutes. Then, 2 ml of the fresh medium was added to the well and the cells were suspended. The suspension was collected into a test tube. The medium was then removed by centrifugation and the cells were suspended in 2 ml of PBS and centrifuged again. After removing the supernatant, 30 µl of 50 mM sodium acetate buffer (pH 5.0) containing 5 mM manganese chloride and 1 µl of 70,000 U/ml DNase I (manufactured by Takara Shuzo) were added to the cells and thoroughly mixed. The mixture was incubated at 37 C for 2 hours to decompose DNA. Then, 1 µl of 10 mg/ml ribonuclease A (manufactured by Sigma) was added to the mixture and the resultant mixture was incubated at 50 C for 1 hour to decompose RNA. Finally, 100 mM Tris-hydrochloric acid buffer (pH 7.8) containing 100 µg/ml proteinase K (manufactured by Sigma), 0.1% Triton x and 10 mM EDTA was added thereto to make the total volume up to 200 µl for $2 \times 10^6$ cells, and the mixture was incubated at 37 C for 16 hours and then the absorbance at 400 nm was measured.

The result was shown in Table 15. As shown in Table 15, activity of the inhibiting melanin production was recognized at agarobiose concentrations of 50 and 100 µg/ml and the beautifying/whitening effect of agarobiose was recognized. For agarotetraose, agarohexaose, agarooctaose, carabiose and 3,6-anhydro-2-O-methyl-L-galactose, the similar activities have also been recognized.

TABLE 15

| Agarobiose | Absorbance at 400 nm | | |
|---|---|---|---|
| μg/ml | mean | ± | SD |
| 100 | 0.383 | ± | 0.007 |
| 50 | 0.392 | ± | 0.172 |
| 10 | 0.521 | ± | 0.256 |
| control | 0.487 | ± | 0.038 |

Note: The measurement was carried out in triplicate; 100 μl of the medium was added to the control.

As described above, according to the present invention, there is provided the functional substances which are useful as active ingredients for compositions for inducing apoptosis, carcinostatic compositions, antioxidants such as inhibitors of active oxygen production, inhibitors of lipid peroxide radical production and inhibitors of NO production, and immunoregulators, and which are the members selected from the group consisting of the compounds selected from the group consisting of 3,6-anhydrogalactopyranose, a aldehyde and a hydrate thereof, and 2-O-methylated derivatives of the 3,6-anhydrogalactopyranose, the aldehyde and the hydrate, and the soluble saccharides containing said compounds, for example, agarobiose, agarotetraose, agarohexaose, agarooctaose, carabiose, 3,6-anhydro-2-O-methyl-L-galactose, etc. produced by acid decomposition under acidic condition below pH 7 and/or enzymatic digestion of substances containing the above-mentioned compounds.

These substances are useful as active ingredients of pharmaceutical compositions such as compositions for inducing apoptosis, carcinostatic compositions, antioxidants for medical use such as inhibitors of active oxygen production, inhibitors of NO production, etc., immunoregulators, and anti-allergic agents. And, the foods or drinks comprising, produced by adding thereto and/or diluting saccharides selected from these saccharides are useful for functional foods or drinks having an activity such as an activity of inducing apoptosis, a carcinostatic activity, an antioxidant activity such as an activity of inhibiting active oxygen production, an activity of inhibiting NO production, an immunoregulatory activity and an anti-allergic activity. Thus, there is provided foods or drinks which induce apoptosis in cells in lesions in patients suffered from cancers or viral diseases and, therefor, are effective in preventing or ameliorating the disease states of these diseases. In a case of a cancer of a digestive organ such as colon cancer and stomach cancer, among others, since apoptosis can be induced in tumor cells upon oral intake of the above-mentioned compounds of the present invention in foods or drinks, the foods or drinks of the present invention have excellent effects on the prevention or amelioration of the disease state of a cancer of a digestive organ. Furthermore, the above-mentioned foods or drinks are useful foods or drinks for opposing oxidative stress on the basis of their antioxidant activities such as the activity of inhibiting the active oxygen production.

In addition, the functional substances of the present invention are also useful as saccharides for an antioxidant for inhibition of active oxygen production, and the foods or drinks comprising, produced by adding thereto and/or produced by diluting the saccharides for an antioxidant of the present invention are useful as those for ameliorating the disease states of diseases caused by oxidizing substances in a living body such as active oxygen. Furthermore, the foods or drinks of the present invention are effective for amelioration or prevention of constipation by the activity of their active ingredients, i.e., a member selected from the group consisting of the compound selected from the group consisting of 3,6-anhydrogalactopyranose, an aldehyde, and 2-O-methylated derivatives thereof and/or the saccharide containing said compound.

The saccharides for an antioxidant provided by the present invention are useful as novel functional saccharides which provide antioxidant activities such as an activity of inhibiting active oxygen production to foods or drinks.

The functional substances of the present invention have a freshness keeping activity and are very useful for keeping taste or freshness of foods or perishables.

Furthermore, the cosmetic compositions comprising the saccharides of the present invention are useful as those for beautifying/whitening or moisturizing.

According to the present invention, there is also provided acidic foods or drinks comprising, produced by adding thereto and/or produced by diluting the functional substances. In the production of such foods or drinks, factors which influence to the contents of the functional substances have been substantially eliminated and, therefore, very useful foods or drinks having high contains of the functional substances are obtained. Moreover, the acidulant prepared in the presence of an organic acid is also useful as a novel acidulant having good taste and functions.

What is claimed is:

1. A method for treating a carcinomatous disease or an allergic disease, the method comprising
   administering to a subject in need thereof, a pharmaceutical composition which comprises as an active ingredient at least one member selected from the group consisting of:
   (1) a compound selected from the group consisting of 3,6-anhydrogalactopyranose represented by the formula (I):

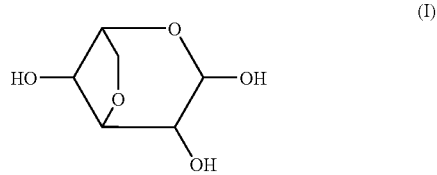

(I)

an aldehyde thereof, a hydrate thereof, and a 2-O-methylated derivative of said 3,6-anhydrogalactopyranose, said aldehyde or said hydrate; and
   (2) a soluble saccharide containing the compound at its reducing end.

2. A method according to claim 1, wherein the saccharide is a product produced by acid decomposition under acidic conditions below pH 7 and/or enzymatic digestion of a substance containing at least one compound selected from the group consisting of 3,6-anhydrogalactopyranose represented by said formula I, an aldehyde or a hydrate thereof, and a 2-O-methylated derivative of the 3,6-anhydrogalactopyranose, said aldehyde or said hydrate.

3. A method according to claim 2, wherein the substance containing at least one compound selected from the group consisting of 3,6-anhydrogalactopyranose represented by formula I, an aldehyde and a hydrate thereof, and 2-O-methylated derivatives of the 3,6-anhydrogalactopyranose, the aldehyde and the hydrate is at least one substance selected from the group consisting of agar, agarose and carrageenan.

4. A method according to claim 1, wherein the saccharide is at least one saccharide selected from the group consisting of agarobiose, agarotetraose, agarohexaose, agarooctaose, κ-carabiose, and β-D-galactopyranosyl-3,6-anhydro-2-O-methyl-L-galactose.

* * * * *